(12) United States Patent
Wong et al.

(10) Patent No.: US 10,155,823 B2
(45) Date of Patent: Dec. 18, 2018

(54) GLYCAN CONJUGATES AND USE THEREOF

(71) Applicant: ACADEMIA SINICA, Taipei (TW)

(72) Inventors: Chi-Huey Wong, Rancho Santa Fe, CA (US); Chung-Yi Wu, New Taipei (TW); Hsin-Yu Lee, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 52 days.

(21) Appl. No.: 15/505,763

(22) PCT Filed: Aug. 21, 2015

(86) PCT No.: PCT/US2015/046197
§ 371 (c)(1),
(2) Date: Feb. 22, 2017

(87) PCT Pub. No.: WO2016/029071
PCT Pub. Date: Feb. 25, 2016

(65) Prior Publication Data
US 2017/0275389 A1    Sep. 28, 2017

Related U.S. Application Data

(60) Provisional application No. 62/040,756, filed on Aug. 22, 2014.

(51) Int. Cl.
| | | |
|---|---|---|
| C07H 3/06 | (2006.01) | |
| A61K 39/00 | (2006.01) | |
| A61K 47/36 | (2006.01) | |
| A61K 47/64 | (2017.01) | |
| C07K 14/33 | (2006.01) | |
| C07K 14/34 | (2006.01) | |
| C08B 37/00 | (2006.01) | |

(52) U.S. Cl.
CPC ...... *C08B 37/0024* (2013.01); *A61K 39/0011* (2013.01); *A61K 39/0016* (2013.01); *A61K 47/36* (2013.01); *A61K 47/646* (2017.08); *A61K 47/6415* (2017.08); *C07K 14/33* (2013.01); *C07K 14/34* (2013.01); *A61K 2039/555* (2013.01); *A61K 2039/6037* (2013.01); *C07H 3/06* (2013.01); *G01N 2333/4728* (2013.01)

(58) Field of Classification Search
None
See application file for complete search history.

(56) References Cited

U.S. PATENT DOCUMENTS

| | | |
|---|---|---|
| 2003/0083235 A1 | 5/2003 | Danishefsky et al. |
| 2004/0102607 A1 | 5/2004 | Danishefsky et al. |
| 2005/0222398 A1 | 10/2005 | Danishefsky et al. |
| 2010/0239601 A1 | 9/2010 | Kossaczka et al. |
| 2012/0328646 A1 | 12/2012 | Wong et al. |

*Primary Examiner* — Karen A. Canella
(74) *Attorney, Agent, or Firm* — Muncy, Geissler, Olds & Lowe, PC

(57) ABSTRACT

This disclosure includes an immunogenic composition containing (a) a glycan conjugate including a carrier and one or more glycans, wherein each of the one or more glycans is conjugated with the carrier through a linker, and optionally (b) an adjuvant. The one or more glycan is each a Globo H derivative.

24 Claims, 2 Drawing Sheets

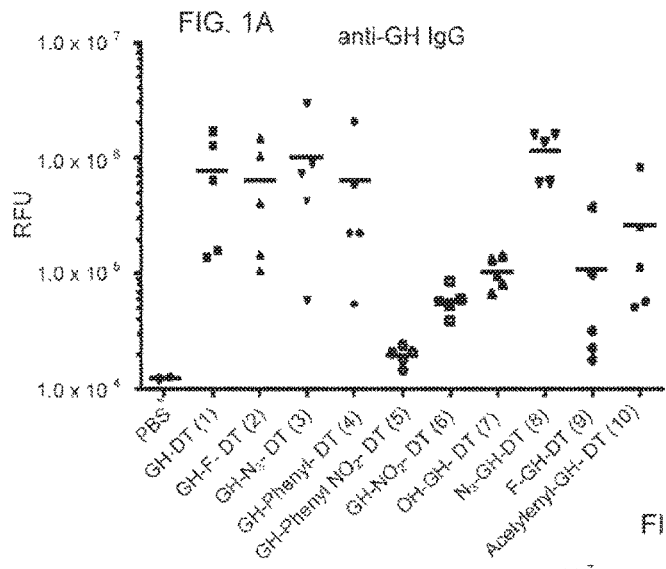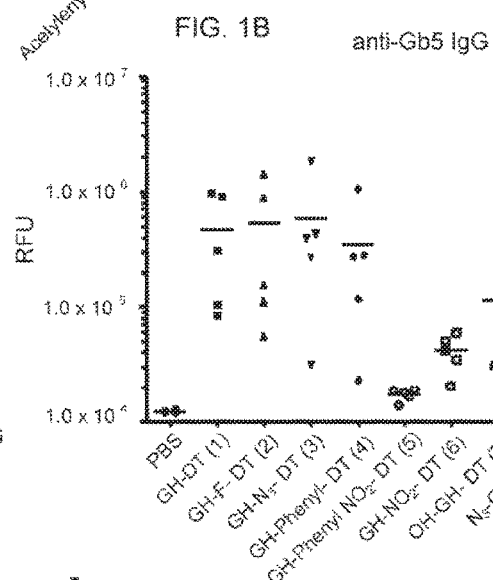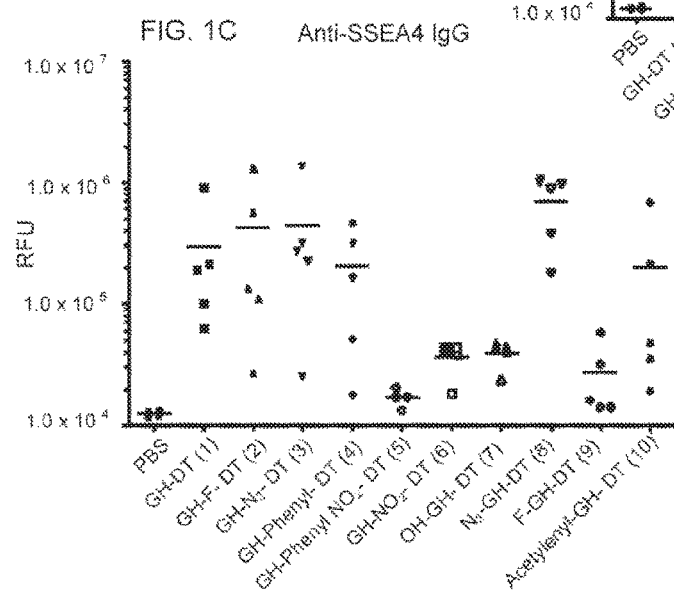

GLYCAN CONJUGATES AND USE THEREOF

BACKGROUND OF THE INVENTION

Tumor associated carbohydrate antigens (TACAs) are over expressed on the surface of cancer cells and related to tumor cell adhesion and metastasis.[1] Thus. TACAs are potential targets for cancer vaccine development.[2] However, most TACAs have poor immunogenicity and many approaches have been developed to increase the immune response of carbohydrate-based vaccines, including conjugation with a carrier protein[3], administration with an immunologic adjuvant[4], using unnatural glycosidic linkage[5], clustered antigens[6], unimolecular polyvalent vaccine[7] or heteroglycan multivalent vaccine[8]. Using these strategies, a few carbohydrate-based vaccines that could elicit significant immune responses to target glycan structures were designed for cancer therapy and entered clinical trials.[3,9] Among them, the clinical trials of Theratope and GMK with adjuvant QS-21 failed to produce statistically significant difference between time-to-disease and overall survival rate. Probably these two vaccines could not elicit robust T cell-dependent immune response in patients.[10] Specifically, Theratope and GMK induced a higher level of IgM in patients but could not induce a strong immune IgG response, which is a major problem in carbohydrate-based vaccine development.[11]

Globo H (GH; Fucα1→2Galβ1→3GalNacβ1→3Galα1→4Galβ1→4Glc) is a member of the globo series glycosphingolipids. It was first found and characterized in human teratocarcinoma cells and breast cancer MCF-7 cells in 1983,[12] and was subsequently found overexpressed in many types of human cancer cells including breast, prostate, ovary, pancreas, brain, endometrium, gastric, colon and lung cancers.[13] A Globo H vaccine using KLH as carrier and QS-21 as adjuvant prepared by Livingston and Danishefsky showed a positive result in a phase I study against metastatic breast cancer patients.[14] With improvement in synthesis[15], it is now in phase III clinical trial in Taiwan and phase II clinical trial in the USA, Korea, Hong-Kong and India for late stage breast cancer patients and in phase II clinical trial for ovarian cancer patients in Taiwan. However, these early stage clinical results showed that the induced IgM antibodies were still much higher than IgG antibodies.[14,16] Recently, our group has developed a better vaccine using diphtheria toxoid cross-reactive material (CRM) 197 (DT) as carrier and a glycolipid C34 as adjuvant to induce a class switch with robust IgG antibody response against GH, its fragment Gb5 and SSEA4, all found on breast cancer cells and the cancer stem cells only.[13b]

Previous studies showed that modification of carbohydrate antigen structures (MCAS) could effectively elicit a higher level of immune response.[17] For example, in the modification study of the capsular polysaccharide of group B meningococci, the N-acetyl groups of α-(2,8)-linked polysialic acid (PSA) was replaced with the N-propinoyl group and such a modification elicited a high antibody response to recognize not only the N-propinoyl PSA, but also the nature N-acetyl PSA.[18] Similar approaches were applied to STn[19] and GM3[20] antigens to produce high antibody titers against modified and nature forms. The results indicated that N-phenylacetyl, $N_3$, N-fluoroacetyl or N-difluoroacetyl modifications on glycan antigens could improve the immunogenicity.[19a,c] Moreover, the Schultz group reported that incorporation of a p-nitrophenylalanine into the tumor necrosis factor-α (TNF-α) could break immune tolerance and induce more antibody response to TNF-α.[21] Using glycans as antigens, although some progress has been achieved, most cases are the N-modification of disaccharide (STn), trisaccharide (GM3) and polysialic acid (PSA) and some are based on fluorinated MUC1 glycopeptide antigens.[18a,19a,d,20,22] There is a lack of a general strategy for the preparation of carbohydrate-based vaccines to induce IgG response with a long-term memory.

SUMMARY OF THE INVENTION

The present invention relates to the unexpected discoveries that the modification at the reducing end glucose or the non-reducing end fucose of Globo 1H with certain groups disclosed herein elicited robust IgG antibody response to specifically recognize Globo H (GH), Gb5 and SSEA4. The antibodies induced by an immmunogenic composition comprising such unnatural glycan moiety were found to recognize GH expressing tumor cells (MCF-7) and mediate the complement-dependent cell cytotoxicity against tumor cells.

Accordingly, the invention relates to synthetic glycan conjugates, immmunogenic compositions comprising such, and vaccines thereof. The invention also relates to methods of using the synthetic glycan conjugates and immunogenic compositions thereof to treat or reduce the risk for cancers.

In one aspect, the invention relates to a compound of formula (I)

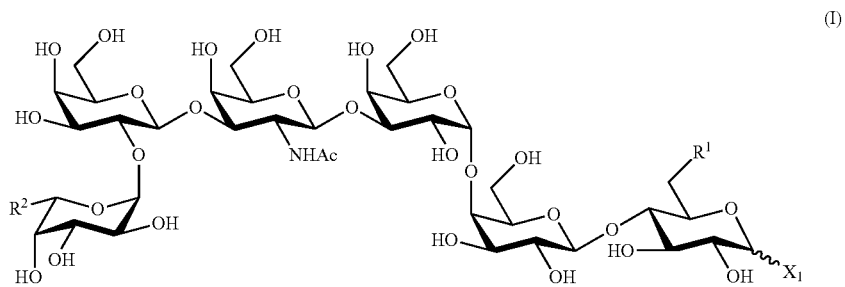

or a salt thereof,
wherein:
   $X_1$ is —OR or —SR, wherein R is hydrogen, an oxygen or a sulfur protecting group, optionally substituted $C_{1-10}$ alkyl, optionally substituted aryl, optionally substituted acyl, or optionally substituted imidoyl;
   $R^1$ and $R^2$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

$R^A$ is independently selected from hydrogen, optionally substituted alkyl, optionally substituted alkenyl, optionally substituted alkynyl, optionally substituted heterocyclyl, and optionally substituted aryl;

$R^B$ is independently selected from hydrogen, optionally substituted alkyl, optionally substituted alkenyl, optionally substituted alkynyl, optionally substituted heterocyclyl, and optionally substituted aryl; and provided that when $R^1$ is —OH, $R^2$ is not —$CH_3$; and when $R^2$ is —$CH_3$, $R^1$ is not —OH.

In another aspect, the invention relates to an immunogenic composition, comprising (a) a glycan conjugate comprising at least one glycan with a linker and a carrier, the at least one glycan being conjugated to the carrier through the linker; and (b) optionally an adjuvant, wherein the at least one glycan with the linker has a chemical structure of formula (II):

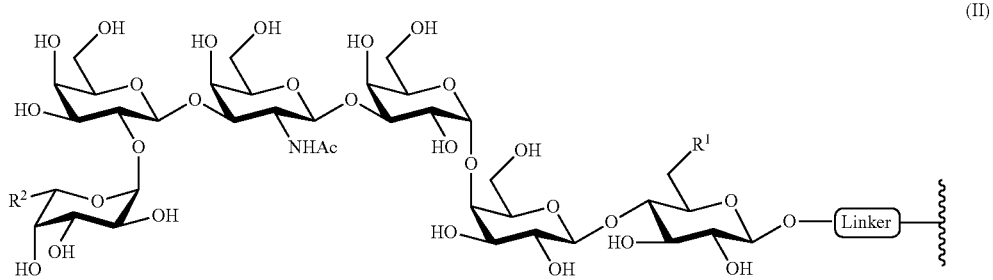

(II)

wherein:

$R^1$ and $R^2$ is independently selected from hydrogen, halogen, optionally substituted alkyl, optionally substituted alkenyl, optionally substituted alkynyl, optionally substituted heterocyclyl, optionally substituted aryl, —$N_3$, —$NO_2$, —$N(R^B)_2$, —$N(R^A)C(O)R^A$, —$OR^A$, —$OC(O)R^A$, —$SR^A$, —$C(O)N(R^B)_2$, —CN, —$C(O)R^A$, —$C(O)OR^A$, —$S(O)R^A$, —$SO_2R^A$, —$SO_2N(R^B)_2$, and —$NHSO_2R^B$;

$R^A$ is independently selected from hydrogen, optionally substituted alkyl, optionally substituted alkenyl, optionally substituted alkynyl, optionally substituted heterocyclyl, and optionally substituted aryl;

$R^A$ is independently selected from hydrogen, optionally substituted alkyl, optionally substituted alkenyl, optionally substituted alkynyl, optionally substituted heterocyclyl, and optionally substituted aryl; and provided that when $R^1$ is —OH, $R^2$ is not —$CH_3$; and when $R^2$ is —$CH_3$, $R^1$ is not —OH.

Alternatively, the at least one glycan with the linker has a chemical structure of Formula (IV):

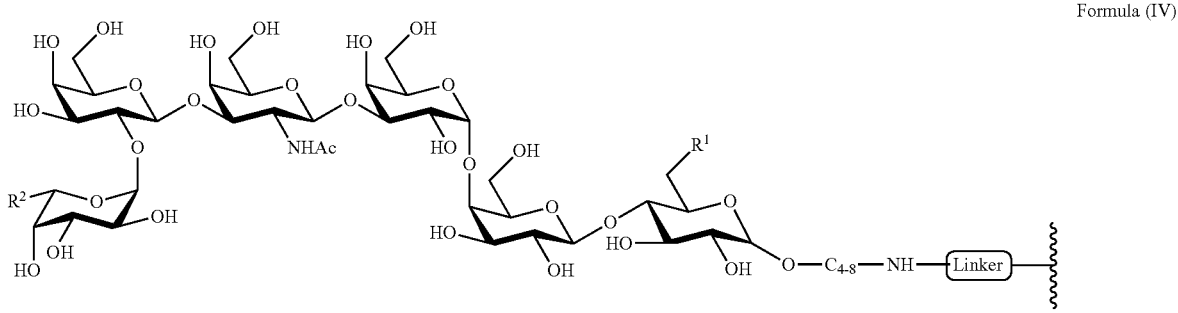

Formula (IV)

wherein R¹ and R² R^A R^B are as defined above in Formula and provided that when R¹ is —OH, R² is not —CH₃, and when R is —CH₃, R¹ is not —OH.

In one embodiment of the invention, R¹ is —OH, —F, —N₃, —NO₂, or aryloxy.

In another embodiment, R² is —CH₃, —CH₂F, —CH₂N₃, —CH₂NO₃, —CH₂OH, or alkynyl.

In another embodiment, R¹ is —F, —N₃, —NO₂,

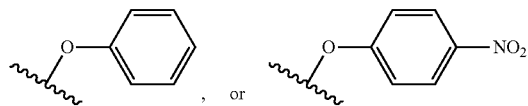 [SMILES: *Oc1ccccc1 ; *Oc1ccc([N+](=O)[O-])cc1]

, or and R² is —CH₃.

In another embodiment, R¹ is —OH and R² is —CH₂F, —CH₂N₃, —CH₂OH, or —C≡CH.

The term "n" represents an integer from 1 to 10. Thus, n may be 1, 2, 3, 4, 5, 6, 7, 8, 9, or 10.

In another embodiment, the linker is a hetero- or honorbifunctional linker.

In another embodiment, the linker is -L¹-L²-, wherein L¹ is a bond, —O—, —S—, —NR^{L1a}—, —C(=O)—, —NR^{L1a}C(=O)—, —NR^{L1a}C(=O)O—, —C(=O) NR^{L1a}—, —OC(=O)NR^{L1a}—, —SC(=O)—, —C(=O) S—, —OC(=O)—, —C(=O)O—, —NR^{L1a}C(=S)—, —C(=S)NR^{L1a}—, trans-CR^{L1b}=CR^{L1b}—, cis-CR^{L1b}=CR^{L1b}—, —C≡C, —OC(R^{L1b})₂—, —C(R^{L1b})₂ O—, —NR^{L1a}C(R^{L1b})₂—, —C(R^{L1b})₂NR^{L1a}—, —SC (R^{L1b})₂—, —C(R^{L1b})₂S—, —S(=O)₂O—, —OS(=O)₂—, —S(=O)NR^{L1a}—, —NR^{L1a}S(=O)₂—, or an optionally substituted C₁₋₂₀ hydrocarbon chain, optionally wherein one or more carbon units of the hydrocarbon chain is replaced with —O—, —S—, —NR^{L1a}—, —C(=O)—, —NR^{L1a}C (=O)—, —NR^{L1a}C(=O)O—, —C(=O)NR^{L1a}—, —OC (=O)NR^{L1a}—, —SC(=O)—, —C(=O)S—, —OC (=O)—, —C(=O)O—, —NR^{L1a}C(=S)—, —C(=S) NR^{L1a}—, trans-CR^{L1b}=CR^{L1b}—, cis-CR^{L1b}=CR^{L1b}—, —C≡C—, —S(=O)₂O—, —OS(=O)₂—, —S(=O)₂ NR^{L1a}—, or —NR^{L1a}S(=O)₂—, wherein R^{L1a} is hydrogen, optionally substituted C₁₋₆ alkyl, or a nitrogen protecting group, or R^{L1a} is joined with the adjacent carbon atom to form an optionally substituted heterocyclic rind, and wherein each occurrence of R^{L1b} is independently selected from the group consisting of hydrogen, halogen, optionally substituted C₁₋₁₀ alkyl, optionally substituted alkenyl, optionally substituted alkynyl, optionally substituted carbocyclyl, optionally substituted heterocyclyl, optionally substituted aryl, and optionally substituted heteroaryl, or R^{L1b} is joined with the adjacent carbon or nitrogen or Oxygen atom to form an optionally substituted carbocyclic or heterocyclic ring, or two R^{L1b} groups are joined to form an optionally substituted carbocyclic or optionally substituted heterocyclic ring; and L² is a moiety derived from a crosslinking reagent capable of crosslinking the carrier and L¹.

In another embodiment, the linker comprises at least one sulfur atom, carboxylate group, amide group, carbamate group, carbonate group, thiocarbamate group, thiocarbonate group, thioether group, succinamide group, n-hydroxy succinamide group, or any combination thereof.

In another embodiment, the carrier is a protein, a lipid, a lipolized protein, a virus, a peptide, or a dendrimer of glycopeptides. In certain embodiments, the carrier is a peptide comprising a T cell epitope.

The carrier may be a protein selected from the group consisting of tetanus toxoid (TI), diphtheria toxoid (DT), diphtheria toxin cross-reacting material 197 (CRM197), fragment C of TT, Keyhole limpet hemocyanin (KLH), bovine serum albumin (BSA), protein D, outer-membrane protein (OMP) and pneumolysin.

In another embodiment, the carrier protein is selected from the group consisting of TT, DT and CRM197. In another embodiment, the carrier protein is CRM197, and the glycan conjugate is of the formula (III):

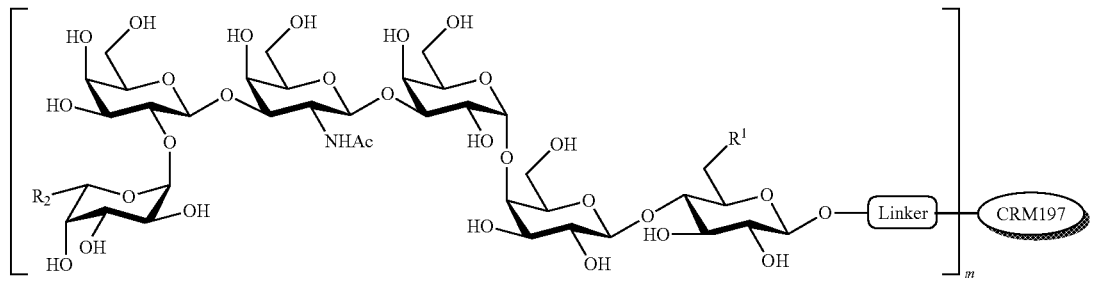

(III)

wherein
m is an integer from 1 to 38; and
provided that when R¹ is —OH, R² is not —CH₃; and when R² is —CH₃, R is not —OH.

The term "m" represents an integer from 1 to 38. In one embodiment of the invention, m is an integer from 1 to 30, or from 1 to 20. For example, m may be 1, 2, 3, 4, 6, 8, 10, 15, 20, 30, or 38.

In another aspect, the invention relates to a glycan conjugate mixture comprising at least two of the glycan conjugates as described herein. In certain embodiments, the average value of w in the glycan mixture may range from about 1.0 to about 38.0, or from about 1.0 to 10.0, or may be about 5.7, 4.9, 2.9, 2.8, or 3.1.

The immmunogenic compositions may optionally comprise an adjuvant. The adjuvant may be a glycolipid capable of binding a CD1d molecule on a dendritic cell. In certain embodiments, the adjuvant is C34, Gluco-C34, 7DW8-5, C17, C23, C30, α-galactoceramide, Aluminum salt, Squalene, MF59, or QS-21.

The immmunogenic composition comprises an immunogenically or a pharmaceutically effective amount of the glycan conjugate as aforementioned.

In another aspect, the invention relates to an immunogenic composition for use in eliciting an immune response against cancer in a subject. The cancer may be selected from the group consisting of brain cancer, lung cancer, breast cancer, oral cancer, esophagus cancer, stomach cancer, liver cancer, bile duct cancer, pancreas cancer, colon cancer, kidney cancer, bone cancer, skin cancer, cervix cancer, ovary cancer, and prostate cancer. Alternatively, the invention relates to use of an immunogenic composition as aforementioned in the manufacture of a medicament for treating a cancer patient to induce cancer cell cytotoxicity, elicit an immune response against the cancer, generate antibodies specifically binding to and/or neutralize one or more cancer cell surface antigens selected from the group consisting of Globo H, SSEA-3 and SSEA-4.

In one embodiment of the invention, the antibodies are predominantly IgG antibodies. The immmunogenic composition may be for use in inducing mainly IgG1, IgG2b, IgG2c and IgG3.

Further in another aspect, the invention relates to a monoclonal antibody raised against the immunogenic composition described herein.

In another aspect, the invention relates to a cancer vaccine comprising an immmunogenic composition as aforementioned and a pharmaceutically acceptable excipient. The cancer vaccine may comprise a single dose or multiple doses of glycan conjugates of the invention, a glycan conjugate mixture thereof, or immmunogenic compositions thereof. The cancer vaccines are used for treating or reducing the risk of cancers. The cancer vaccines may comprise packaging information describing the use or prescribing information for the subject or a health care professional. Such information may be required by a regulatory agency such as the U.S. Food and Drug Administration (FDA). The cancer vaccine may also optionally include a device for administration of the compound or composition, for example, a syringe for parenteral administration.

In another aspect, the present invention relates to methods for treating and/or reducing the risk for cancer in a subject comprising administering to a subject in need thereof a therapeutically effective amount of an immunogenic composition or a cancer vaccine as aforementioned.

The treatment results in reduction of tumor size, elimination of malignant cells, prevention of metastasis, prevention of relapse, reduction or killing of disseminated cancer, prolongation of survival and/or prolongation of time to tumor cancer progression.

The treatment may further comprise administering an additional therapy to said subject prior to, during or subsequent to said administering of the immunogenic composition or the cancer vaccine as aforementioned. The additional therapy may use a chemotherapeutic agent, or a radiation therapy.

In another aspect, the invention relates to a method of vaccinating a mammal such as a human patient against cancers, comprising administering to the mammal a pharmacologically effective amount of an immunogenic composition or a cancer vaccine as described herein. The immunogenic composition or the cancer vaccine as aforementioned may be administered subcutaneously.

The cancer include, but are not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer.

In another aspect, the invention relates to methods of synthesizing glycans as aforementioned.

In another aspect, the invention relates to a process for making an immunogenic composition or a cancer vaccine as aforementioned. In one embodiment of the invention, a process of preparing the immunogenic composition as aforementioned comprises the following steps:

(i) providing a compound of Formula (X):

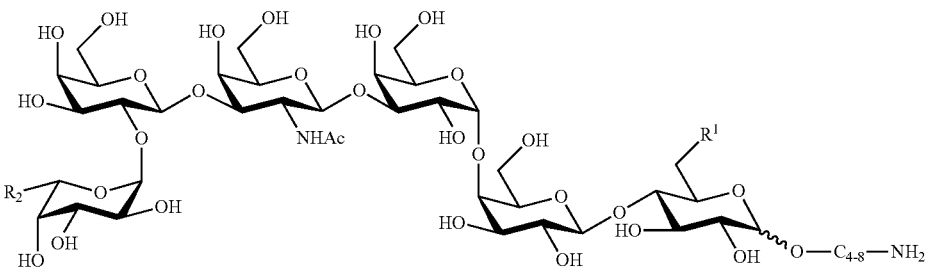

Formula (X)

wherein $R^1$ and $R^2$ $R^A R^B$ are as defined above in Formula (II); and provided that when $R^1$ is —OH, $R^2$ is not —CH$_3$, and when $R^2$ is —CH$_3$, $R^1$ is not —OH;

(ii) reacting the compound of Formula (X) with an amino-active bifunctional linker to afford a first reaction product; and (iii) reacting the first reaction product with a carrier protein to afford a glycan conjugate; and (iv) optionally admixing an adjuvant to afford the composition.

In one embodiment of the invention, the amino-active bifunctional linker is a dicarboxylic acid having 4 to 6 carbons.

The details of certain embodiments of the invention are set forth herein. Other features, objects, and advantages of the invention will be apparent from the detailed description, the figures, the examples, and the claims.

BRIEF DESCRIPTION OF THE DRAWINGS

FIGS. 1A-C are charts showing IgG antibody elicited by GH-derivatives DT conjugates against GH, Gb5 and SSEA4, respectively.

DEFINITIONS

Chemical Definitions

Figure 2:
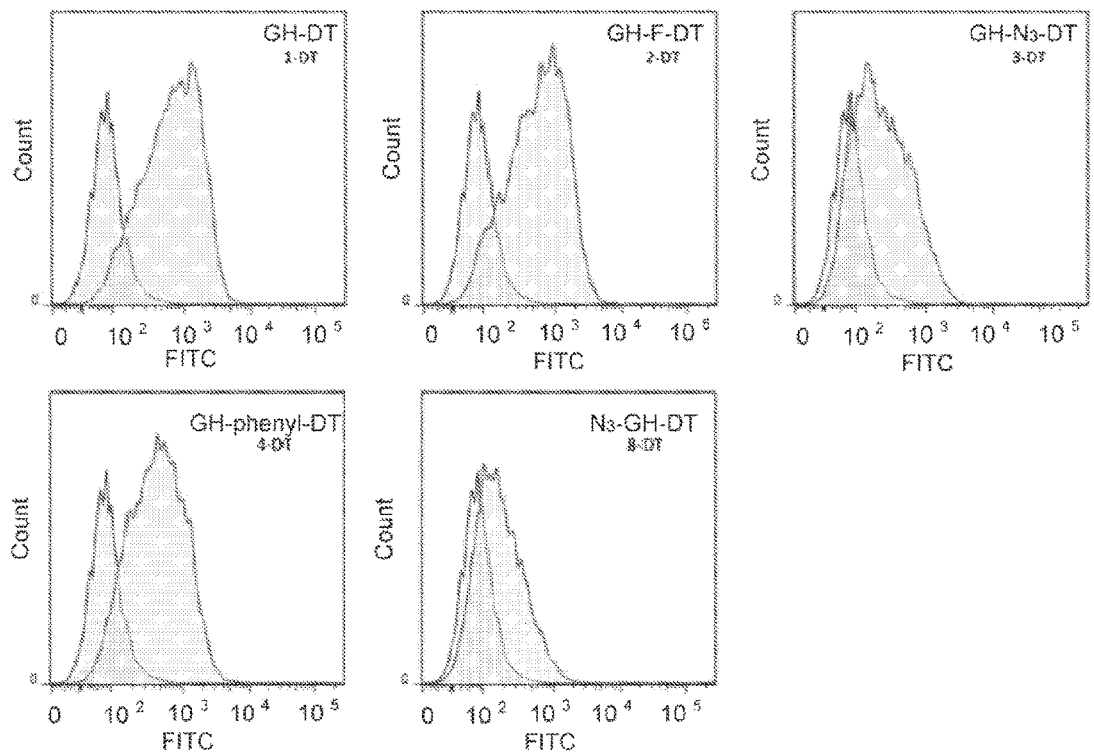
FIG. 2 shows that GH-derivatives DT conjugates-induced mouse antibodies recognize GH expressing tumor cell (MCF-7).

The chemical elements are identified in accordance with the Periodic Table of the Elements. CAS version, *Handbook* of *Chemistry and Physics*, 75th Ed., inside cover, and specific functional groups are generally defined as described therein. Additionally, general principles of organic chemistry and specific functional moieties and reactivity are described in Thomas Sorrell, *Organic Chemistry*, University Science Books, Sausalito, 1999; Smith and March, *March's Advanced Organic Chemistry*, 5th Edition, John Wiley & Sons. Inc., New York, 2001; Larock. *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms. e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., *Tetrahedron* 33:2725 (1977): Eliel, *Stereochemistry of Carbon Compounds* (McGraw-Hill, N Y, 1962); and Wilen, *Tables of Resolving Agents and Optical Resolutions* p. 268 (E. L. Eliel. Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 ("$C_{1-10}$ alkyl"), 1 to 9 ("$C_{1-9}$ alkyl"), 1 to 8 ("$C_{1-8}$ alkyl"), 1 to 7 ("$C_{1-7}$ alkyl"), 1 to 6 ("$C_{1-6}$ alkyl"), 1 to 5 ("$C_{1-5}$ alkyl"), 1 to 4 ("$C_{1-4}$ alkyl"), 1 to 3 ("$C_{1-3}$ alkyl"), 1 to 2 ("$C_{1-2}$ alkyl") carbon atoms. The alkyl group may also refer to 1 carbon atom ("$C_1$ alkyl").

In some embodiments, an alkyl group has 2 to 6 carbon atoms ("$C_{2-6}$ alkyl"). Examples of $C_{1-6}$ alkyl groups are methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having 2 to 20 carbon atoms, one or more carbon-carbon double bonds, and no triple bonds ("$C_{2-20}$ alkenyl"). An alkenyl group may have 2 to 10 ("$C_{2-10}$ alkenyl"), 2 to 9 ("$C_{2-9}$ alkenyl"), 2 to 8 ("$C_{2-8}$ alkenyl"), 2 to 7 ("$C_{2-7}$ alkenyl"), 2 to 6 ("$C_{2-6}$ alkenyl"), 2 to 5 ("$C_{2-5}$ alkenyl"), 2 to 4 ("$C_{2-4}$ alkenyl"), 2 to 3 ("$C_{2-3}$ alkenyl"), or 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups are ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include $C_{2-4}$ alkenyl, pentenyl ($C_5$), pentadienyl ($C_5$), hexenyl ($C_6$), heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. For example, the alkenyl group may be unsubstituted $C_{2-10}$ alkenyl, or substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 ("$C_{2-10}$ alkynyl"), 2 to 9 ("$C_{2-9}$ alkynyl"), 2 to 8 ("$C_{2-4}$ alkynyl"), 2 to 7 ("$C_{2-7}$ alkynyl"), 2 to 6 ("$C_{2-4}$ alkynyl"), 2 to 5 ("($C_{2-5}$ alkynyl"), 2 to 4 ("$C_{2-4}$ alkynyl"), 2 to 3 ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups, pentynyl ($C_5$), hexynyl ($C_6$), heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. For example, the alkynyl group may be unsubstituted $C_{2-10}$ alkynyl, or substituted $C_{2-10}$ alkynyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring is fused with one or more carbocyclyl groups wherein the point of attachment is either on the carbocyclyl or heterocyclic ring, or ring systems wherein the heterocyclic ring is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. For example, the heterocyclyl group may be unsubstituted 3-10 membered heterocyclyl, or substituted 3-10 membered heterocyclyl.

"Aryl" refers to a radical of a monocyclic or polycyclic (e.g., bicyclic or tricyclic) 4n+2 aromatic ring system (e.g., having 6, 10, or 14π electrons shared in a cyclic array)

having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl), ten ring carbon atoms ("$C_{10}$ aryl"; e.g., naphthyl such as 1-naphthyl and 2-naphthyl), or fourteen ring carbon atoms ("$C_{14}$ aryl"; e.g., anthracyl). "Aryl" also includes ring systems wherein the aryl ring is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. For example, the aryl group may be unsubstituted $C_{6-14}$ aryl, or substituted $C_{6-14}$ aryl.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

The term "alkoxy" or "alkyloxy" refers to an —O-alkyl radical, wherein alkyl is optionally substituted alkyl. Examples of alkoxy include, but are not limited to, methoxy, ethoxy, n-propoxy, isopropoxy, n-butoxy, iso-butoxy, sec-butoxy, and tert-butoxy.

The term "aryloxy" refers to an —O-aryl, wherein aryl is optionally substituted aryl.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl. "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)$R^{aa}$, —C(=NR$^{bb}$)OR$^{aa}$, —C(=NR$^{bb}$) N($R^{bb}$)$_2$, —C(=O)NR$^{bb}$SO$_2R^{aa}$, —C(=S)N($R^{bb}$)$_2$, —C(=)SR$^{aa}$, and —C(=S)SR$^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2R^{aa}$, —SO$_2R^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2R^{aa}$, —P(=O) (R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O) SR$^{aa}$, —C(=O)R$^{aa}$, —CO$_2R^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2R^{aa}$, —Si(R$^{aa}$)$_3$, —P(R$^{cc}$)$_2$, —P(R$^{cc}$)$_3$, —P(=O)$_2R^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition. John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Other Definitions

The singular forms "a", "an", and "the" include plural reference unless the context clearly dictates otherwise. The terms "a" (or "an"), "one or more" and "at least one" can be used interchangeably herein. The terms "comprising", "including", and "having" are interchangeable.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook. Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss. Inc., 1987); Immobilized Cells And Enzymes (IRl. Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Set or Asn-X-Thr sequence, where X is any amino acid except praline.

The term "antigen" is defined as any substance capable of eliciting an immune response.

The term "immunogenicity" refers to the ability of an immunogen, antigen, or vaccine to stimulate an immune response.

The term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids, including α-GalCer analogs such as C34.

The term "epitope" is defined as the parts of an antigen molecule which contact the antigen binding site of an antibody or a T cell receptor.

The term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

The term "antigen specific" refers to a property of a cell population such that supply of a particular antigen, or a fragment of the antigen, results in specific cell proliferation.

The term "specifically binding," refers to the interaction between binding pairs (e.g., an antibody and an antigen). In various instances, specifically binding can be embodied by an affinity constant of about 10 moles/liter, about $10^{-7}$ moles/liter, or about $10^{-8}$ moles/liter, or less.

The term "flow cytometry" or "FACS" means a technique for examining the physical and chemical properties of particles or cells suspended in a stream of fluid, through optical and electronic detection devices.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

DETAILED DESCRIPTION OF THE INVENTION

The present invention relates to the surprising finding that the modified Globo H derivative antigens conjugated with the carrier protein diphtheria toxoid cross-reactive material (CRM197), and combined with a glycolipid C34 as an adjuvant elicit strong IgG immune response to specifically recognize Globo H (GH), Gb5 and SSEA4. In some embodiments, the modification of Globo H comprises a fluoro, an azido or an O-phenyl group at the C-6 position of reducing end glucose of Globo H. In some embodiments, the modification of Globo H comprises an azido group at the C-6 position of the non-reducing end fucose. The antibodies induced by theses vaccines were shown to recognize GH expressing tumor cells (MCF-7) and mediate the complement-dependent cell cytotoxicity against tumor cells. The invention provides a new approach to cancer vaccine development.

Described herein are Globo H derivatives that each has modification at the reducing and/or non-reducing end. It was unexpectedly discovered that such Globo H derivatives can elicit a stronger immune response (e.g., induction of IgG antibodies against Globo H, Gb5, and SSEA4) as compared to the native Globo H.

Compounds

The present invention features novel compounds having an modified carbohydrate antigen (Globo H), and glycan conjugates comprising such, and immmunogenic compositions and vaccines thereof.

In one aspect, the invention relates to a compound of formula (I):

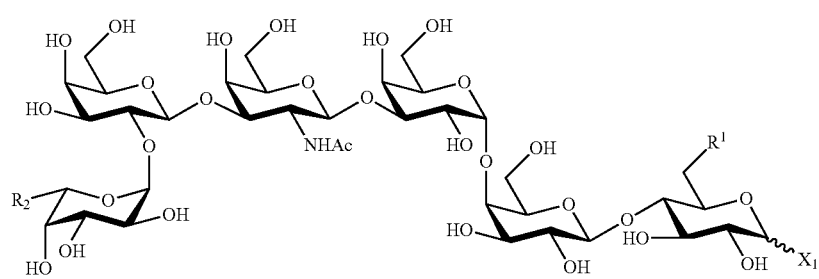

(I)

or a salt thereof,
wherein:
X$_1$ is —OR or —SR, wherein R is hydrogen, an oxygen or a sulfur protecting group, optionally substituted C$_{1-10}$ alkyl, optionally substituted aryl, optionally substituted acyl, or optionally substituted imidoyl;
R$^1$ and R$^2$ is independently selected from hydrogen, halogen, optionally substituted alkyl, optionally substituted alkenyl, optionally substituted alkynyl, optionally substituted heterocyclyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;
R$^A$ is independently selected from hydrogen, optionally substituted alkyl, optionally substituted alkenyl, optionally substituted alkynyl, optionally substituted heterocyclyl, and optionally substituted aryl;
R$^B$ is independently selected from hydrogen, optionally substituted alkyl, optionally substituted alkenyl, optionally substituted alkynyl, optionally substituted heterocyclyl, and optionally substituted aryl; and
provided that when R$^1$ is —OH, R$^2$ is not —CH$_3$; and when R$^2$ is —CH$_3$, R$^1$ is not —OH.

In one embodiment of the invention, X$_1$ is in an alpha configuration. In another embodiment of the invention, X$_1$ is in a beta configuration.

In another embodiment of the invention, X$_1$ is selected from the group consisting of —OR$^A$, —OH, and —O(protecting group). In another embodiment of the invention, X$_1$ is —OR$^A$, wherein R$^A$ is unsubstituted C$_{1-10}$ alkyl, unsubstituted aryl, unsubstituted acyl, or unsubstituted imidoyl, or wherein R$^A$ is substituted C$_{1-10}$ alkyl, substituted aryl, substituted acyl, or substituted imidoyl.

In another embodiment of the invention, X$_1$ is —SR$^A$. In another embodiment of the invention. X$_1$ is selected from the group consisting of —SH, and —S(protecting group), and —SCH$_3$. In another embodiment of the invention, X$_1$ is —SR$^A$, wherein R$^A$ is unsubstituted C$_{1-10}$ alkyl, unsubstituted aryl, unsubstituted acyl, unsubstituted imidoyl; or wherein R$^A$ is substituted C$_{1-10}$ alkyl, substituted aryl, substituted acyl, or substituted imidoyl.

In another embodiment of the invention, X$_1$ is C$_{1-10}$ alkoxy, C$_{1-3}$ alkoxy, or methoxy. In another embodiment of the invention, X$_1$ is alpha-methoxy.

In another embodiment of the invention, X$_1$ is selected from the group consisting of alpha-thiomethyl, beta-thiomethyl, alpha-thiocresyl, beta-thiocresyl, alpha-t-butyldiphenylsilyloxy, beta-t-butyldiphenylsilyloxy, and alpha-methoxy.

In another embodiment of the invention, R$^1$ is —N$_3$ or —N(R$^W$)$_2$, wherein each R$^W$ is independently hydrogen or a nitrogen protecting group. For example, R$^1$ may be —NH$_2$.

In another embodiment of the invention, R$^1$ is —NHR$^W$ or —N(R$^W$)$_2$, wherein R$^W$ is a nitrogen protecting group. In certain embodiments, R$^1$ is selected from the group consisting of —N$_3$, —NH(Cbz), —NH(Boc), —NH(Fmoc). —NHC(O)CCl$_3$, —NHC(O)CH$_3$, and —N(C(O)CH$_3$)$_2$.

In another embodiment of the invention. R$^2$ is —N$_3$ or —N(R$^W$)$_2$, wherein each R$^W$ is independently hydrogen or a nitrogen protecting group. In another embodiment of the invention, $R^2$ is —$NH_2$, —$NHR^W$, or —$N(R^W)_2$, wherein $R^W$ is a nitrogen protecting group. In another embodiment of the invention, $R^2$ is selected from the group consisting of —$N_3$, —NH(Cbz), —NH(Boc), —NH(Fmoc), —NHC(O)CCl$_3$, —NHC(O)CH$_3$, and —N(C(O)CH$_3$)$_2$.

In another embodiment of the invention, $R^1$ and $R^2$ are the same.

In another embodiment of the invention, $R^1$ is —OH. In another embodiment of the invention, $R^1$ is —OH and $R^2$ is —CH$_2$F, —CH$_2$N$_3$, CH$_2$NO$_2$, —CH$_2$OH, or —C≡CH.

In another embodiment of the invention, $R^1$ is —F and $R^2$ is —CH$_3$, or $R^1$ is —N$_3$ and $R^2$ is —CH$_3$, or $R^1$ is —NO$_2$ and $R^2$ is —CH$_3$.

In another embodiment of the invention, $R^1$ is

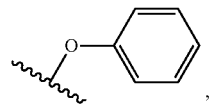

and $R^2$ is —CH$_3$, or $R^1$ is and $R^2$ is —CH$_3$.

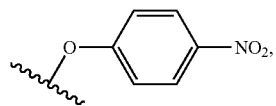

Exemplary compounds of formula (1) include, but are not limited to,

2

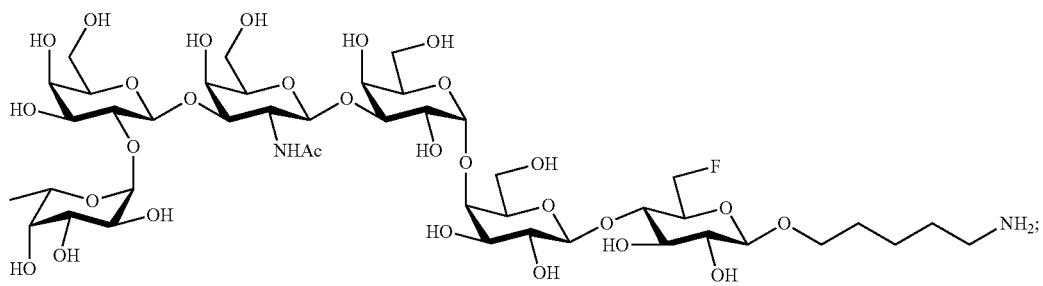

3

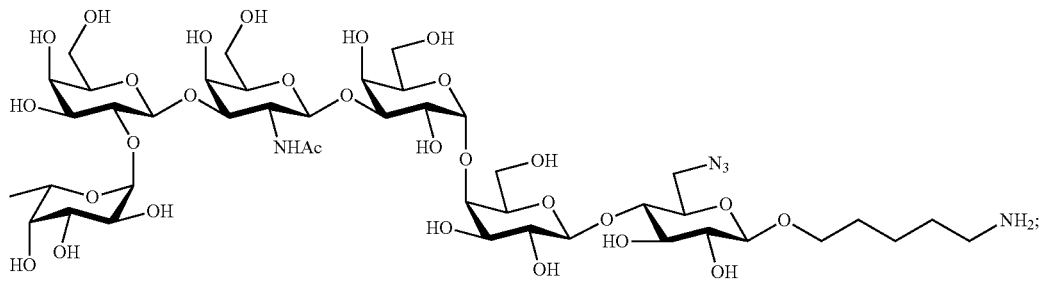

4

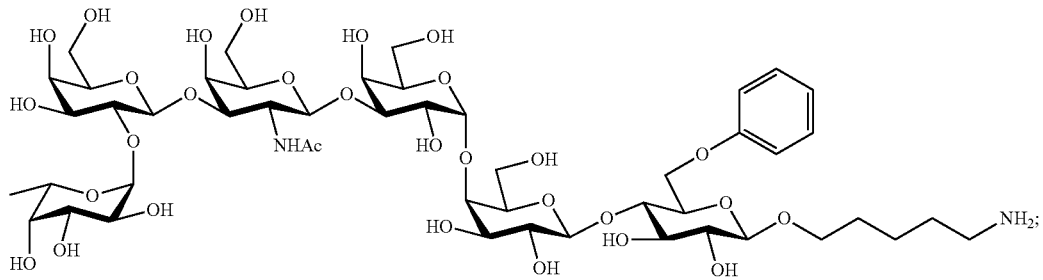

5

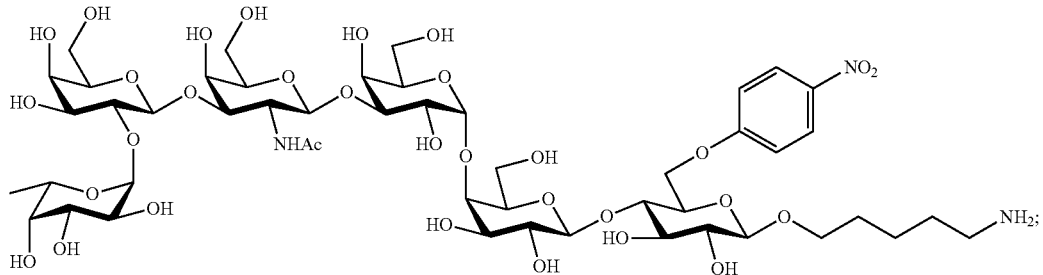

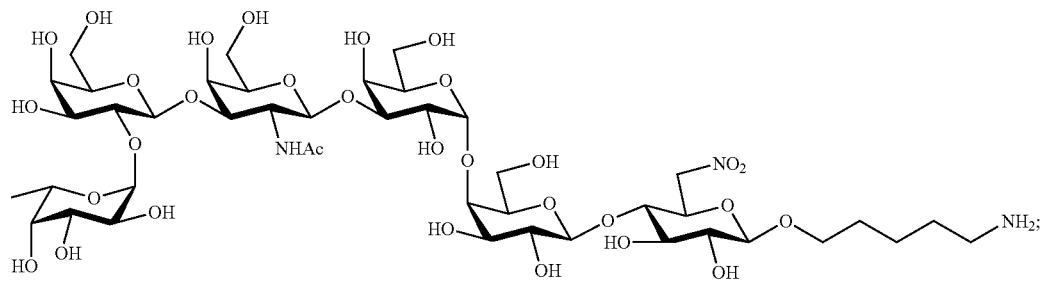

6

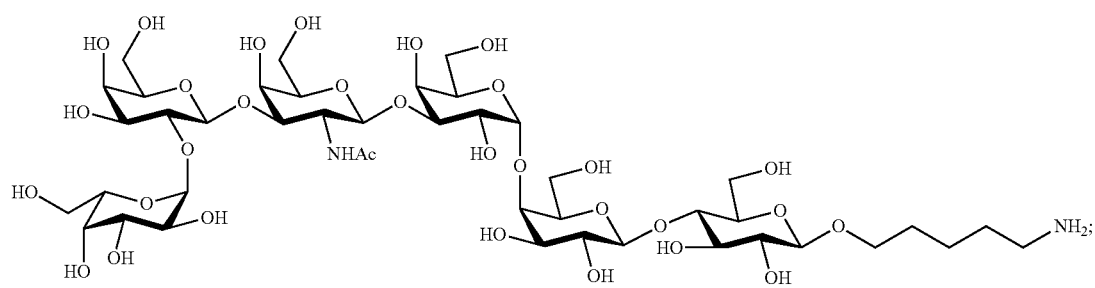

7

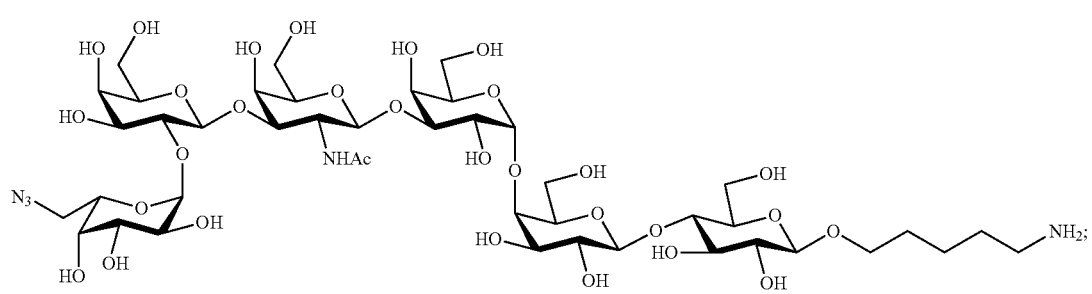

8

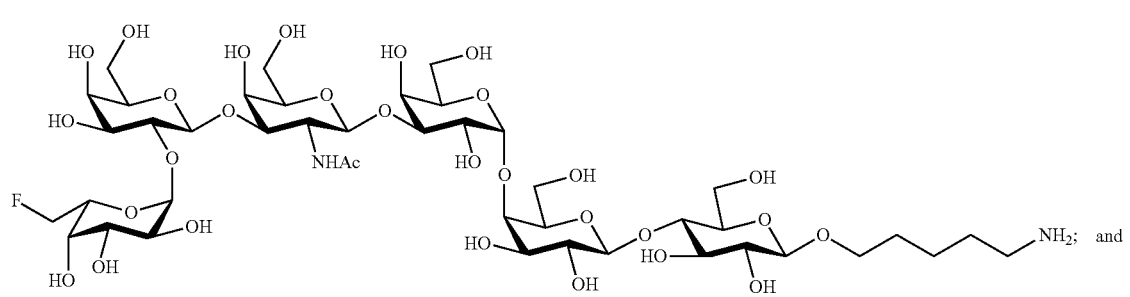

9

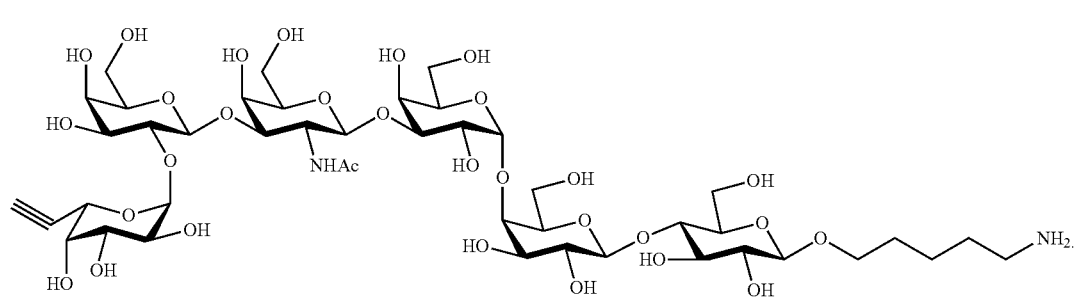

10

The Globo H derivatives can be synthesized using procedures known in the art or described herein. Also see US20140051127.

Immunogenic Compositions

In another aspect, the invention relates to an immunogenic composition, comprising (a) a glycan conjugate comprising at least one glycan (i.e., one or more glycans) with a linker and a carrier, the at least one glycan being conjugated to the carrier through the linker; and (b) optionally an adjuvant, wherein the at least one glycan with the linker has a chemical structure of formula (II):

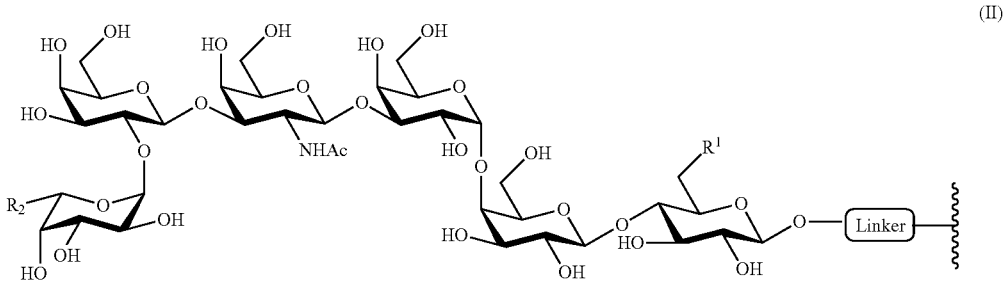

(II)

wherein $R^1$ and $R^2$ are as described above.

In one embodiment of the invention, the linker is a hetero- or homo-bifunctional linker.

In another embodiment of the invention, the linker comprises at least one sulfur atom, carboxylate group, amide group, carbamate group, carbonate group, thiocarbamate group, thiocarbonate group, thioether group, succinamide group, n-hydroxy succinamide group, or any combination thereof.

In another embodiment, the linker is -$L^1$-$L^2$-, wherein $L^1$ is a bond, —O—, —S—, —$NR^{L1a}$—, —C(=O)—, —$NR^{L1a}$C(=O)—, —$NR^{L1a}$C(=O)O—, —C(=O)$NR^{L1a}$—, —OC(=O)$NR^{L1a}$—, —SC(=O)—, —C(=O)S—, —OC(=O)—, —C(=O)O—, —$NR^{L1a}$C(=S)—, —C(=S)$NR^{L1a}$—, trans-$CR^{L1b}$=$CR^{L1b}$—, cis-$CR^{L1b}$=$CR^{L1b}$—, —C≡C—, —OC($R^{L1b}$)$_2$—, —C($R^{L1b}$)$_2$O—, —$NR^{L1a}$C($R^{L1b}$)$_2$—, —C($R^{L1b}$)$_2$$NR^{L1a}$—, —SC($R^{L1b}$)$_2$—, —C($R^{L1b}$)$_2$S—, —S(=O)$_2$O—, —OS(=O)$_2$—, —S(=O)$NR^{L1a}$—, —$NR^{L1a}$S(=O)$_2$—, or an optionally substituted $C_{1-20}$ hydrocarbon chain, optionally wherein one or more carbon units of the hydrocarbon chain is replaced with —O—, —S—, —$NR^{L1a}$—, —C(=O)—, —$NR^{L1a}$C(=O)—, —$NR^{L1a}$C(=O)O—, —C(=O)$NR^{L1a}$—, —OC(=O)$NR^{L1a}$—, —SC(=O)—, —C(=O)S—, —OC(=O)—, —C(=O)O—, —$NR^{L1a}$C(=S)—, —C(=S)$NR^{L1a}$—, trans-$CR^{L1b}$=$CR^{L1b}$—, cis-$CR^{L1b}$=$CR^{L1b}$—, —C≡C—, —S(=O)$_2$O—, —OS(=O)$_2$—, —S(=O)$_2$$NR^{L1a}$—, or —$NR^{L1a}$S(=O)$_2$—, wherein $R^{L1a}$ is hydrogen, optionally substituted $C_{1-6}$ alkyl, or a nitrogen protecting group, or $R^{L1a}$ is joined with the adjacent carbon atom to form an optionally substituted heterocyclic ring, and wherein each occurrence of $R^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or $R^{L1b}$ is joined with the adjacent carbon or nitrogen or oxygen atom to form an optionally substituted carbocyclic or heterocyclic ring, or two $R^{L1b}$ groups are joined to form an optionally substituted carbocyclic or optionally substituted heterocyclic ring; and $L^2$ is a moiety derived from a crosslinking reagent capable of crosslinking the carrier and $L^1$.

The carrier may be a protein, a lipid, a lipolized protein, a virus, a peptide, or a dendrimer of glycopeptides. In certain embodiments, the carrier is a peptide comprising a T cell epitope.

Examples of carrier proteins are tetanus toxoid (TT), diphtheria toxoid (DT), diphtheria toxin cross-reacting material 197 (CRM197), fragment C of TT. Keyhole limpet hemocyanin (KLH), bovine serum albumin (BSA), protein D, outer-membrane protein (OMP) and pneumolysin, diphtheria toxin cross-reacting material 197 (CRM197) or other DT point mutants, such as CRM176. CRM228, CRM45 (Uchida et al J. Biol. Chem. 218; 3838-3844, 1973); CRM 9. CRM 45, CRM102, CRM 103 and CRM107 and other mutations described in the art.

In another embodiment of the invention, the glycan conjugate is of the formula (IV-a) or (IV-b):

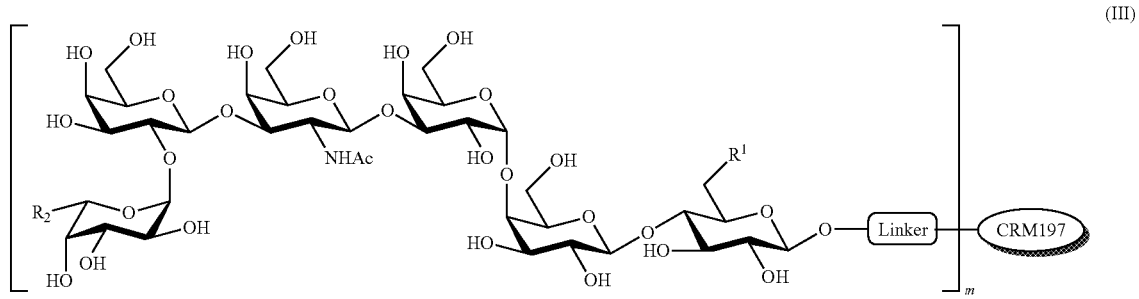

(III)

wherein m is an integer from 1 to 40.

In another embodiment of the invention, m is an integer from 1 to 38, or from 1 to 20 inclusive. In another embodiment of the invention, m is 1, 2, 4, 6, 8, 10, 15, 20, 30, or 38.

In another aspect, the invention relates to a glycan conjugate mixture comprising at least two of the glycan conjugates as aforementioned.

In another embodiment of the invention, Globo H derivative may be conjugated to a carrier through a linker to generate a glycan conjugate. Each conjugate can include one or more molecules (e.g., 1-40, 1-20, 1-25, 1-30, 5-20, 5-25, 5-30, or 5-35) of the same or different Globo H derivatives. Procedures for generating glycan conjugates are known in the art and described below. Also see U.S. Pat. No. 8,268,969.

The immmunogenic compositions described herein may comprise an immmunogenically effective amount of a glycan conjugate of the invention.

The compounds of the invention can be synthesized using procedures known in the art or described herein. Also see US20140051127.

The immmunogenic composition of the invention may comprise one or more adjuvants.

Suitable adjuvants are known in the art (e.g., C34, 7DW8-5, C17, C23, Aluminum salt, Squalene, MF59, and QS-21).

The term "alum adjuvant" refers to an aluminum salt with immune adjuvant activity. This agent adsorbs and precipitates protein antigens in solution; the resulting precipitate improves vaccine immunogenicity by facilitating the slow release of antigen from the vaccine depot formed at the site of inoculation.

The term "immunologic adjuvant" refers to a substance used in conjunction with an immunogen which enhances or modifies the immune response to the immunogen. The α-GalCer analogs of the present disclosure are used as immunologic adjuvants to modify or augment the effects of a vaccine by stimulating the immune system of a patient who is administered the vaccine to respond to the vaccine more vigorously. In an exemplary implementation, the analog C34 is used as an adjuvant. The structures of C34 and other alpha-galactosyl ceramide analogs and their use as adjuvants are disclosed in U.S. Pat. No. 7,928,077.

The term "glycolipid" refers to a carbohydrate-attached lipid that serves as a marker for cellular recognition.

The glycolipids C34, C23 and 7DW8-5 have the following structures:

glycan conjugate mixture thereof, or immmunogenic compositions thereof. It may be used for treating or reducing the risk of cancers. It may also include packaging information describing the use or prescribing information for the subject or a health care professional. Such information may be required by a regulatory agency such as the U.S. Food and Drug Administration (FDA). It may also optionally include a device for administration of the compound or composition, for example, a syringe for parenteral administration.

Pharmaceutical Formulations

The immune composition is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent administrations. The dosage of the vaccine may also depend on the route of administration and varies according to the size of the host.

The immunogenic composition of the invention can also be used to generate antibodies in animals for production of antibodies, which can be used in both cancer treatment and diagnosis. Methods of making monoclonal and polyclonal antibodies and fragments thereof in animals (e.g., mouse,

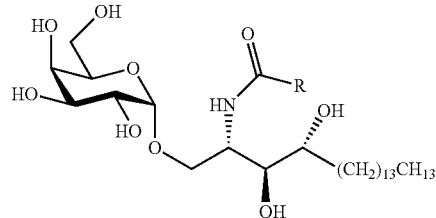

C1, R = (CH$_2$)$_{24}$CH$_3$
C23, R = (CH$_2$)$_7$PhF
C34, R = (CH$_2$)$_{10}$PhOPhF
7DW8-5, R = (CH$_2$)$_{10}$PhF

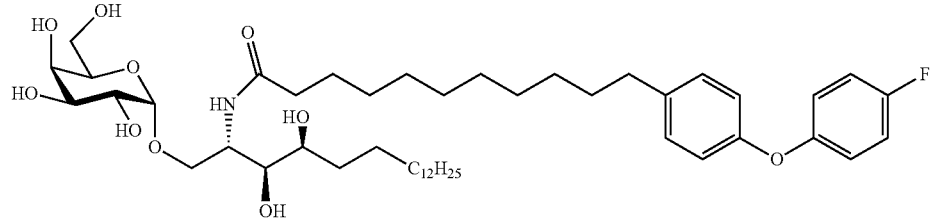

C34

The immunogenic composition may further comprise a pharmaceutically acceptable excipient. The immmunogenic compositions as aforementioned may comprise an pharmaceutically effective amount of a glycan conjugate of the invention.

In another aspect, the invention relates to a cancer vaccine comprising an immmunogenic composition as aforementioned and a pharmaceutically acceptable excipient.

The cancer vaccines of the invention may include a single dose or multiple doses of the inventive glycan conjugates, a rabbit, goat, sheep, or horse) are well known in the art. See, for example, Harlow and Lane, (1988) *Antibodies: A Laboratory Manual*, Cold Spring Harbor Laboratory, New York. The term "antibody" includes intact immunoglobulin molecules as well as fragments thereof, such as Fab, F(ab')$_2$, Fv, scFv (single chain antibody), and dAb (domain antibody; Ward, et. al. (1989) *Nature*, 341, 544).

The compositions disclosed herein may be included in a pharmaceutical composition together with additional active agents, carriers, vehicles, excipients, or auxiliary agents identifiable by a person skilled in the art upon reading of the present disclosure.

The pharmaceutical compositions preferably comprise at least one pharmaceutically acceptable carrier. In such pharmaceutical compositions, the compositions disclosed herein form the "active compound," also referred to as the "active agent." A pharmaceutically acceptable carrier includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Clinical Applications

The invention relates to glycan conjugates, immunogenic compositions or vaccines useful for the treatment of a proliferative disease such as cancer (e.g. lung cancer, large bowel cancer, pancreas cancer, biliary tract cancer, or endometrial cancer), benign neoplasm, or angiogenesis in a subject.

The immunogenic compositions or vaccines of the invention may also be used to generate antibodies in human or animals for production of antibodies, which may be used in both cancer treatment and diagnosis. They may also be used to generate antibodies for production of Gloo H, SSEA-3 and/or SSEA-4 antibodies. Methods of making monoclonal and polyclonal antibodies and fragments thereof in human and/or animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab').sub.2, Fv, scFv (single chain antibody), and dAb (domain antibody: Ward, et. al. (1989) Nature, 341, 544).

The glycan conjugates, immunogenic compositions or vaccines of the invention may be used for treating, or diagnosing cancer, which includes, but is not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g. B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM). a.k.a. myclofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the provided glycan conjugates, immunogenic compositions or vaccines are useful for treating brain cancer, lung cancer, breast cancer, oral cancer, esophagus cancer, stomach cancer, liver cancer, bile duct cancer, pancreas cancer, colon cancer, kidney cancer, bone cancer, skin cancer, cervix cancer, ovary cancer, and prostate cancer.

An effective amount of any of the glycan conjugates or immunogenic compositions or vaccines of the invention may be administered to a subject in need of the treatment via a suitable route, as aforementioned. The subject, such as a human, may be a patient having cancer, suspected of having cancer, or susceptible to cancer. The effective amount may be effective in eliciting immune responses specific to the glycan moiety in the conjugate or composition, or sufficient to elicit immune responses leading to the inhibition of cancer growth and/or reduction of tumor mass, or effective in delaying the onset of the target cancer or reducing the risk for developing the cancer. The exact amount required will vary from subject to subject, depending, for example, on species, age, and general condition of a subject, severity of the side effects or disorder, identity of the particular compound(s), mode of administration, and the like. The desired dosage may be delivered three times a day, two times a day, once a day, every other day, every third day, every week, every two weeks, every three weeks, or every four weeks. It may be delivered using multiple administrations (e.g., two, three, four, five, six, seven, eight, nine, ten, eleven, twelve, thirteen, fourteen, or more administrations).

An effective amount of glycan conjugates, immunogenic compositions or vaccines of the invention for to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

The glycan conjugates, immunogenic compositions or vaccines of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of the glycan conjugates, immunogenic compositions or vaccines of the invention to an adult. The amount to be administered to a child or an adolescent may be determined by a medical practitioner or person skilled in the art and may be lower or the same as that administered to an adult.

The glycan conjugates, immunogenic compositions or vaccines of the invention may be administered in combination with one or more additional therapeutically active agents. They may be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The glycan conjugates, immunogenic compositions or vaccines of the invention may be administered concurrently with, prior to, or subsequent to, one or more additional therapeutically active agents. In general, each agent will be administered at a dose and/or on a time schedule determined for that agent. The additional therapeutically active agent utilized in the combination may be administered together in a single composition or administered separately in different compositions. The particular combination to employ in a regimen will take into account compatibility of the inventive compound with the additional therapeutically active agent and/or the desired therapeutic effect to be achieved. It is expected that additional therapeutically active agents in the combination therapy are utilized at levels that do not exceed the levels at which they are utilized individually. In some cases, the levels utilized in combination may be lower than those utilized individually.

The glycan conjugate, immunogenic composition or vaccine of the invention may be administered in combination with one or more additional pharmaceutical agents such as an anti-cancer agent, which includes a biotherapeutic anti-cancer agent and chemotherapeutic agents.

Biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel. Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AGO 13736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA@, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

The subject being treated is a mammal such as a human, or a domesticated animal such as a dog, cat, cow, pig, horse, sheep, or goat. The subject may also be a non-human transgenic animal such as a transgenic mouse or transgenic pig.

EXAMPLES

The following examples are provided to demonstrate preferred embodiments of the invention. Those skilled in the art should, in light of the present disclosure, appreciate many changes may be made in the specific embodiments disclosed and still obtain a like or similar result without departing from the spirit and scope of the invention.

Example 1: Syntheses of GH-Lac Derivatives

Scheme 1 shows synthesis of GH-Lac derivatives 2-6. Enzymes: GalK, galactokinase; AtUSP, UDP-sugar pyrophosphorylase; LgtC, α1,4-galactosyl-transferase; PK, pyruvate kinase; PPA, inorganic pyrophosphatase; GlmU, N-acetyl glucosamine-1-phosphate uridyltransferase; NahK, N-acetylhexosamine kinase; LgtD, β1,3-N-acetylgalactosaminyltransferase; FKP, bifunctional fucokinase/GDP-L-fucose pyrophosphorylase. FutC, α-1,2-fucosyltransferase.

Scheme 1
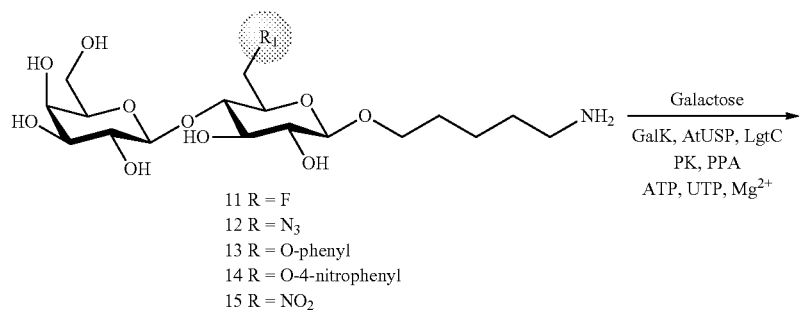
11 R = F
12 R = N₃
13 R = O-phenyl
14 R = O-4-nitrophenyl
15 R = NO₂
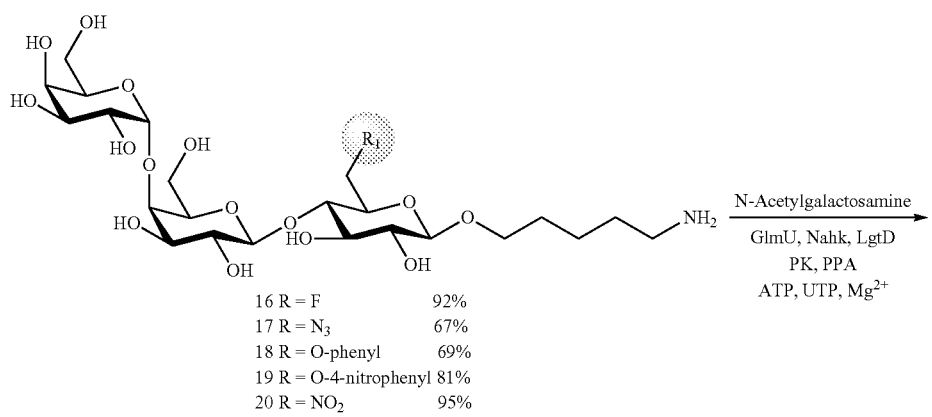
| | | |
|---|---|---|
| 16 R = F | 92% |
| 17 R = N₃ | 67% |
| 18 R = O-phenyl | 69% |
| 19 R = O-4-nitrophenyl | 81% |
| 20 R = NO₂ | 95% |
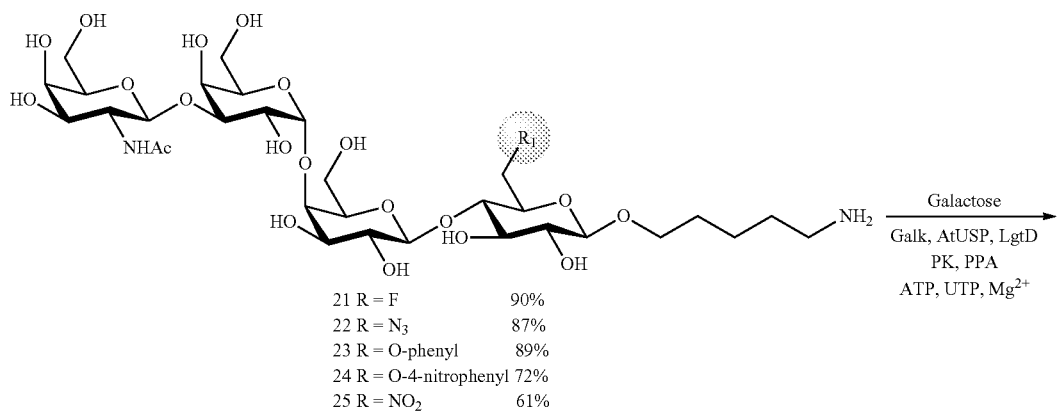
| | | |
|---|---|---|
| 21 R = F | 90% |
| 22 R = N₃ | 87% |
| 23 R = O-phenyl | 89% |
| 24 R = O-4-nitrophenyl | 72% |
| 25 R = NO₂ | 61% |

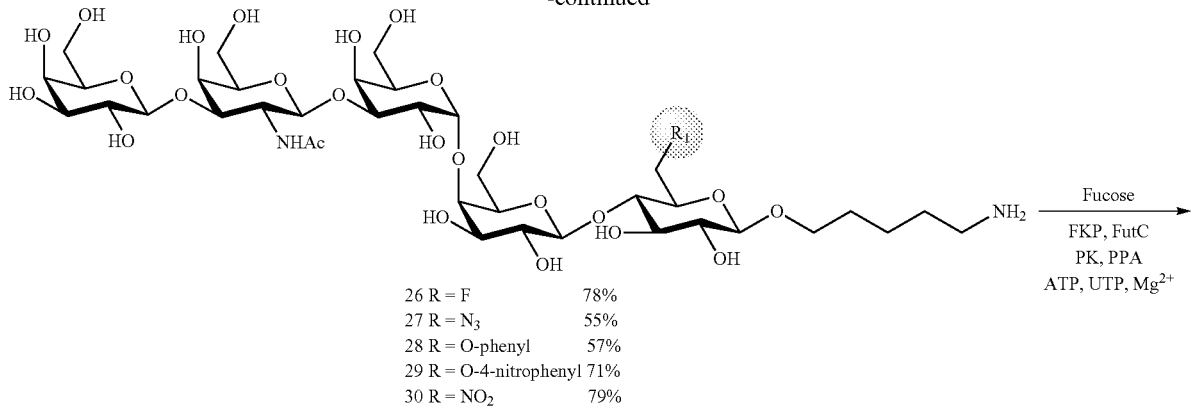

| | | |
|---|---|---|
| 26 R = F | 78% | |
| 27 R = N₃ | 55% | |
| 28 R = O-phenyl | 57% | |
| 29 R = O-4-nitrophenyl | 71% | |
| 30 R = NO₂ | 79% | |

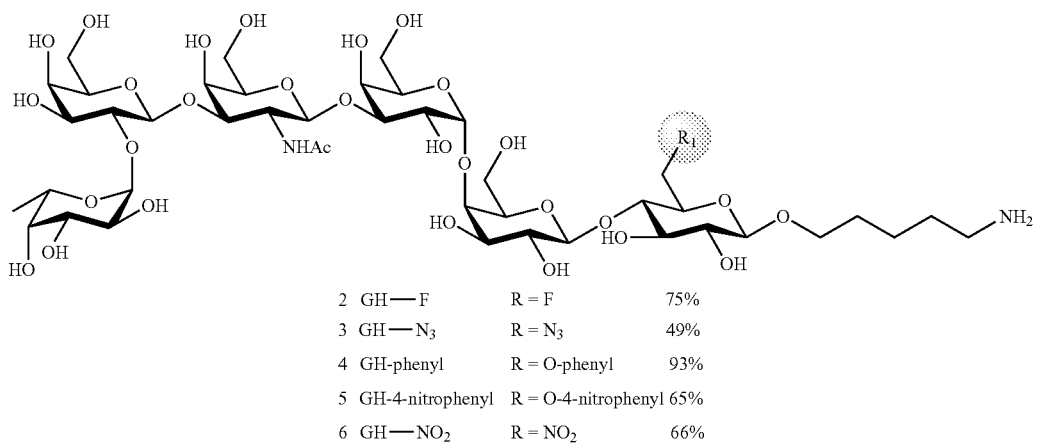

| | | | |
|---|---|---|---|
| 2 | GH—F | R = F | 75% |
| 3 | GH—N₃ | R = N₃ | 49% |
| 4 | GH-phenyl | R = O-phenyl | 93% |
| 5 | GH-4-nitrophenyl | R = O-4-nitrophenyl | 65% |
| 6 | GH—NO₂ | R = NO₂ | 66% |

The synthesis of the GH-Lac derivatives 2-6 (reducing end derivatives) (Scheme 1) was started from the Lac derivatives 11-15 following the enzymatic procedure described previously.[15a] The Gb3-Lac derivatives 16-20 were synthesized with galactose, α1,4-galactosyltransferase (LgtC) and the UDP-Gal regeneration system including UDP-sugar pyrophosphorylase (AtUSP), galactokinase (GalK), pyruvate kinase (PK) and inorganic pyrophosphatase (PPA). LgtC has been carefully characterized and utilized in the synthesis of α-(1→4)-galactosylated derivatives.[31] Here. LgtC was also found to exhibit good activities to the Lac derivatives (11-15). The yields of Gb3-F 16, Gb3-phenylNO₂ 19 and Gb3-NO₂ 20 were 92, 81 and 95%, respectively, and the yields of Gb3-N₃ 17 and Gb3-phenyl 18 were 67 and 69%, respectively.

The Gb3-Lac derivatives 16-20 were used as acceptors for the synthesis of the Gb4 derivatives 21-25 using galactosamine, β1,3-N-acetylgalactosaminyltransferase (LgtD) and the UDP-GalNac regeneration system including N-acetylhexosamine kinase (NahK), N-acetyl glucosamine-1-phosphate uridyltransferase (GlmU), pyruvate kinase (PK) and inorganic pyrophosphatase (PPA).[15a] After overexpression and biochemical characterization,[32] LgtD was used to glycosylate Gb3-F16, Gb3-N₃ 17 and Gb3-phenyl 18 as acceptors to obtain Gb4-F 21, Gb4-N₃ 22 and Gb4-phenyl 23 in 90, 87 and 89% yields, respectively. From Gb3-phenylNO₂ 19 and Gb3-NO₂ 20, Gb4-phenylNO₂ 24 and Gb4-NO₂, 25 were obtained in 72 and 61% yields, respectively.

The Gb5-Lac derivatives 26-30 were obtained from the Gb4 derivatives 21-25 and galactose using β1,3-N-acetylgalactosaminyltransferase (LgtD) and the UDP-gal regeneration system as described before.[15a] Gb5-F 26, GB5-N₃ 27, Gb5-phenyl 28, Gb5-phenylNO₂ 29 and Gb5 NO₂ 30 were obtained in 55% to 79% yields.

The GH-Lac derivatives 2-6 were synthesized from the Gb5-Lac derivatives 26-30 using α-1,2-fucosyltransferase (FutC), bifunctional fucokinase/GDP-L-fucose pyrophosphorylase (FKP), pyrophosphatase (PPA), pyruvate kinase (PK) and Fucose.[15a] GH-F 2 and GH-phenyl 4 were prepared from acceptors Gb5-F 26 and Gb5-phenyl 28 in 75 and 93% yields, respectively. Using Gb5-N₃ 27, Gb5-phenylNO₂ 29 and Gb5-NO, 30 as acceptors GH-N₃ 3, GH-phenylNO₂ 5 and GH-NO₂ 6 were obtained in 49, 65 and 66% yields, respectively.

Example 2; Syntheses of GH-Fuc Derivatives

Scheme 2 shows chemoenzymatic synthesis of GH-Fuc derivatives. Reaction condition: FKP, Fut C, PPA, PK, $Mg^{2+}$, ATP, GTP.

Scheme 2

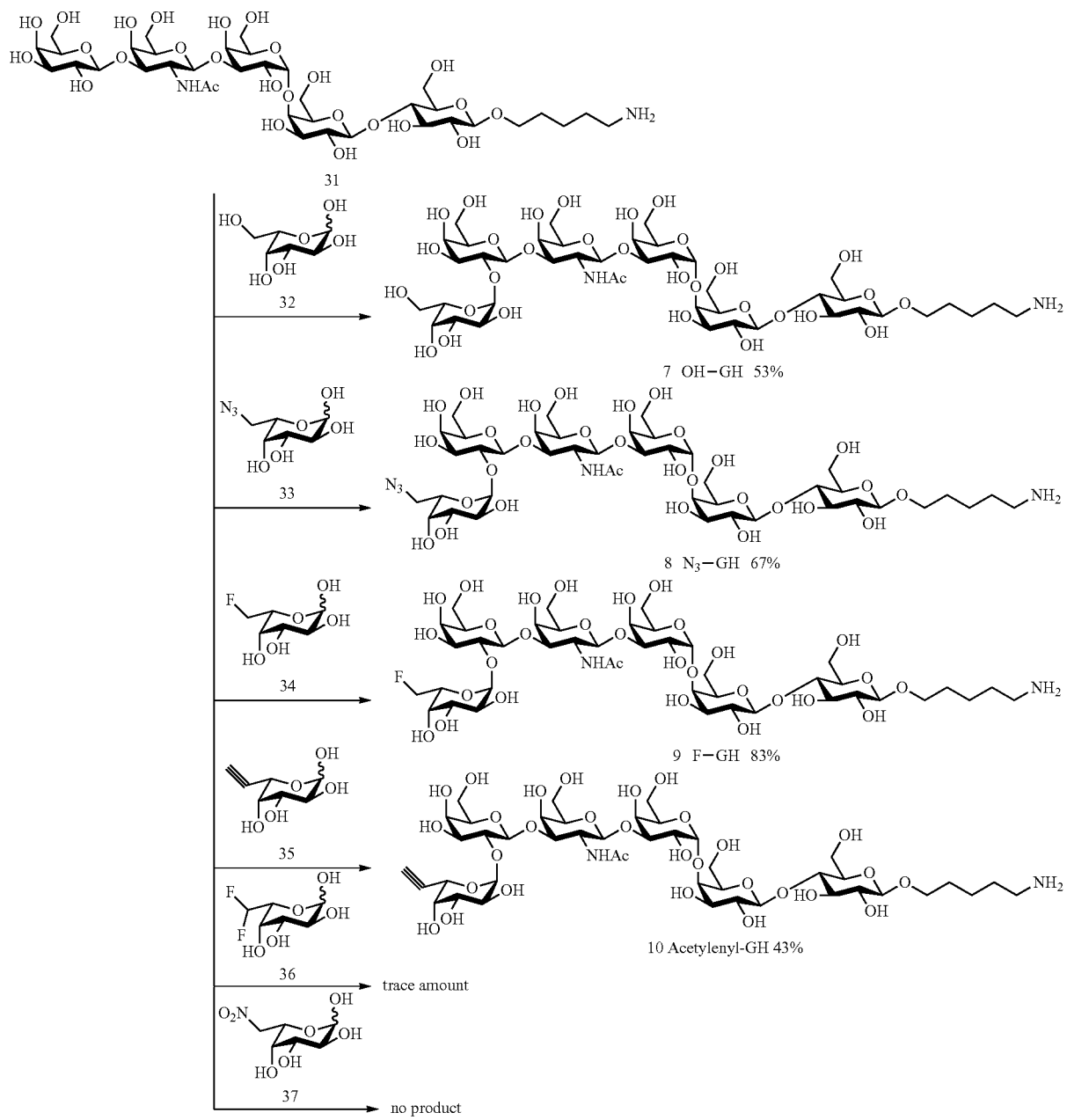

The synthesis of GH-Fuc derivatives 7-10 (nonreducing end derivatives) (Scheme 2) also followed the method previously described[15a] by combining the fucose derivative and the acceptor Gb5 oligosaccharide with recombinant FKP, α-1,2-fucosyltransferase (FutC), PPA and PK. The starting material Gb5 oligosaccharide with pentyl amine 31 was synthesized using a chemical method described previously.[29] Using this chemoezymatic method, a series of GH-Fuc derivatives 7-10 was synthesized in 43% to 83% yields. Although compound 36 was reacted with FKP to form GDP-36, it was not a suitable donor for FutC and a trace amount of the product was formed. In addition, compound 37 is not a substrate for FKP, and GDP-37 intermediate was not formed.

The structures of all purified GH derivatives and truncated forms were confirmed by nuclear magnetic resonance (NMR) spectroscopy and high-resolution mass spectrometry (HRMS) for further use.

Example 3: Synthesis of GH Derivatives DT-Conjugates

Scheme 3 shows synthesis of GH-Lac and GH-Fuc modified vaccines.

Scheme 3

1  GH
2  GH—F
3  GH—N₃
4  GH-phenyl
5  GH-4-nitrophenyl
6  GH—NO₂
7  OH—GH
8  N₃—GH
9  F—GH
10 Acetylenyl-GH

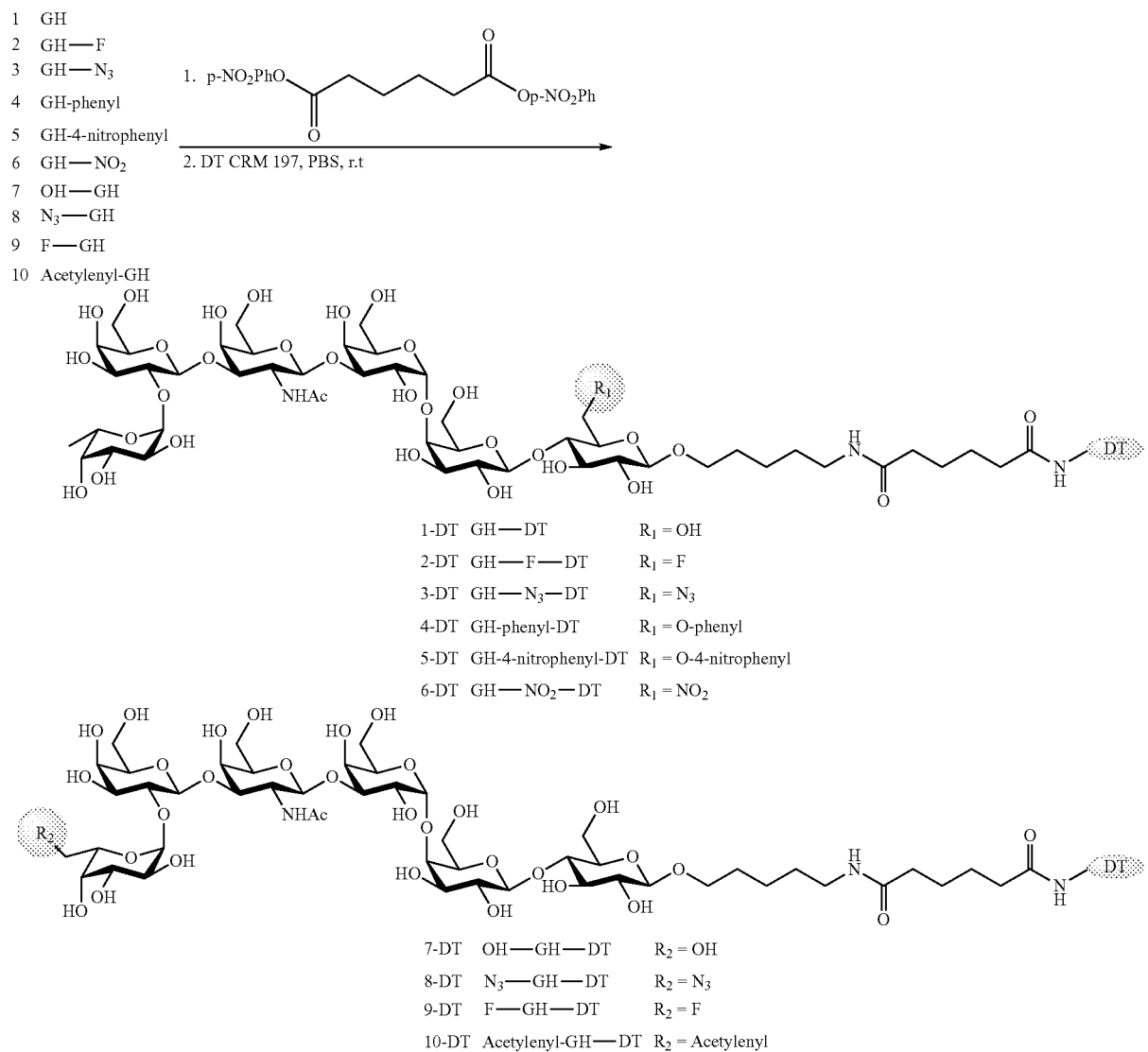

1-DT   GH—DT               $R_1$ = OH
2-DT   GH—F—DT             $R_1$ = F
3-DT   GH—N₃—DT            $R_1$ = N₃
4-DT   GH-phenyl-DT        $R_1$ = O-phenyl
5-DT   GH-4-nitrophenyl-DT $R_1$ = O-4-nitrophenyl
6-DT   GH—NO₂—DT           $R_1$ = NO₂

7-DT   OH—GH—DT            $R_2$ = OH
8-DT   N₃—GH—DT            $R_2$ = N₃
9-DT   F—GH—DT             $R_2$ = F
10-DT  Acetylenyl-GH—DT    $R_2$ = Acetylenyl To synthesize GH-Lac and GH-Fuc DT-conjugates (J-DT to 10-DT), the amine-terminated GH Lac derivatives 2-6 or GH Fuc derivatives 7-10 were reacted with the homobifunctional p-nitrophenyl linker to afford the corresponding half esters in good yields (supporting information). After purification by reverse phase chromatography, the half esters and DT were coupled in PBS buffer (pH 7.8) overnight (Scheme 3). The number of GH derivatives incorporated into DT was characterized by MALDI-TOF MS. Table 1 shows the results of MALDI-TOF analysis of average carbohydrate incorporation.[a] Peak m/z.

TABLE 1

| Glycoconjugate | After glycosylation[a] | (n)Average incorporation | Carbohydrate percentage |
| --- | --- | --- | --- |
| (1) GH-DT | 66943 | 7.10 | 12.9% |
| (2) GH-F-DT | 67406 | 7.47 | 13.4% |
| (3) GH-N₃-DT | 66505 | 6.60 | 12.2% |
| (4) GH-phenyl-DT | 66057 | 5.99 | 11.7% |
| (5) GH-4-nitrophenyl-DT | 67588 | 6.94 | 13.7% |
| (6) GH-NO₂-DT | 66119 | 6.12 | 11.7% |
| (7) OH-GH-DT | 64308 | 4.86 | 9.3% |
| (8) N₃-GH-DT | 64742 | 5.11 | 9.9% |
| (9) F-GH-DT | 68869 | 8.56 | 15.3% |
| (10) acetylenyl-GH-DT | 65881 | 6.17 | 11.5% |

Example 4: Syntheses of Precursors of GH-Lac and GH-Fuc Derivatives

Using a method based on the use of enzymes[30] coupled with effective sugar nucleotide regeneration,[15a] the GH-Lac and GH-Fuc derivatives can be readily prepared using glycosyltransferases (LgtC, LgtD, Futc) and cofactor regeneration systems (UDP-Gal, UDP-GalNAc, GDP-Fuc). The starting Lac derivatives 11-15 and the Fuc derivatives 32-37 were synthesized by chemical methods (Schemes 4-8).

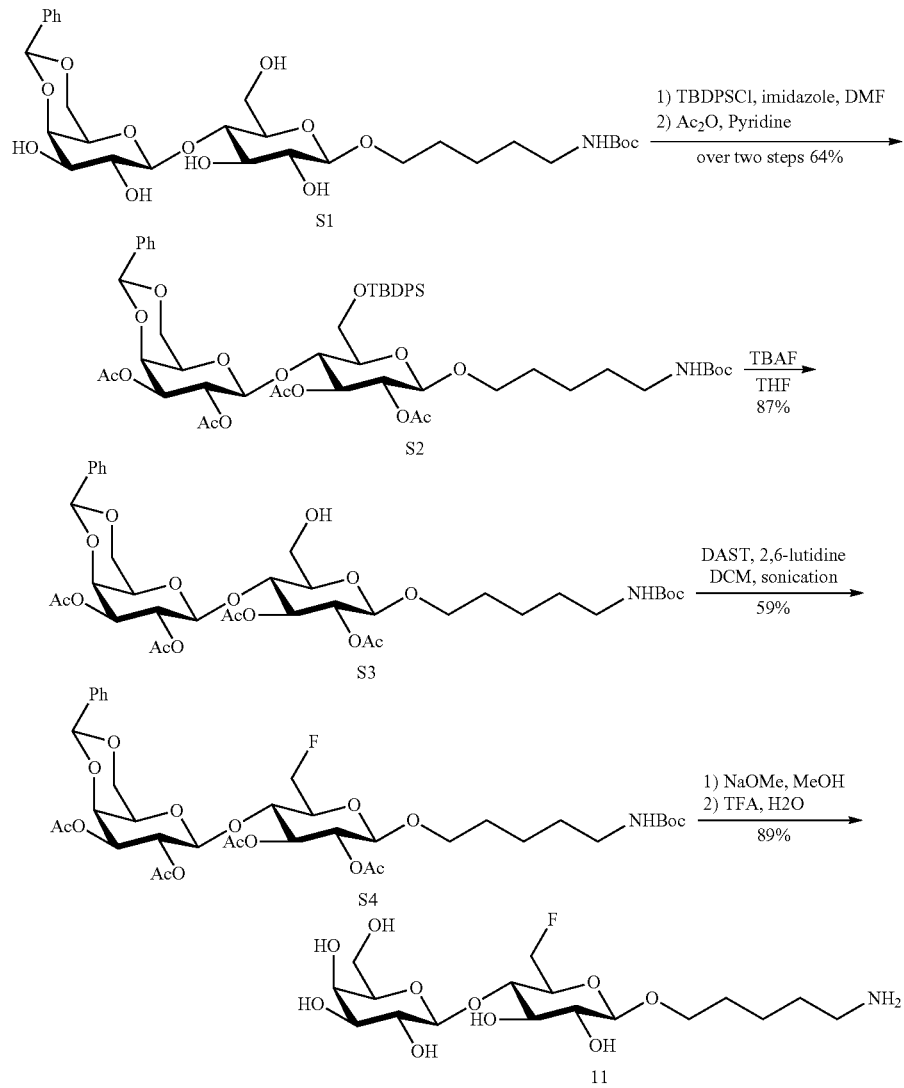

Scheme 4: Synthesis of lactose building blocks (11)

Compound S1 was synthesized by reported procedures.[1] To a solution of S1 (630 mg, 1.02 mmol) in DMF (30 mL) was added imidazole (208 mg, 3.07 mmol) at 0° C. and 291 μL (1.13 mmol) of tert-Butyl(chloro)diphenylsilane was added. The reaction mixture was slowly warmed to room temperature. After being stirred for 13 h, the reaction solution was concentrated. The residue was dissolved in pyridine (20 mL) at 0° C. and acetic anhydride (401 μL, 3.93 mmol) was added. The reaction mixture was slowly warmed to room temperature. After being stirred for 10 h, the reaction was quenched by the slow addition of methanol (1 mL) at 0° C., and the volatile materials were removed under reduced pressure. The residue was extracted with ethyl acetate (80 mL), washed with saturated NaHCO$_3$ aqueous solution, dried over Na$_2$SO$_4$, filtered, and concentrated. The residue was purified by flash silica get chromatography (0-40% EtOAc in Hexane) to afford S2 (667 mg, 64%). $^1$H-NMR (600 MHz, CDCl$_3$) δ 7.78-7.71 (m, 4H), 7.46-7.25 (m, 11H), 5.43 (s, 1H), 5.23-5.15 (m, 2H), 4.95 (m, 1H), 4.87-4.81 (m, 2H), 4.42 (d, J=8.0 Hz, 1H), 4.32-4.30 (dd, J=1.4, 12.5 Hz, 1H), 4.25 (d, J=3.6 Hz, 1H), 4.14 (t, J=9.6 Hz, 1H), 4.07 (d, J=1.5, 12.5 Hz, 1H), 3.96-3.90 (m, 2H), 3.85-3.81 (m, 1H), 3.44-3.40 (m, 1H), 3.31-3.30 (m, 2H), 3.08 (m, 2H), 2.08-2.00 (m, 9H), 1.77 (s, 3H), 1.60-1.58 (m, 2H), 1.48-1.45 (m, 2H), 1.41 (s, 9H), 1.35-1.33 (m, 2H), 1.05 (s, 9H), $^{13}$C NMR, (150 MHz, CDCl$_3$) δ 170.69, 170.66, 169.83, 168.64, 155.99, 137.55, 136.02, 135.43, 133.50, 132.20, 129.95, 129.92, 129.20, 128.26, 127.93, 127.67, 126.54, 101.40, 100.60, 100.26, 75.23, 74.26, 73.36, 72.36, 72.21, 71.68, 69.22, 68.99, 68.62, 66.27, 61.12, 29.77, 29.08, 28.44, 26.84, 23.30, 20.90, 20.82, 20.80, 20.59, 19.45. HRMS (ESI-TOF, MNa$^+$) calcd for C$_3$H$_{71}$NO$_{17}$SiNa$^+$ 1044.4383, found 1044.4404.

To a solution of S2 (425 mg, 0.41 mmol) in THF was added AcOH (246 μL, 4.10 mmol) at 0° C. 4.1 mL (4.10 mmol) of tetrabutylammonium fluoride solution 1.0 M in THF was added. The reaction mixture was slowly warmed to room temperature. After being stirred for 7 h, the reaction solution was concentrated under reduced pressure. The residue was extracted with ethyl acetate (70 mL), washed with saturated NaHCO$_3$ aqueous solution, dried over Na$_2$SO$_4$, filtered, and concentrated. The residue was purified by flash column chromatography (50-80% EtOAc in Hexane) to afford S3 (279 mg, 87%). $^1$H NMR (600 MHz, CDCl$_3$) δ 7.47-7.42 (m, 21H), 7.40-7.32 (m, 3H), 5.44 (s, 1H), 5.26-5.15 (m, 2H), 4.92-4.83 (m, 2H), 4.57 (m, 2H), 4.45 (d, J=8.0 Hz, 1H), 4.31-4.23 (m, 2H), 4.01 (dd, J=12.4, 1.5 Hz, 1H), 3.90 (m, 2H), 3.83-3.74 (m, 2H), 3.48-3.44 (m, 2H), 3.37 (d, J=9.7 Hz, 1H), 3.06 (m, 2H), 2.01 (dd, J=6.4, 2.8 Hz, 12H), 1.56-1.54 (m, 2H), 1.48-1.30 (m, 131H). $^{13}$C NMR (150 MHz, CDCl$_3$) δ 170.94, 170.60, 169.88, 169.05, 156.21, 137.74, 129.37, 128.44, 126.72, 101.54, 101.14, 100.86, 79.35, 75.30, 74.68, 73.49, 72.64, 72.31, 71.84, 70.11, 69.40, 68.78, 66.47, 60.46, 40.63, 29.78, 29.20, 28.63, 23.21, 21.06, 20.95. HRMS (ESI-TOF, MNa$^+$) calcd for C$_{37}$H$_{53}$NO$_{17}$Na$^+$ 806.3206, found 806.3212.

To a solution of S3 (221 mg, 0.28 mmol) in dry DCM (10 mL) was added 130 μL (1.2 mmol) of 2,6-lutidine at 0° C. 150 μL (1.2 mmol) of Diethylaminosulfur trifluoride was added. The mixture was sonicated for 8 h, and then concentrated in vacuo. The residue was purified by flash silica gel column chromatography (10-50% EtOAc in Hexane) to afford S4 (129 mg, 59%). $^1$H NMR (600 MHz, CDCl$_3$) δ 7.47-7.39 (m, 2H), 7.39-7.32 (m, 3H), 5.45 (s, 1H), 5.28-5.18 (m, 2H), 4.92-4.85 (m, 2H), 4.72-4.55 (m, 2H), 4.55-4.41 (m, 2H), 4.32-4.24 (m, 2H), 4.02 (dd, J=12.4, 1.4 Hz, 1H), 3.90-3.80 (m, 2H), 3.51-3.41 (m, 3H), 3.07 (dd, J=12.9, 6.4 Hz, 2H), 2.01 (dd, J=5.9, 4.3 Hz, 12H), 1.58-1.51 (m, 21), 1.51-1.38 (m, 11H), 1.38-1.26 (m, 2H). $^{19}$F NMR (470 MHz, CDCl$_3$) δ −234.24 (td, J=47.2, 29.6 Hz). $^{13}$C NMR (150 MHz, CDCl$_3$) δ 170.97, 170.43, 169.85, 169.06, 156.16, 137.62, 129.41, 128.45, 126.68, 101.49, 100.99, 100.92, 81.51, 80.36, 79.28, 74.67, 74.64, 74.03, 73.90, 73.39, 72.72, 72.21, 71.71, 69.99, 69.32, 68.68, 66.59, 40.63, 29.86, 29.18, 28.62, 23.32, 21.08, 20.94. HRMS (ESI-TOF, MNa$^+$) calcd for C$_{37}$H$_{52}$FNO$_{16}$Na$^+$ 808.3162, found 808.3185.

To a solution of S4 (105 mg, 0.13 mmol) in MeOH (10 mL) was added NaOMe (5 mg), and stirred for 6 h. The reaction solution was neutralized with Amberlite IR-120, filtered, and concentrated. The residue was treated with 5 mL of 90% TFA in H$_2$O. After being stirred for 2 h, the reaction solution was concentrated and purified by reverse phase column chromatography (RP-18) to afford lactose derivative 11 (49 mg, 89%)

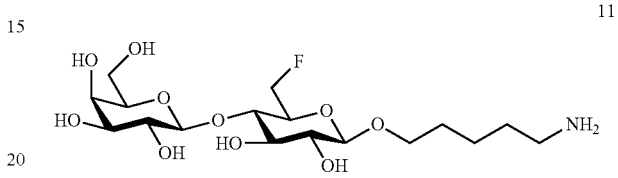

11

5-aminopentyl β-D-galactopyranosyl-(1→4)-6-deoxy-6-fluoro-β-D-glucopyranoside (Compound 11)

$^1$H NMR (600 MHz, D$_2$O) δ 4.88-4.71 (m, 1H), 4.54 (d, J=8.0 Hz, 1H), 4.46 (d, J=7.8 Hz, 1H), 3.93-3.90 (m, 2H), 3.84-3.65 (m, 8H), 3.56 (dd, J=10.0, 7.8 Hz, 1H), 3.34 (dd, J=9.3, 8.1 Hz, 1H), 3.02 (t, J=7.5 Hz, 2H), 1.75-1.65 (m, 4H), 1.51-1.43 (m, 2H). $^{19}$F NMR (471 MHz, D$_2$O) δ −234.79 (td, J=47.8, 31.6 Hz). $^{13}$C NMR (150 MHz, D$_2$O) δ 105.60, 104.84, 84.54, 83.43, 79.71, 79.67, 78.00, 76.88, 75.96, 75.84, 75.42, 75.14, 73.56, 72.90, 71.19, 63.71, 41.98, 30.82, 29.05, 24.73. HRMS (ESI-TOF, MH$^+$) calcd for C$_{17}$H$_{32}$FNO$_{10}$H$^+$ 430.2083, found 430.2092.

Scheme 5: Synthesis of lactose building blocks (12)

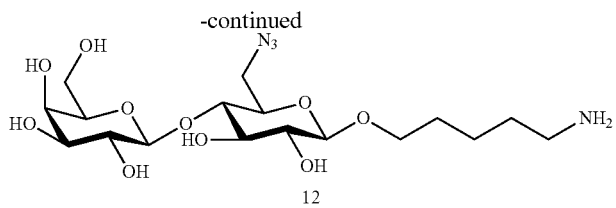

To a solution of S1 (1.9 g, 3.51 mmol) in pyridine (30 mL) was added 4-toluenesulfonyl chloride (0.8 g, 4.23 mmol) at 0° C. The reaction mixture was slowly warmed to room temperature. After being stirred for 8 h, the reaction solution was concentrated and purified by flash column chromatography (2-8% MeOH in DCM) to afford S5 (1.2 g, 45%); $^1$H NMR (600 MHz, CDCl$_3$) δ 7.78-7.76 (d, J=8.0 Hz, 2H), 7.44-7.42 (m, 2H), 7.34 (m, 31H), 7.24-7.23 (d, J=8.0 Hz, 21H), 5.49 (s, 1H), 4.61 (m, 1H), 4.52 (d, J=10.3 Hz, 1H), 4.38 (d, J=7.9 Hz, 1H), 4.28-4.17 (m, 21H). 4.15 (d, J=3.5 Hz, 1H), 4.02-4.00 (m, 1H), 3.77-3.72 (m, 21H), 3.61-3.55 (m, 4H), 3.49-3.41 (m, 3H), 3.32 (m, 1H), 2.38 (s, 3), 1.58-1.55 (m, 2H), 1.47-1.44 (m, 2H), 1.40 (s, 9H), 1.36-1.33 (m, 2H). $^{13}$C NMR (150 MHz, CDCl$_3$) δ 156.26, 137.72, 132.87, 130.03, 129.45, 128.52, 128.24, 126.63, 102.79, 102.46, 101.49, 79.29, 77.76, 75.35, 74.77, 73.44, 72.77, 72.61, 70.33, 70.11, 69.47, 69.05, 67.14, 40.61, 29.85, 29.25, 28.64, 23.38, 21.82. HRMS (ESI-TOF, MNa$^+$) calcd for C$_{36}$H$_{51}$NO$_{15}$SNa$^+$ 792.2872, found 792.2798.

To a solution of S5 (204 mg, 0.26 mmol) in DMF (5 mL) was added sodium azide (169 mg, 2.60 mmol) at 110° C. After being stirred for 14 h, the reaction solution was concentrated and purified by flash column chromatography (2-8% MeOH in DCM) to afford S6 (148 mg, 89%). $^1$H NMR (600 MHz, CDCl$_3$) δ 7.44 (m, 2H), 7.33-7.31 (m, 3H), 5.46 (s, 1H), 4.29-4.24 (m, 2H), 4.20 (d, J==12.5 Hz, 1H), 4.04 (m Hz, 1H), 3.97 (d, J=12.2 Hz, 1H), 3.84 (m, 1H), 3.72-3.63 (m, 1H), 3.60-3.33 (m, 10H), 3.26 (s, 1H), 3.04 (m, 2H), 1.59-1.57 (m, 2H), 1.45-1.19 (m, 13H), $^{13}$C NMR (150 MHz, CDCl$_3$) δ 137.57, 129.45, 128.47, 126.48, 103.37, 102.58, 101.42, 79.91, 79.34, 75.46, 74.62, 74.53, 73.47, 72.58, 70.47, 69.96, 69.12, 67.05, 51.17, 40.43, 29.73, 29.24, 28.56, 23.33. HRMS (ESI-TOF, MNa$^+$) calcd for C$_{29}$H$_{44}$N$_4$O$_{12}$Na$^+$ 663.2848, found 663.2859.

S6 (122 mg) was treated with 5 mL of 90% TFA in H$_2$O and stirred for 2 h, the reaction solution was concentrated and purified by reverse phase column chromatography (RP-18) to afford lactose derivative 12 (80 mg, 93%)

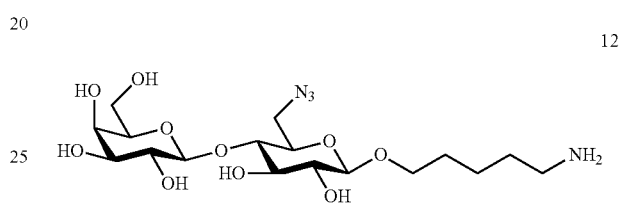

5-aminopentyl β-D-galactopyranosyl-(1→4)-6-azido-6-deoxy-β-D-glucopyranoside (Compound 12)

$^1$H NMR (600 MHz, D$_2$O) δ 4.54 (d, J=8.1 Hz, 1H), 4.44 (d, J=7.8 Hz, 1H), 3.98-3.91 (m, 2H), 3.85-3.60 (m, 10H), 3.55 (dd, J=9.9, 7.8 Hz, 1H), 3.38-3.32 (m, 1H), 3.06-2.99 (m, 2H), 1.76-1.65 (m, 4H), 1.52-1.43 (m, 2H). $^{13}$C NMR (150 MHz, D$_2$O) δ 105.84, 104.76, 82.08, 78.14, 76.98, 76.40, 75.54, 75.25, 73.64, 72.93, 71.26, 63.76, 53.14, 42.09, 30.92, 29.13, 24.83. HRMS (ESI-TOF, MH$^+$) calcd for C$_{17}$H$_{32}$N$_4$O$_{10}$H$^+$ 453.2191, found 453.2201.

Scheme 6: Synthesis of lactose building blocks (13)

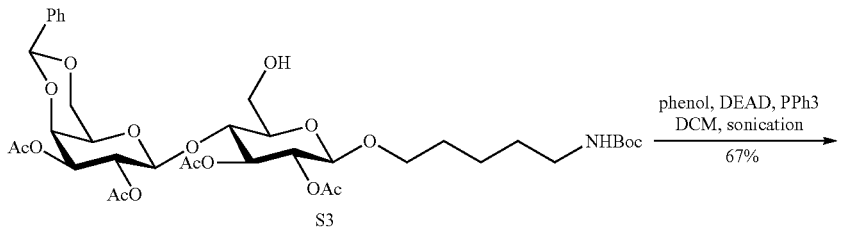

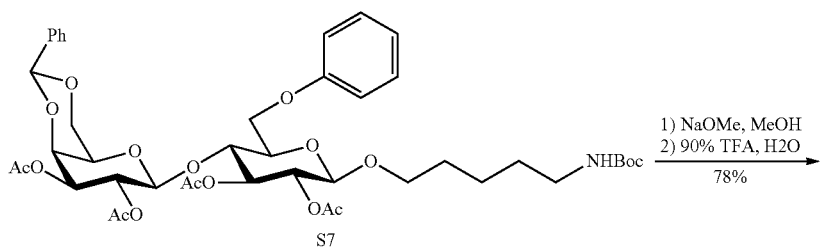

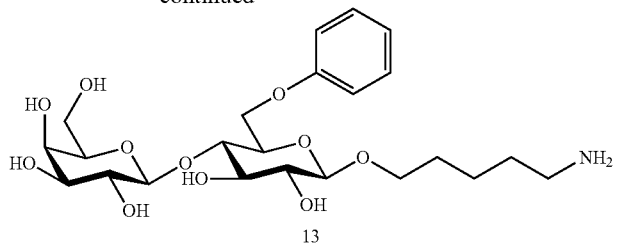

13

To a solution of S3 (190 mg, 0.24 mmol) in dry DCM (10 mL) was added 25 µL (0.27 mmol) of phenol and 70 mg (0.27 mmol) of triphenylphosphine at 0° C. 38 µL (0.27 mmol) of Diethyl azodicarboxylate was added. The mixture was sonicated for 4 h, and then concentrated in vacuo. The residue was purified by flash silica gel column chromatography (10-50% EtOAc in Hexane) to afford S7 (138 mg, 67%). $^1$H NMR (600 MHz, CDCl$_3$) δ 7.43-7.42 (dd, J=7.7, 1.7 Hz, 2H), 7.36-7.31 (m, 3H), 7.31-7.26 (m, 2H), 6.98-6.90 (m, 3H), 5.42 (s, 1H), 5.26-5.17 (m, 2H), 4.94 (dd, J=9.7, 8.0 Hz, 1H), 4.67 (dd, J=10.3, 3.7 Hz, 1H), 4.49-4.44 (m, 3H), 4.26-4.23 (m, 3H), 4.17 (m, 1H), 4.06-3.96 (m, 2H), 3.80 (dt, J=9.7, 6.3 Hz, 1H), 3.66 (m, 1H), 3.43 (dt, J: 9.6, 6.6 Hz, 1H), 3.34 (s, 1H), 3.05 (d, J=6.2 Hz, 2H), 2.01 (s, 3H), 2.00 (s, 3H), 1.97 (s, 3H), 1.88 (s, 3H), 1.59-1.48 (m, 2H), 1.48-1.38 (m, 11H), 1.36-1.19 (m, 2H). $^{13}$C NMR (150 MHz, CDCl$_3$) δ 170.89, 170.56, 169.88, 168.91, 158.56, 156.15, 137.67, 129.82, 129.37, 128.42, 126.67, 121.71, 115.00, 101.49, 101.01, 100.79, 79.23, 75.35, 74.07, 73.28, 72.80, 72.36, 71.83, 69.83, 69.26, 68.68, 66.51, 65.92, 40.63, 29.81, 29.17, 28.62, 23.28, 21.02, 20.94, 20.93, 20.84. HRMS (ESI-TOF, MNa$^+$) calcd for C$_{43}$H$_{57}$NO$_{17}$Na$^+$ 882.3519, found 882.3542.

To a solution of S7 (110 mg, 0.12 mmol) in MeOH (5 mL) was added NaOMe (3 mg), and stirred for 6 h. The reaction solution was neutralized with Amberlite IR-120, filtered, and concentrated. The residue was treated with 5 mL of 90% TFA in H$_2$O. After being stirred for 2 h, the reaction solution was concentrated and purified by reverse phase column chromatography (RP-18) to afford lactose derivative 13 (45 mg, 78%)

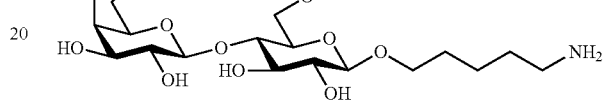

5-aminopentyl β-D-galactopyranosyl-(1→4)-6-O-phenyl-β-D-glucopyranoside (Compound 13)

$^1$H NMR (600 MHz, D$_2$O) δ 7.42 (dd, J=8.7, 7.4 Hz, 2H), 7.12-7.07 (m, 3H), 4.55 (d, J=8.0 Hz, 1H), 4.46 (dd, J=11.1, 1.6 Hz, 1H), 4.37 (dd, J=11.1, 4.0 Hz, 1H), 4.30 (d, J=7.8 Hz, 1H), 3.96-3.87 (m, 3H), 3.84 (d, J=3.4 Hz, 1H), 3.79-3.67 (m, 4H), 3.56 (dd, J=4.0, 8.3 Hz, 1H), 3.52 (m, 1H), 3.45-3.35 (m, 2H), 3.02 (t, J=7.5 Hz, 2H), 1.73-1.63 (m, 4H), 1.50-1.41 (m, 2H). $^{13}$C NMR (150 MHz, CDCl$_3$) δ 163.11, 135.23, 135.21, 127.09, 120.35, 108.11, 107.54, 82.71, 80.68, 79.65, 78.32, 78.17, 77.73, 76.06, 75.44, 73.81, 71.22, 66.35, 44.62, 33.46, 31.66, 27.34. HRMS (ESI-TOF, MH$^+$) calcd for C$_{23}$H$_{37}$NO$_{11}$H$^+$ 504.2439, found 504.2450.

Scheme 7: Synthesis of lactose building blocks (14)

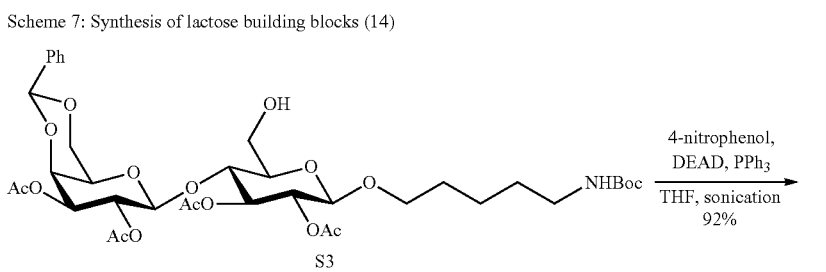

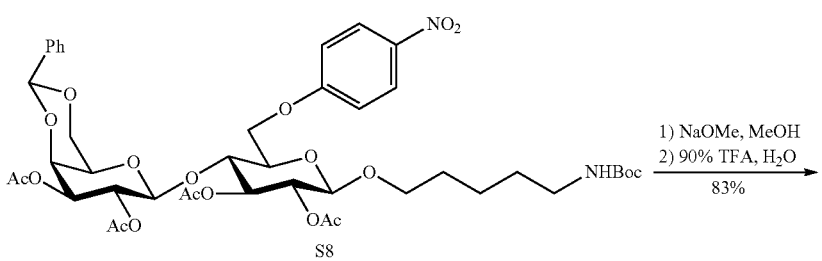

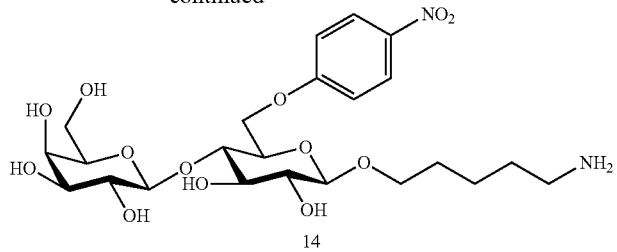

14

To a solution of S3 (220 mg, 0.28 mmol) in dry DCM (10 mL) was added 42 mg (0.30 mmol) of 4-nitrophenol and 81 mg (0.30 mmol) of triphenylphosphine at room temperature. 43 μL (0.30 mmol) of Diethyl azodicarboxylate was added. The mixture was sonicated for 5 h, then concentrated in vacuo. The residue was purified by flash silica gel column chromatography (20-60% EtOAc in Hexane) to afford S8 (235 mg, 92%). $^1$H NMR (600 MHz, CDCl$_3$) δ 8.19 (d, J=8.9 Hz, 2H), 7.41 (d, J=6.2 Hz, 2H), 7.33 (m, 3H), 7.00 (d, J=8.9 Hz, 2H), 5.43 (s, 1H), 5.23-5.19 (m, 2H), 4.90 (t, J=8.8 Hz, 1H), 4.76 (dd, J=10.3, 2.7 Hz, 1H), 4.52 (s, 1H), 4.47 (d, J=7.7 Hz, 2H), 4.36 (d, J=10.4 Hz, 1H), 4.26-4.24 (m, 3H), 4.04-3.93 (m, 2H), 3.78-3.73 (m, 2H), 3.41 (m, 2H), 3.03 (d, J=5.5 Hz, 2H), 2.05-1.94 (m, 9H), 1.87 (s, 3H), 1.56-1.35 (m, 13H), 1.29-1.91 (m, 2H). $^{13}$C NMR (150 MHz, CDCl$_3$) δ 170.72, 170.26, 169.73, 168.72, 163.43, 156.06, 142.12, 137.53, 129.30, 128.33, 126.53, 126.13, 114.89, 101.33, 100.93, 100.61, 79.13, 77.43, 75.31, 73.60, 73.18, 72.54, 72.00, 71.72, 69.99, 69.34, 68.53, 66.71, 66.56, 40.50, 29.75, 29.06, 28.52, 23.16, 20.89, 20.82, 20.81, 20.80. HRMS (ESI-TOF, MNa$^+$) calcd for C$_{43}$H$_{56}$N$_2$O$_{19}$Na$^+$ 927.3369, found 927.3377.

To a solution of S8 (155 mg, 0.17 mmol) in MeOH (5 mL) was added NaOMe (3 mg), and stirred for 6 h. The reaction solution was neutralized with Amberlite IR-120, filtered, and concentrated. The residue was treated with 5 mL of 90% TFA in H$_2$O. After being stirred for 2 h, the reaction solution was concentrated and purified by reverse phase column chromatography (RP-18) to afford lactose derivative 14 (78 mg, 83%)

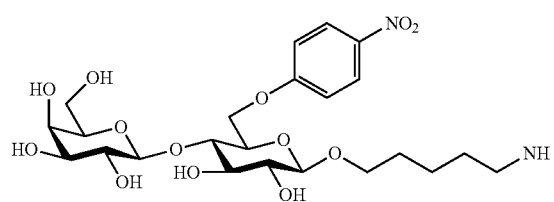

5-aminopentyl β-D-galactopyranosyl-(1→4)-6-O-p-nitrophenyl-β-D-glucopyranoside (14)

$^1$H NMR (600 MHz, D$_2$O) δ 8.29 (d, J=9.3 Hz, 2H), 7.20 (d, J=9.3 Hz, 2H), 4.57-4.53 (m, 3H), 4.32 (d, J=7.7 Hz, 1H), 3.97-3.84 (m, 4H), 3.84-3.66 (m, 4H), 3.60 (dt. J=11.7, 5.8 Hz, 1H), 3.53 (dd. J=9.9, 7.7 Hz, 1H), 3.47 (dd. J=9.9, 3.4 Hz, 1H), 3.41-3.35 (m, 1H), 2.97 (t, J=7.5 Hz, 2H), 1.69-1.63 (m, 4H), 1.45-1.41 (m, 2H). $^{13}$C NMR (150 MHz, D$_2$O) δ 163.56, 141.49, 126.22, 115.08, 103.07, 102.25, 77.72, 75.43, 74.34, 72.85, 72.78, 72.45, 70.74, 70.16, 68.47, 66.40, 61.03, 39.34, 28.17, 26.48, 22.07. HRMS (ESI-TOF, MH$^+$) calcd for C$_{23}$H$_{36}$N$_2$O$_{13}$H$^+$ 549.2290, found 549.2294.

Scheme 8: Synthesis of lactose building blocks (15)

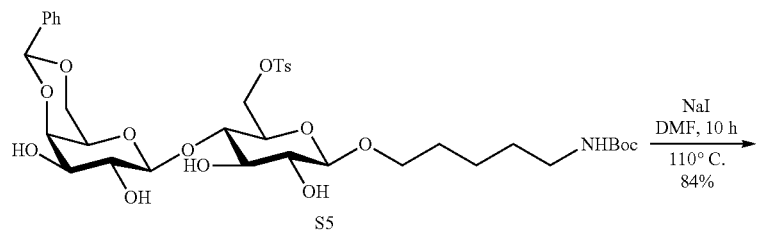

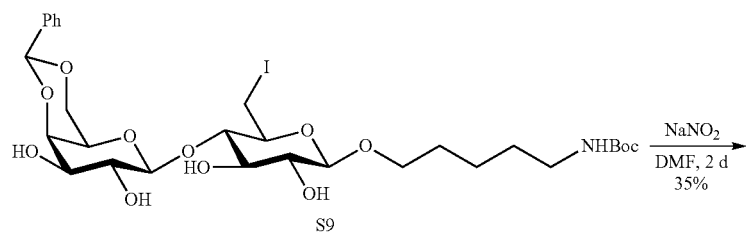

-continued

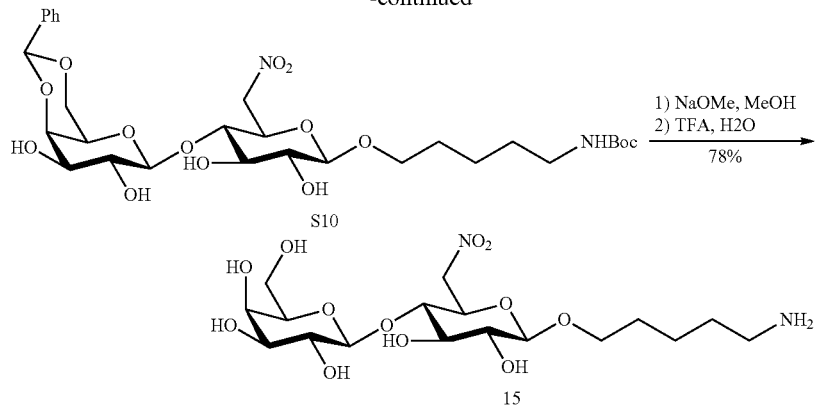

To a solution of S3 (188 mg, 0.24 mmol) in DMF (5 mL) was added sodium iodide (363 mg, 2.40 mmol) at 110° C. After being stirred for 14 h. the reaction solution was concentrated and purified by flash column chromatography (2-8% MeOH in DCM) to afford S9 (146 mg, 84%). $^1$H NMR (600 MHz, MeOD) δ 7.52-7.46 (m, 2H), 7.30-7.28 (m, 3H), 5.58 (s, 1H), 4.48-4.43 (m, 1H), 4.27 (dd. J=7.8, 4.0 Hz, 1H), 4.20-4.09 (m, 3H), 3.89-3.78 (m, 2H), 3.66-3.49 (m, 5H), 3.42-3.13 (m, 4H), 3.00 (t, J=7.0 Hz, 2H), 1.69-1.55 (m, 2H), 1.49-1.28 (m, 13H). $^{13}$C NMR (150 MHz, MeOD) δ 157.17, 138.13, 128.51, 127.64, 126.08, 103.78, 102.62, 100.81, 83.24, 78.43, 75.91, 74.32, 73.84, 73.45, 72.09, 70.48, 69.57, 68.78, 66.92, 46.63, 39.93, 29.27, 29.05, 27.44, 22.94, HRMS (ESI-TOF, MNa$^+$) calcd for C29H44INO12Na$^+$ 748.1800, found 748.1758.

To a solution of S9 (133 mg, 0.18 mmol) in DMF (5 mL) was added sodium nitrite (124 mg, 1.80 mmol) at room temperature for 2 d. The reaction solution was concentrated and purified by flash column chromatography (2-8% MeOH in DCM) to afford S10 (40 mg, 35%). $^1$H NMR (600 MHz, MeOD) δ 7.45 (dt, J=4.3, 2.3 Hz, 2H), 7.27-7.25 (m, 3H), 5.55 (s, 1H), 5.12 (dd, J=13.6, 2.5 Hz, 1H), 4.59-4.44 (m, 6H), 4.36 (d, J=7.5 Hz, 1H), 4.23 (d, J=7.8 Hz, 1H), 4.14-4.07 (m, 4H), 3.67-3.49 (m, 5H), 3.48-3.39 (m, 2H), 3.18-3.14 (m, 1H), 2.93 (t, J=7.0 Hz, 2H), 1.56-1.45 (m, 2H), 1.39-1.32 (m, 11H), 1.32-1.24 (m, 2H). $^{13}$C NMR (150 MHz, MeOD) δ 157.20, 138.17, 128.56, 127.69, 126.10, 103.60, 102.87, 100.86, 79.81, 78.45, 75.91, 75.74, 74.62, 73.23, 72.10, 71.38, 70.17, 69.68, 68.78, 67.01, 39.91, 29.25, 29.02, 27.44, 22.90. HRMS (ESI-TOF, MNa$^+$) calcd for C29H44N2O14Na$^+$ 667.2685, found 667.2726.

S10 (40 mg, 0.06 mmol) was treated with 5 mL of 90% TFA in H$_2$O and stirred for 2 h, the reaction solution was concentrated and purified by reverse phase column chromatography (RP-18) to afford lactose derivative 15 (22 mg, 78%)

15

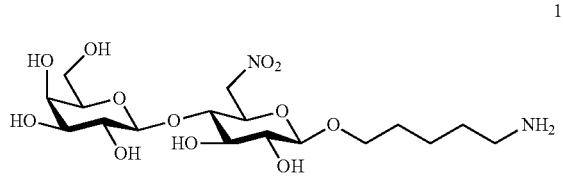

5-aminopentyl β-D-galactopyranosyl-(1→4)-6-deoxy-6-nitro-β-D-glucopyranoside (15)

$^1$H NMR (600 MHz, D$_2$O) δ 4.56 (d, J=8.1 Hz, 1H), 4.47 (d, J=7.8 Hz, 1H), 4.34 (d, J=9.5 Hz, 1H), 3.95 (d, J=3.3 Hz, 1H), 3.86-3.65 (m, 8H), 3.57 (dd, J=9.9, 7.9 Hz, 1H), 3.35 (t, J=8.6 Hz, 1H), 3.04-2.97 (m, 2H), 1.66 (m, 4H), 1.47-1.38 (m, 2H). $^{13}$C NMR (150 MHz, 120) δ 105.84, 104.88, 82.22, 78.46, 78.25, 76.89, 75.36, 75.24, 73.91, 73.53, 73.37, 71.21, 63.71, 42.06, 30.93, 29.09, 24.76. HRMS (ESI-TOF, MH$^+$) calcd for C$_{17}$H$_{32}$N$_2$O$_{12}$H$^+$ 457.2028, found 457.2036. Compounds 33, 34, 35, 36, 37 was synthesized by reported procedures.[2]

Synthesis of Gb3-Lac Derivatives

The reactions were performed in 15-mL centrifuge tubes with 5.0 mL Tris-HCl buffer (100 mM, pH 7.0) containing Lac derivatives (10-15 mg), galactose (1.0 equiv), PEP (4.4 equiv), ATP disodium salt (0.1 equiv), UTP disodium salt (0.1 equiv), MgCl$_2$ (10 mM), α-1,4-galactosyltransferase (LgtC, 3.0 unit), galactokinase (GalK, 2.0 units), UDP-sugar pyrophosphorylase (AtUSP, 2.8 units), pyruvate kinase (PK, 2.5 units), and pyrophosphatase (PPA, 2.5 units). The reaction mixture was incubated at room temperature for overnight with shaking (300 rpm). The reaction was monitored by TLC analysis using 5:3:2 butanol/acetate/water as the developing solvent and the plates were stained with anisaldehyde in ethanol. The tube was put in the hot bath (80° C.) for 10 min, followed by centrifugation (10000 rpm, 15 min) and the supernatant was concentrated in vacuo. The aqueous residue was then purified by C-18 gel chromatography and eluted by a gradient from 100% H$_2$O to 80% methanol in H$_2$O. Only the fractions containing the product were collected, lyophilized and characterized by NMR spectroscopy and HRMS.

Synthesis of Gb4-Lac Derivatives

The reactions were achieved in 15-mL centrifuge tubes with 3.0 mL Tris-HCl buffer (100 mM, pH 7.0) containing Gb3 derivatives (8-12 mg), N-acetylgalactosamine (GAlNAc, 1.1 equiv). PEP (4.4 equiv), ATP disodium salt (0.1 equiv), UTP disodium salt (0.1 equiv), MgCl$_2$ (10 mM). β-1,3-N-acetylgalacto-saminyltransferase (β1,3GalNAcT, LgtD, 3.5 unit), N-acetylhexosamine 1-kinase (NahK, 5.0 units), N-acetylglucosamine 1-phosphate uridylyltransferase (GlmU, 3.0 units), PK (2.5 units), PPA (2.5 units). The reaction mixture was incubated at room temperature for overnight with shaking (300 rpm). The reaction was monitored by TLC analysis using 5:3:2 butanol/acetate/water as the developing solvent and the plates were stained with anisaldehyde in ethanol. The tube was put in the hot bath (80° C.) for 10 min, followed by centrifugation (10000 rpm, 15 min) and the supernatant was concentrated in vacuo. The aqueous residue was then purified by C-18 gel chromatography and eluted by a gradient from 100% $H_2O$ to 80% methanol in $H_2O$. Only the fractions containing the product were collected, lyophilized and characterized by NMR spectroscopy and HRMS.

Synthesis of Gb5-Lac Derivatives

The reactions were carried out in 15-mL centrifuge tubes with 3.0 mL Tris-HCl buffer (100 mM, pH 7.0) containing Gb4 derivatives (5-8 mg), galactose (1.1 equiv), PEP (4.4 equiv), ATP disodium salt (0.1 equiv), UTP disodium salt (0.1 equiv), $MgCl_2$ (10 mM), β-1,3-galactosyltransferase (β1,3GalT, LgtD, 5.0 unit), (GalK (2.5 units), AtUSP (4.0 units), PK (2.5 units), and PPA (2.5 units). The reaction mixture was incubated at room temperature for overnight with shaking (300 rpm). The reaction was monitored by TLC analysis using 3:2:2 butanol/acetate/water as the developing solvent and the plates were stained with anisaldehyde in ethanol. The tube was put in the hot bath (80° C.) for 10 min, followed by centrifugation (10000 rpm, 15 min) and the supernatant was concentrated in vacuo. The aqueous residue was then purified by C-18 gel chromatography and eluted by a gradient from 100% $H_2O$ to 70% methanol in $H_2O$. Only the fractions containing the product were collected, lyophilized and characterized by NMR spectroscopy and HRMS.

Synthesis of Globo H-Lac Derivatives or Globo H-Fuc Derivatives

The reactions were performed in 15-mL centrifuge tubes with 3.0 mL Tris-HCl buffer (100 mM, pH 7.0) containing Gb5 derivatives (4-6 mg), L-fucose or their derivatives (1.2 equiv), PEP (4.4 equiv), ATP disodium salt (0.1 equiv), GTP disodium salt (0.1 equiv), $MgCl_2$ (10 mM), α-1,2-fucosyltransferase (FutC, 3.0 unit), L-fucokinase/GDP-fucose pyrophosphorylase (FKP), PK (2.5 units), and PPA (2.5 units). The reaction mixture was incubated at room temperature for overnight with shaking (300 rpm). The reaction was monitored by TLC analysis using 3:2:2 butanol/acetate/water as the developing solvent and the plates were stained with anisaldehyde in ethanol. The tube was put in the hot bath (80° C.) for 10 min, followed by centrifugation (10000 rpm, 15 min) and the supernatant was concentrated in vacuo. The aqueous residue was then purified by C-18 gel chromatography and eluted by a gradient from 100% $H_2O$ to 80% methanol in $H_2O$. Only the fractions containing the product were collected, lyophilized and characterized by NMR spectroscopy and HRMS.

5-aminopentyl α-D-Galactopyranosyl-(1→4)-β-D-galactopyranosyl-(1→4)-6-deoxy-6-fluoro-β-D-glucopyranoside (16)

$^1$H-NMR (600 MHz, $D_2O$) δ 4.97 (d, J=3.9 Hz, 1H), 4.94-4.70 (m, 1H), 4.53 (d, J=8.0 Hz, 1H), 4.53 (d, J=7.7 Hz, 1H), 4.37 (t, J=6.5 Hz, 1H), 4.05 (dd, J=7.9, 3.2 Hz, 2H), 3.98-3.64 (m, 14H), 3.60 (dd, J=10.3, 7.8 Hz, 1H), 3.33 (dd, J=9.3, 8.1 Hz, 1H), 2.92 (m, 2H), 1.76-1.64 (m, 14H), 1.52-1.42 (m, 2H). $^{19}$F NMR (470 MHz, $CDCl_3$) δ −234.92 (td, J=47.0, 32.9 Hz). $^{13}$C NMR (150 MHz, $D_2O$) δ 103.29, 102.15, 100.31, 81.94, 80.82, 77.40, 77.36, 75.40, 74.29, 73.35, 73.23, 72.87, 72.15, 70.87, 70.81, 70.25, 69.13, 68.92, 68.53, 60.49, 60.38, 39.37, 28.17, 26.55, 22.07. HRMS (ESI-TOF, $MH^+$) calcd for $C_{23}H_{42}FNO_{15}H^+$ 592.2611, found 592.2620.

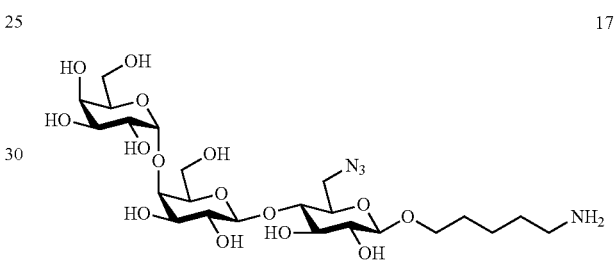

17

5-aminopentyl α-D-Galactopyranosyl-(1→4)-β-D-galactopyranosyl-(1→4)-6-azido-6-deoxy-β-D-glucopyranoside (17)

$^1$H NMR (600 MHz, $D_2O$) δ 4.97 (d, J=3.9 Hz, 1H), 4.55 (d, J=8.0 Hz, 1H), 4.49 (d, J=7.8 Hz, 1H), 4.37 (t, J=6.6 Hz, 1H), 4.06 (dd, J=7.6, 3.0 Hz, 2H), 4.00-3.56 (m, 16H), 3.34 (t, J=8.6 Hz, 1H), 3.01-2.94 (t, J=7.2 Hz, 2H), 1.72-1.66 (m, 4H), 1.49-1.43 (m, 2H). $^{13}$C NMR (150 MHz, $D_2O$) δ 106.16, 104.71, 103.03, 82.33, 80.03, 78.20, 77.04, 76.44, 75.62, 74.89, 73.61, 73.55, 72.99, 71.87, 71.66, 71.28, 63.23, 63.10, 53.12, 42.21, 30.97, 29.78, 24.88 HRMS (ESI-TOF, $MH^+$) calcd for $C_{23}H_{42}N_4O_{15}H^+$ 615.2719, found 615.2734.

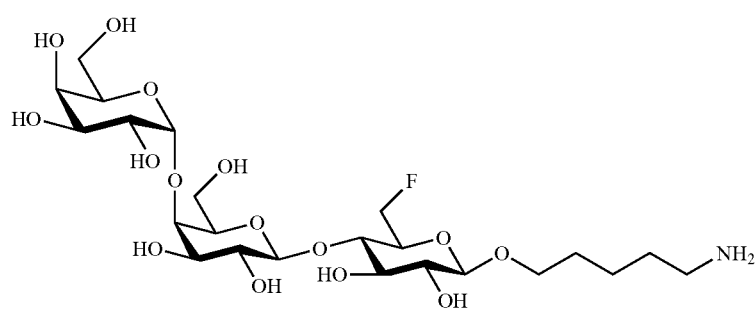

16

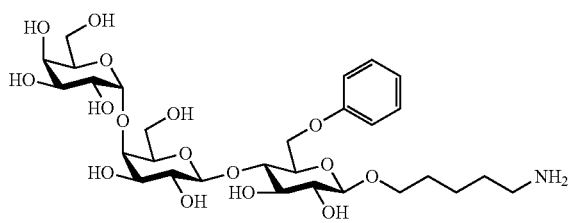

5-aminopentyl α-D-Galactopyranosyl-(1→4)-β-D-galactopyranosyl-(1→4)-6-O-phenyl-β-D-glucopyranoside (18)

¹H NMR (600 MHz, D$_2$O) δ 7.43 (t, J=8.0 Hz, 2H), 7.11 (m, 3H), 4.94 (d, J=3.9 Hz, 1H), 4.56 (d, J=8.0 Hz, 1H), 4.48 (d, J=10.3 Hz, 1H), 4.42 (dd, J=10.9, 3.5 Hz, 1H), 4.35 (m, 2H), 4.04 (d, J=3.0 Hz, 18), 3.97-3.81 (m, 8H), 3.79-3.65 (m, 4H), 3.65-3.48 (m, 3H), 3.37 (t, J=8.3 Hz, 1H), 2.98 (t, J=6.7 Hz, 2H), 1.68 (s, 4H), 1.47 (dd, J=14.6, 7.4 Hz, 2H). ¹³C NMR (150 MHz, D$_2$O) δ 160.54, 132.68, 124.56, 117.82, 105.93, 104.97, 103.00, 80.47, 80.05, 78.23, 77.13, 75.83, 75.73, 74.84, 73.54, 73.43, 72.92, 71.85, 71.65, 71.26, 68.62, 63.23, 63.15, 42.12, 30.93, 29.34, 24.81. HRMS (ESI-TOF, MH$^+$) calcd for C$_{29}$H$_{47}$NO$_{16}$H$^+$ 666.2968, found 666.2979.

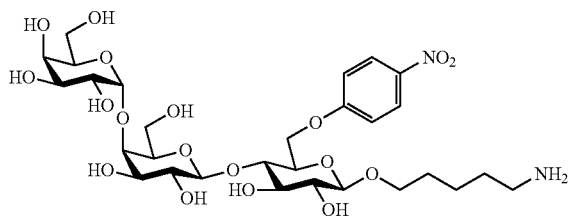

5-aminopentyl α-D-Galactopyranosyl-(1→4)-β-D-galactopyranosyl-(1→4)-6-O-p-nitrophenyl-β-D-glucopyranoside (19)

¹H NMR (600 MHz, D$_2$O) δ 8.29 (d, J=9.3 Hz, 2H), 7.20 (d, =9.3 Hz, 2H), 4.94 (d, J=4.0 Hz, 1H), 4.59-4.50 (m, 3H), 4.37 (d, J=7.7 Hz, 1H), 4.34 (t, J=5.7 Hz, 1H), 4.04 (d, J=2.8 Hz, 1H), 3.99 (d, J=2.7 Hz, 1H), 3.97-3.84 (m, 4H), 3.84-3.66 (m, 4H), 3.73-3.66 (m, 5H), 3.60-3.53 (m, 2H), 3.39-3.36 (m, 11H), 2.97 (t, J=7.5 Hz, 2H), 1.68-1.63 (m, 4H), 1.46-1.41 (m, 2H). ¹³C NMR (150 MHz, D$_2$O) δ 166.28, 144.25, 128.97, 117.83, 106.20, 104.97, 102.99, 80.82, 79.96, 78.25, 77.13, 75.68, 75.56, 74.86, 73.54, 73.43, 72.93, 71.85, 71.65, 71.25, 69.09, 63.22, 63.12, 42.15, 30.94, 29.56, 24.84. HRMS (ESI-TOF, MH$^+$) calcd for C$_{29}$H$_{46}$N$_2$O$_{18}$H$^+$ 711.2818, found 711.2800.

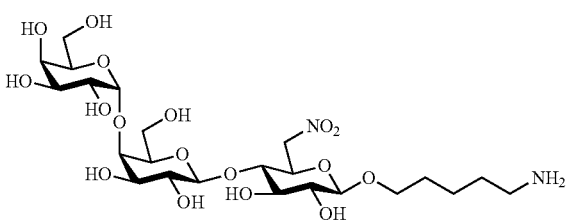

5-aminopentyl α-D-Galactopyranosyl-(1→4)-β-D-galactopyranosyl-(1→4)-6-deoxy-6-nitro-β-D-glucopyranoside (20)

¹H NMR (600 MHz, D$_2$O) δ 4.96 (d, J=3.9 Hz, 1H), 4.54 (m, 2H), 4.36 (t, J=6.2 Hz, 1H), 4.31 (d, J=9.2 Hz, 1H), 4.05-4.03 (m, 2H), 3.99-3.51 (m, 151H), 3.32 (m, 1H), 3.00 (m, 2H), 1.68-1.60 (m, 4H), 1.46-1.40 (m, 2H). ¹³C NMR (150 MHz, D$_2$O) δ 102.70, 101.73, 100.04, 79.37, 76.98, 75.20, 73.91, 72.59, 71.80, 70.45, 70.40, 70.34, 69.95, 68.86, 68.61, 68.32, 65.87, 60.19, 60.13, 52.12, 39.71, 29.10, 28.16, 22.00. HRMS (ESI-TOF, MH$^+$) calcd for C$_{23}$H$_{42}$N$_2$O$_{17}$H$^+$ 619.2556, found 619.2559.

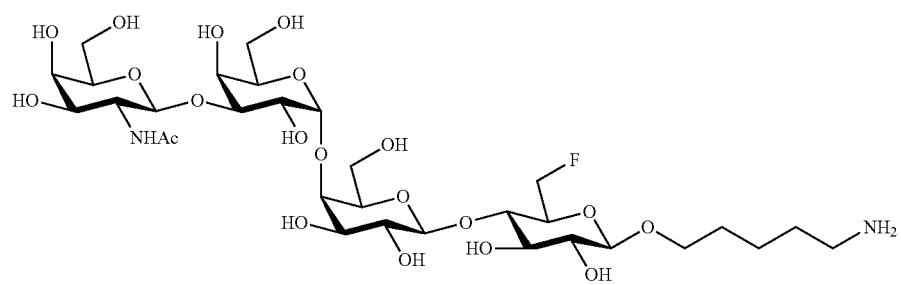

5-aminopentyl 2-acetamido-2-deoxy-β-D-galactopyranosyl-(1→3)-α-D-Galactopyranosyl-(1→4)-β-D-galactopyranosyl-(1→4)-6-deoxy-6-fluoro-β-D-glucopyranoside (21)

$^1$H NMR (600 MHz, D$_2$O) δ 4.93 (d, J=3.9 Hz, 1H), 4.92-4.74 (m, 2H), 4.75 (d, J=10.5 Hz, 1H), 4.66 (d, J=8.3 Hz, 1H), 4.55 (d, J=8.0 Hz, 1H), 4.53 (d, J=7.8 Hz, 1H), 4.41 (t, J=6.5 Hz, 1H), 4.28 (d, J=2.5 Hz, 1H), 4.07 (d, J=3.1 Hz, 1H), 4.02-3.64 (m, 18H), 3.62 (dd, J=10.2, 7.8 Hz, 1H), 3.34 (m, 1H), 2.99 (t, J=7.5 Hz, 2H), 2.07 (s, 3H), 1.75-1.64 (m, 4H), 1.55-1.43 (m, 2H). $^{19}$F NMR (471 MHz, D$_2$O) δ −234.84 (td, J=47.0, 32.9 Hz). $^{13}$C NMR (150 MHz, D$_2$O) δ 177.91, 106.06, 105.95, 104.89, 103.15, 84.69, 83.57, 81.42, 80.22, 80.18, 79.97, 78.16, 77.68, 77.05, 76.10, 75.98, 75.65, 74.85, 73.59, 73.52, 73.03, 71.67, 70.50, 70.35, 63.74, 63.11, 63.07, 55.35, 42.19, 30.95, 29.68, 24.99, 24.85. HRMS (ESI-TOF, MH$^+$) calcd for C$_{31}$H$_{55}$FN$_2$O$_{20}$H$^+$ 795.3405, found 795.3429.

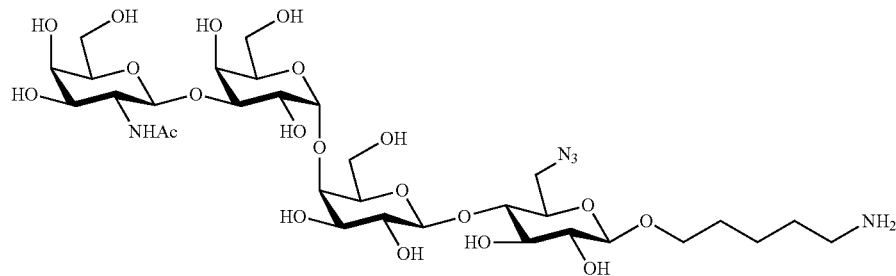

22

5-aminopentyl 2-acetamido-2-deoxy-β-D-galactopyranosyl-(1→3)-α-D-Galactopyranosyl-(1→4)-β-D-galactopyranosyl-(1→4)-6-azido-6-deoxy-β-D-glucopyranoside (22)

$^1$H NMR (600 MHz, D$_2$O) δ 4.94 (d, J=3.9 Hz, 1H), 4.66 (d, J=8.4 Hz, 1H), 4.56 (d, J=8.0 Hz, 1H), 4.51 (d, J=7.8 Hz, 1H), 4.40 (t, J=6.6 Hz, 1H), 4.28 (d, J=2.6 Hz, 1H), 4.07 (d, J=3.1 Hz, 1H), 4.02-3.57 (m, 22H), 3.35 (t, J=8.5 Hz, 1H), 2.99 (t, J=7.5 Hz, 2H), 2.07 (s, 3H), 1.76-1.63 (m, 4H), 1.48 (dt, J=15.5, 7.7 Hz, 2H). $^{13}$C NMR (150 MHz, D$_2$O) δ 177.91, 106.19, 105.95, 104.72, 103.13, 82.41, 81.43, 79.90, 78.23, 77.68, 77.07, 76.44, 75.66, 74.85, 73.59, 73.53, 73.00, 72.99, 71.67, 70.50, 70.34, 63.74, 63.11, 63.05, 55.36, 53.13, 42.17, 30.97, 29.57, 24.99, 24.88. HRMS (ESI-TOF, MH$^+$) calcd for C$_{31}$H$_{55}$N$_5$O$_{20}$H$^+$ 818.3513, found 818.3543.

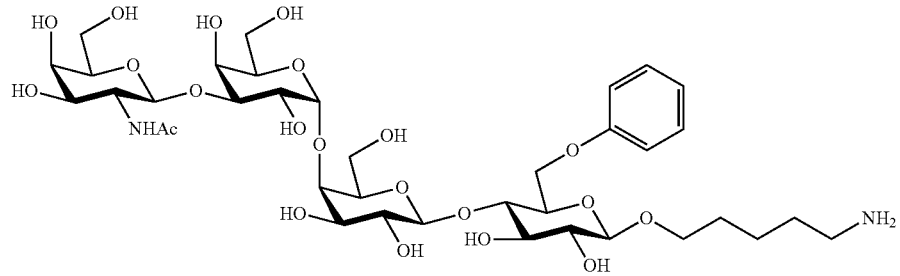

23

5-aminopentyl 2-acetamido-2-deoxy-β-D-galactopyranosyl-(1→3)-α-D-Galactopyranosyl-(1→4)-β-D-galactopyranosyl-(1→4)-6-O-phenyl-β-D-glucopyranoside (23)

$^1$H NMR (600 MHz, D$_2$O) δ 7.40 (t, J=7.8 Hz, 2H), 7.08 (m, 3H), 4.89 (d, J=3.8 Hz, 1H), 4.64 (d, J=8.4 Hz, 1H), 4.54 (d, J=7.9 Hz, 1H), 4.47-4.31 (m, 4H), 4.25 (d, J=2.3 Hz, 1H), 4.00-3.84 (m, 9H), 3.84-3.67 (m, 9H), 3.67-3.45 (m, 3H), 3.43-3.34 (m, 1H), 2.98 (m, 2H), 2.05 (s, 31H), 1.66 (m, 4H), 1.44 (m, 2H). $^{13}$C NMR (150 MHz, D$_2$O) δ 177.92, 160.53, 132.66, 124.54, 117.79, 105.96, 105.95, 104.96, 103.10, 81.41, 80.58, 79.91, 78.24, 77.67, 77.15, 75.83, 75.77, 75.58, 74.80, 73.52, 73.40, 72.99, 72.90, 71.67, 70.50, 70.33, 68.64, 63.74, 63.10, 55.34, 42.06, 30.92, 29.13, 25.00, 24.80. HRMS (ESI-TOF, MH$^+$) calcd for C$_{37}$H$_{60}$N$_2$O$_{21}$H$^+$ 869.3761, found 869.3795.

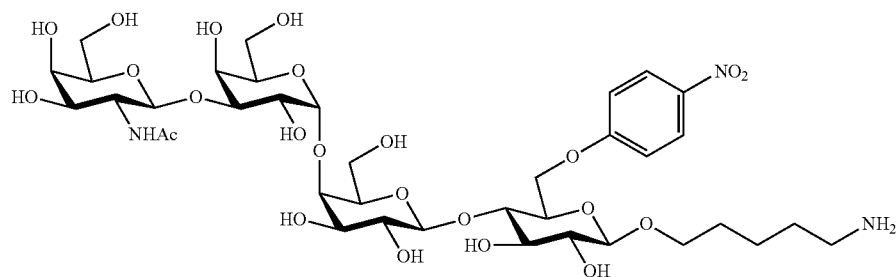

24

5-aminopentyl 2-acetamido-2-deoxy-β-D-galactopyranosyl-(1→3)-α-D-Galactopyranosyl-(1→4)-β-D-galactopyranosyl-(1→4)-6-O-p-nitrophenyl-β-D-glucopyranoside (24)

$^1$H NMR (600 MHz, D$_2$O) δ 8.29 (d, J=9.1 Hz, 2H), 7.20 (d, J=9.2 Hz, 2H), 4.90 (d, J=3.8 Hz, 1H), 4.65 (d, J=8.4 Hz, 1H), 4.56 (m, 3H), 4.41-4.33 (m, 2H), 4.25 (d, J=2.6 Hz, 1H), 4.02-3.74 (m, 13H), 3.73-3.63 (m, 7H), 3.61-3.52 (m, 2H), 3.38 (t, J=8.7 Hz, 1H), 2.87 (t, J=7.3 Hz, 2H), 2.06 (s, 3H), 1.66-1.59 (m, 4H), 1.44-1.40 (m, 2H), $^{13}$C NMR (150 MHz, D$_2$O) δ 177.90, 166.28, 144.25, 128.97, 117.83, 106.20, 105.93, 104.97, 103.10, 81.39, 80.92, 79.85, 78.27, 77.68, 77.16, 75.72, 75.57, 74.83, 73.52, 73.42, 73.00, 72.89, 71.66, 70.50, 70.32, 69.11, 63.74, 63.10, 55.36, 42.08, 30.94, 29.20, 24.99, 24.82. HRMS (ESI-TOF, MH$^+$) calcd for C$_{37}$H$_{59}$N$_3$O$_{23}$H$^+$ 914.3612, found 914.3609.

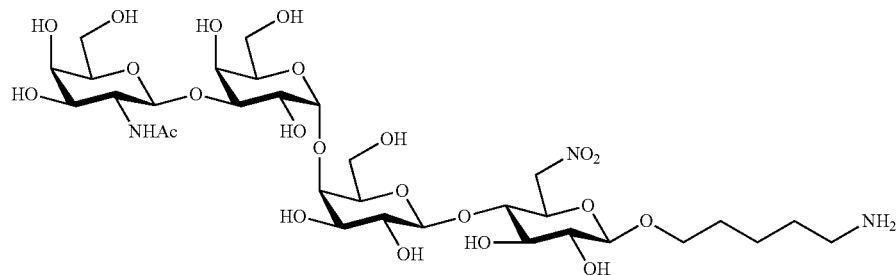

25

5-aminopentyl 2-acetamido-2-deoxy-β-D-galactopyranosyl-(1→3)-α-D-Galactopyranosyl-(1→4)-β-D-galactopyranosyl-(1→4)-6-deoxy-6-nitro-β-D-glucopyranoside (25)

$^1$H NMR (600 MHz, D$_2$O) δ 4.96-4.90 (m, 1H), 4.68-4.50 (m, 4H), 4.39 (t, J=6.1 Hz, 1H), 4.32 (d, J=9.4 Hz, 1H), 4.27 (d, J=2.0 Hz, 1H), 4.05 (dd, J=9.6, 2.9 Hz, 1H), 4.01-3.64 (m, 19H), 3.64-3.53 (m, 1H), 3.38-3.29 (m, 1H), 3.07-2.91 (m, 2H), 2.05 (s, 3H), 1.70-1.60 (m, 4H), 1.47-1.40 (m, 2H). $^{13}$C NMR (150 Hz, D$_2$O) δ 175.16, 103.45, 103.22, 102.10, 100.37, 79.82, 78.70, 77.08, 75.53, 74.92, 74.24, 72.71, 72.08, 71.09, 70.77, 70.75, 70.60, 70.25, 68.91, 67.74, 67.58, 60.98, 60.35, 60.24, 52.59, 39.31, 39.29, 28.18, 26.37, 22.23, 22.01. HRMS (ESI-TOF, MH$^+$) calcd for C$_{31}$H$_{55}$N$_3$O$_{22}$H$^+$ 822.3350, found 822.3357.

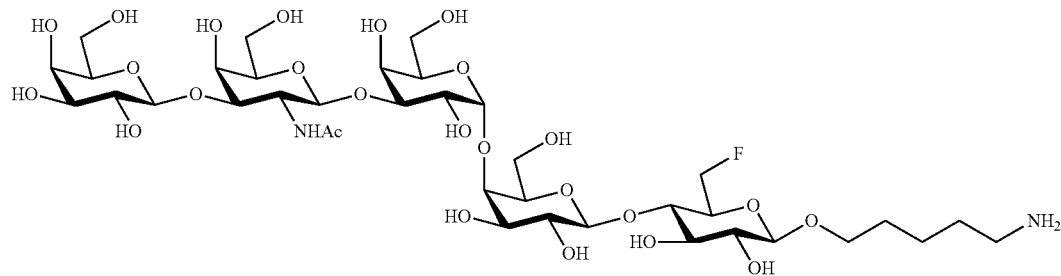

26

5-aminopentyl β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-deoxy-6-fluoro-β-D-glucopyranoside (26)

$^1$H NMR (600 MHz, D$_2$O) δ 4.97-4.84 (m, 2H), 4.71 (d, J=8.5 Hz, 1H), 4.54 (d, J=8.0 Hz, 1H), 4.51 (d, J=7.8 Hz, 1H), 4.46 (d, J=7.8 Hz, 1H), 4.40 (t, J=6.4 Hz, 1H), 4.26 (d, J=2.7 Hz, 1H), 4.19 (d, J=3.0 Hz, 1H), 4.11-4.03 (m, 2H), 3.95 (m, 6H), 3.91-3.50 (m, 18H), 3.33 (t, J=8.7 Hz, 1H), 2.98 (m, 2H), 2.04 (s, 3H), 1.70-1.67 (m, 4H), 1.54-1.33 (m, 2H). $^{19}$F NMR (471 MHz, D$_2$O) δ −234.85 (td, J=47.0, 28.2 Hz). $^{13}$C NMR (150 MHz, D$_2$O) δ 175.11, 104.79, 103.31, 102.89, 102.13, 100.38, 81.92, 80.80, 79.55, 78.63, 77.45, 77.41, 77.19, 75.40, 74.98, 74.59, 74.29, 73.34, 73.22, 72.89, 72.43, 72.08, 72.03, 70.82, 70.57, 70.28, 70.25, 68.90, 68.55, 67.97, 67.58, 62.45, 60.98, 60.94, 60.34, 60.31, 51.48, 39.43, 28.19, 26.91, 22.25, 22.09. HRMS (ESI-TOF, MH$^+$) calcd for C$_{37}$H$_{65}$FN$_2$O$_{25}$H$^+$ 957.3933, found 957.3969.

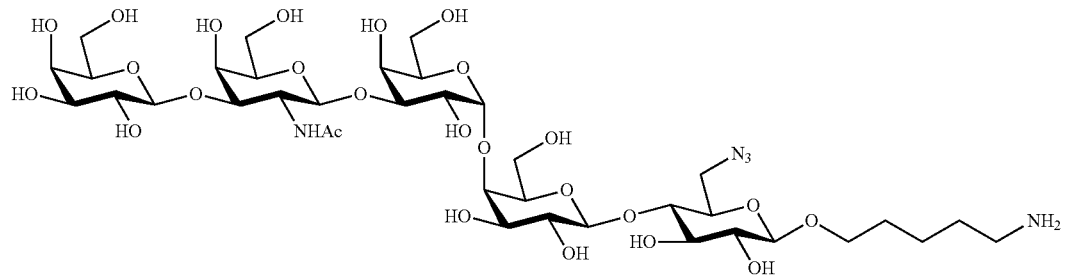

27

5-aminopentyl β-D)-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-azido-6-deoxy-β-D-glucopyranoside (27)

$^1$H NMR (600 MHz, D$_2$O) δ 4.94 (d, J=3.7 Hz, 1H), 4.72 (d, J=8.6 Hz, 1H), 4.56 (d, J=8.0 Hz, 1H), 4.52 (d, J=7.8 Hz, 1H), 4.48 (d, J=7.8 Hz, 1H), 4.40 (t, J=6.4 Hz, 1H), 4.28 (d, J=2.0 Hz, 1H), 4.21 (d, J=2.8 Hz, 1H), 4.16-4.04 (m, 2H), 4.04-3.89 (m, 7H), 3.89-3.51 (m, 19H), 3.35 (t, J=8.5 Hz, 1H), 3.02 (t, J=7.6 Hz, 2H), 2.05 (s, 3H), 1.79-1.68 (m, 4H)), 1.49-1.47 (m, 2H). $^{13}$C NMR (150 MHz, CDCl$_3$) δ 180.40, 110.09, 108.73, 108.18, 107.26, 105.66, 84.95, 84.85, 83.94, 82.43, 80.76, 80.27, 79.89, 79.61, 78.98, 78.20, 77.73, 77.38, 76.13, 75.87, 75.55, 75.50, 74.20, 73.85, 73.26, 72.87, 66.28, 66.23, 65.64, 65.59, 56.78, 55.67, 44.64, 33.48, 31.75, 27.55, 27.39. HRMS (ESI-TOF, MH$^+$) calcd for C$_{37}$H$_{65}$N$_5$O$_{25}$H$^+$ 980.4041, found 980.4080.

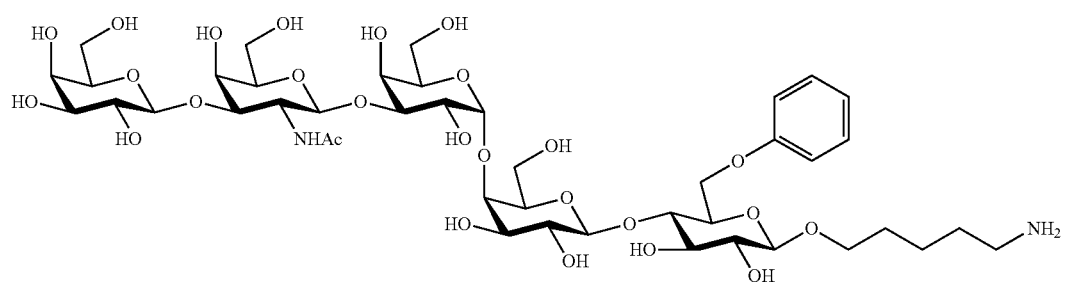

28

5-aminopentyl β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-O-phenyl-β-D-glucopyranoside (28)

$^1$H NMR (600 MHz, D$_2$O) δ 7.43 (t, J=7.2 Hz, 2H), 7.11 (d, J=8.2 Hz, 3H), 4.91 (d, J=3.5 Hz, 1H), 4.71 (t, J=8.3 Hz, 1H), 4.56 (t, J=7.6 Hz, 1H), 4.48-4.36 (m, 5H), 4.26 (s, 1H), 4.20 (a, 1H), 4.09 (t, J=10.1 Hz, 1H), 3.98-3.63 (m, 22H), 3.59-3.51 (m, 3H), 3.39 (t, J=8.3 Hz, 1H), 2.91 (m, 2H), 2.05 (s, 3H), 1.67 (m, 4H), 1.45 (m, 2H). $^{13}$C NMR (150 MHz, D$_2$O) δ 177.87, 160.55, 132.68, 124.57, 117.82, 107.55, 105.96, 105.64, 104.97, 103.10, 82.31, 81.37, 80.57, 79.91, 78.24, 77.74, 77.34, 77.15, 75.83, 75.77, 75.20, 74.79, 73.40, 73.33, 73.00, 71.66, 71.31, 70.72, 70.32, 68.65, 65.21, 63.74, 63.69, 63.10, 54.23, 42.28, 31.01, 30.15, 25.01, 24.87. HRMS (ESI-TOF, MH$^+$) calcd for C43 H70 N2 O26+H: 1031.4290, found 1031.4300.

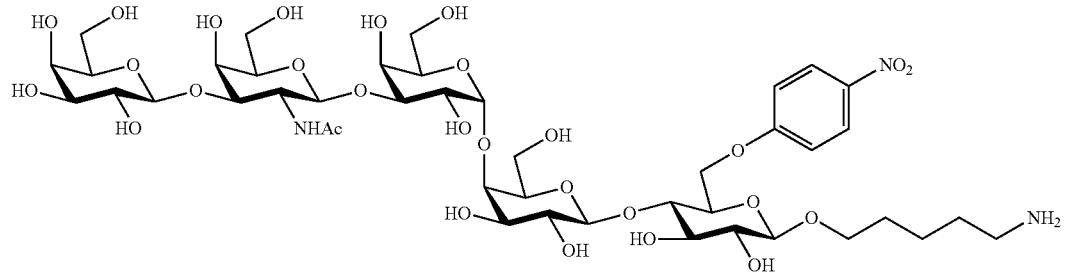

29

5-aminopentyl β-D-galactopyranosyl-(1→3)-2-acet-amido-2-deoxy-β-D-galactopyranosyl-(1→3)-α-D-Galactopyranosyl-(1→4)-β-D-galactopyranosyl-(1→4)-6-O-p-nitrophenyl-β-D-glucopyranoside (29)

$^1$H NMR (600 MHz, D$_2$O) δ 8.30 (d, J=9.3 Hz, 2H), 7.20 (d, J=9.3 Hz, 2H), 4.91 (d, J=3.6 Hz, 1H), 4.71 (d, J=8.5 Hz, 1H), 4.57 (d, J=5.8 Hz, 3H), 4.47 (d, J=7.7 Hz, 1H), 4.41-4.33 (m, 2H), 4.26 (s, 1H), 4.20 (d, J=2.6 Hz, 1H), 4.00 (m, 1H), 3.93-3.62 (m, 21H), 3.59-3.53 (m, 3H), 3.38 (t, J=8.8 Hz, 2H), 2.88 (t, J=7.3 Hz, 2H), 2.04 (s, 3H), 1.58 (m, 4H), 1.42-1.25 (m, 2H). $^{13}$C NMR (150 MHz, D$_2$O) δ 175.10, 163.52, 141.49, 126.21, 115.07, 104.80, 103.47, 102.87, 102.22, 100.34, 79.55, 78.60, 78.15, 77.07, 75.52, 74.98, 74.59, 74.39, 72.97, 72.81, 72.44, 72.06, 70.65, 70.57, 70.24, 70.20, 68.90, 68.55, 67.97, 67.56, 66.35, 60.98, 60.94, 60.33, 51.49, 39.41, 28.21, 26.92, 22.26, 22.10. HRMS (ESI-TOF, MH$^+$) calcd for C$_{43}$H$_{69}$N$_3$O$_{28}$H$^+$ 1076.4140, found 1076.4135.

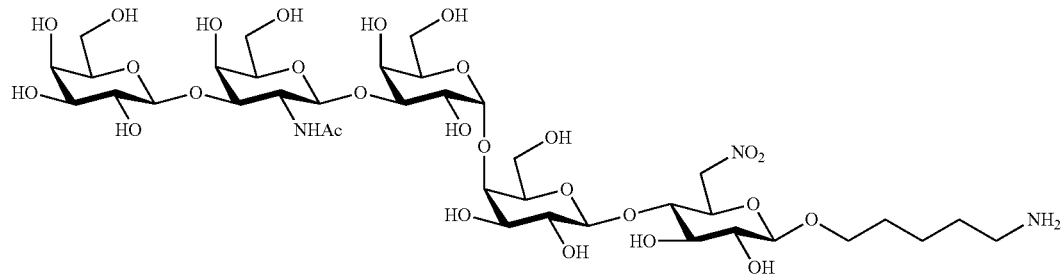

5-aminopentyl β-D-galactopyranosyl-(1→3)-2-acet-amido-2-deoxy-β-D-galactopyranosyl-(1→3)-α-D-Galactopyranosyl-(1→4)-β-D-galactopyranosyl-(1→4)-6-deoxy-6-nitro-β-D-glucopyranoside (30)

$^1$H NMR (600 MHz, D$_2$O) δ 4.93 (d, J=6.9 Hz, 1H), 4.70 (t, J=9.1 Hz, 1H), 4.60-4.51 (m, 2H), 4.47 (d, J=7.8 Hz, 1H), 4.43-4.28 (m, 2H), 4.27 (d, J=2.4 Hz, 1H), 4.20 (d, J=2.6 Hz, 1H), 4.17 (d, J=2.5 Hz, 1H), 4.07-3.97 (m, 3H), 3.97-3.49 (m, 22H), 3.41-3.28 (m, 1H), 3.01 (t, J=7.2 Hz, 2H), 2.04 (s, 3H), 1.86-1.55 (m, 4H), 1.63-1.25 (m, 3H). $^{13}$C NMR (150 MHz, D$_2$O) δ 175.10, 104.79, 103.45, 102.91, 102.09, 100.36, 79.83, 79.54, 78.67, 77.06, 75.53, 74.98, 74.59, 74.24, 72.71, 72.43, 72.08, 71.15, 71.09, 70.78, 70.61, 70.57, 70.26, 68.89, 68.54, 67.96, 67.58, 60.97, 60.93, 60.34, 60.23, 51.47, 39.29, 28.19, 26.35, 22.26, 22.01. HRMS (ESI-TOF, MH$^+$) calcd for C$_{37}$H$_{65}$N$_3$O$_{27}$H$^+$ 984.3878, found 984.3864.

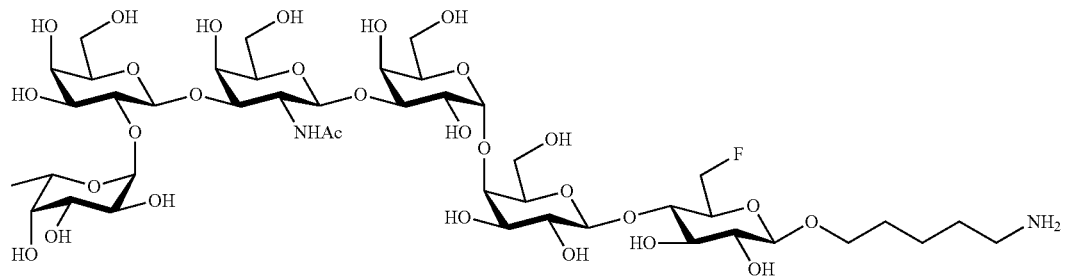

5-aminopentyl α-L-fucopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-deoxy-6-fluoro-β-D-glucopyranoside (Compound 2)

$^1$H NMR (600 MHz, D$_2$O) δ 5.25 (d, J=2.6 Hz, 1H), 4.92 (d, J=3.7 Hz, 2H), 4.84-4.74 (m, 1H), 4.65 (d, J=7.6 Hz, 1H), 4.56 (d, J=7.6 Hz, 1H), 4.55 (d, J=9.8 Hz, 1H), 4.52 (d, J=7.7 Hz, 1H), 4.41 (t, J32 6.5 Hz, 1H), 4.28 (m, 2H), 4.07 (d, J=3.1 Hz, 1H), 4.13-3.64 (m, 32H), 3.34 (t, J=8.5 Hz, 1H), 2.99 (t, J=7.5 Hz, 2H), 2.07 (s, 3H), 1.75-1.64 (m, 4H), 1.55-1.43 (m, 2H). $^{19}$F NMR (470 MHz, CDCl$_3$) δ −234.87 (td, J=47.0, 32.9 Hz). $^{13}$C NMR (150 MHz, D$_2$O) δ 174.28, 103.95, 103.33, 102.15, 102.04, 100.45, 99.27, 81.94, 81.72, 80.83, 78.23, 77.49, 77.46, 77.21, 76.36, 76.11, 75.46, 75.07, 74.63, 74.31, 73.58, 73.36, 73.24, 72.91, 72.10, 71.85, 70.83, 70.29, 70.16, 69.52, 69.18, 69.11, 68.48, 68.02, 67.83, 66.79, 60.98, 60.96, 60.36, 51.65, 39.43, 28.21. 26.84, 22.25, 22.10, 15.31. HRMS (ESI-TOF, MH$^+$) calcd for C$_{43}$H$_{75}$FN$_2$O$_{29}$H$^+$ 1103.4512, found 1103.4549.

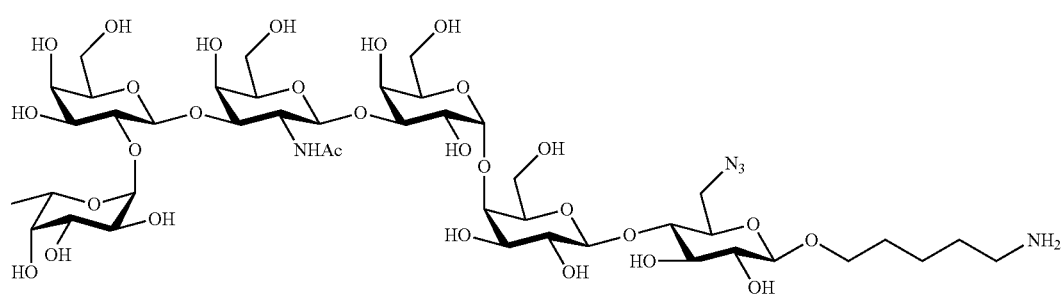

3

5-aminopentyl α-L-fucopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-azido-6-deoxy-β-D-glucopyranoside (Compound 3)

$^1$H NMR (600 MHz, D$_2$O) δ 5.26 (d, J=4.1 Hz, 1H), 4.92 (d, J=4.0 Hz, 1H), 4.64 (d, J=7.7 Hz, 1H), 4.57 (d, J=7.8 Hz, 1H) 4.55 (d, J=8.1 Hz, 1H), 4.50 (d, J=7.7 Hz, 1H), 4.41 (t, J=6.6 Hz, 1H), 4.34-4.23 (m, 21H), 4.13 (d, J=2.5 Hz, 1H), 4.09-3.57 (m, 31H), 3.35 (t, J=8.5 Hz, 1H), 3.06-2.99 (m, 2H), 2.07 (s, 3H), 1.77-1.63 (m, 4H), 1.53-1.41 (m, 2H), 1.24 (d, J=6.6 Hz, 3H). $^{13}$C NMR (150 MHz, D$_2$O) δ 177.02, 106.70, 106.20, 104.79, 104.72, 103.18, 102.02, 82.42, 80.99, 79.88, 79.11, 78.85, 78.27, 77.81, 77.37, 77.07, 76.44, 76.33, 75.66, 74.84, 74.59, 73.57, 72.96, 72.89, 72.26, 71.91, 71.85, 71.22, 70.77, 70.56, 69.53, 63.73, 63.70, 63.10, 54.39, 53.13, 42.09, 30.94, 29.17, 24.99, 24.85, 18.05. HRMS (ESI-TOF, MH$^+$) calcd for C$_{43}$H$_{75}$N$_5$O$_{29}$H$^+$ 1126.4620, found 1126.4639.

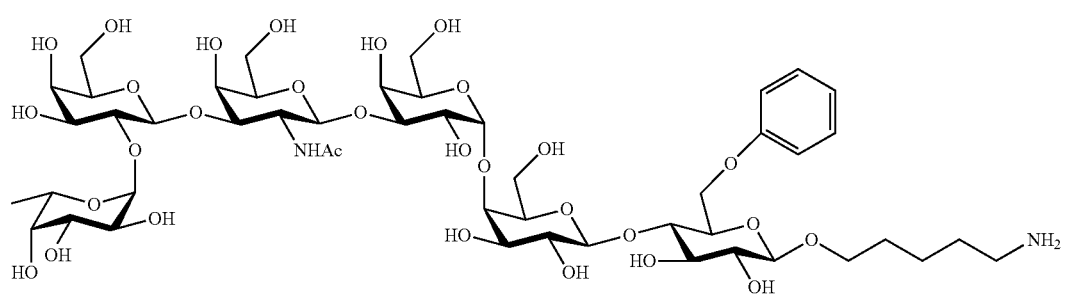

4

5-aminopentyl α-L-fucopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-O-phenyl-β-D-glucopyranoside (Compound 4)

$^1$H NMR (600 MHz, D$_2$O) δ 7.43 (t, J=8.0 Hz, 2H), 7.11 (t, J=8.0 Hz, 3H), 5.26 (d, J=4.1 Hz, 1H), 4.89 (d, J=4.0 Hz, 1H), 4.64 (d, J=7.7 Hz, 1H), 4.57 (d, J=7.6 Hz, 1H), 4.55 (d, J=8.0 Hz, 1H), 4.48 (d, J=10.1 Hz, 1H), 4.45-4.34 (m, 3H), 4.27-4.24 (m, 2H), 4.13 (d, J=2.1 Hz, 1H), 4.06-3.62 (m, 27H), 3.58-3.50 (m, 2H), 3.39 (dd, J=9.3, 8.2 Hz, 1H), 2.91 (t, J=7.4 Hz, 2H), 2.07 (s, 3H), 1.73-1.60 (m, 4H), 1.51-1.39 (m, 2H), 1.24 (d, J=6.6 Hz, 3H). $^{13}$C NMR (150 MHz, D$_2$O) δ 174.28, 157.80, 129.93, 121.82, 115.08, 103.95, 103.24, 102.23, 102.05, 100.40, 99.28, 78.22, 77.85, 77.14, 76.36, 76.11, 75.54, 75.07, 74.62, 74.42, 73.58, 73.09, 73.04, 72.05, 71.85, 70.64, 70.28, 70.13, 69.52, 69.17, 69.11, 68.48, 68.02, 67.81, 66.78, 65.91, 60.98, 60.95, 60.38, 60.35, 51.64, 39.56, 28.27, 27.49, 22.25, 22.13, 15.31. HRMS (ESI-TOF, MH$^+$) calcd for C49H80N2O30H$^+$ 1177.4869, found 1177.4918.

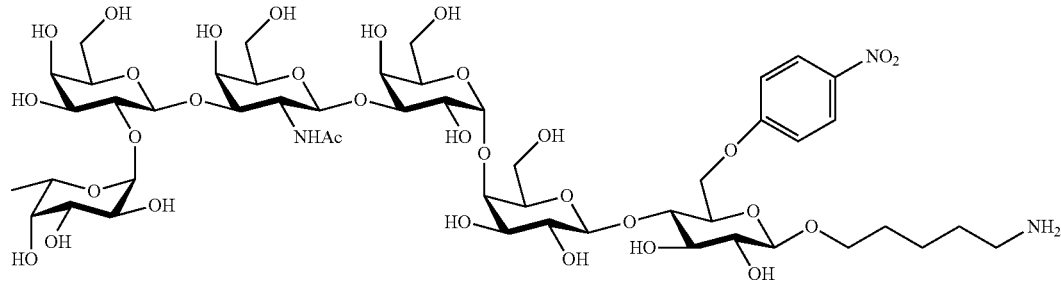

5

5-aminopentyl α-L-fucopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-O-p-nitrophenyl-β-D-glucopyranoside (Compound 5)

$^1$H NMR (600 MHz, D$_2$O) δ 8.30 (d, J=8.8 Hz, 2H), 7.21 (d, J=8.8 Hz, 2H), 5.26 (d, J=4.1 Hz, 1H), 4.89 (d, J=3.6 Hz, 1H), 4.65 (d, J=7.6 Hz, 1H), 4.60 (m, 3H), 4.39 (m, 2H), 4.25-4.21 (m, 1H), 4.13 (s, 1H), 4.01-3.65 (m, 28H), 3.59-3.56 (m, 3H), 3.45-3.35 (m, 1H), 2.94 (t, J=6.9 Hz, 2H), 2.07 (s, 3H), 1.66-1.62 (m, 4H), 1.44-1.42 (m, 2H), 1.24 (d, J=6.3 Hz, 3H). $^{13}$C NMR (150 MHz, D$_2$O) δ 177.03, 166.29, 144.26, 128.97, 117.83, 106.69, 106.25, 104.98, 104.79, 103.15, 102.02, 80.94, 79.82, 79.10, 78.85, 78.31, 77.81, 77.37, 77.16, 76.32, 75.73, 75.56, 74.82, 74.78, 74.59, 73.40, 72.97, 72.88, 72.26, 71.91, 71.86, 71.22, 70.77, 70.55, 69.53, 69.12, 65.21, 63.73, 63.70, 63.09, 54.39, 42.19, 30.97, 24.99, 24.86, 18.05. FIRMS (ESI-TOF, MH$^+$) calcd for C$_{49}$H$_{79}$N$_3$O$_{32}$H$^+$ 1222.4719, found 1222.4729.

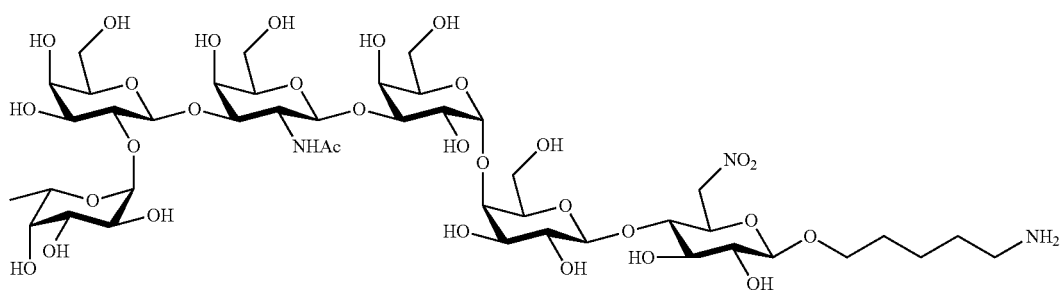

6

5-aminopentyl α-L-fucopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-6-deoxy-6-nitro-β-D-glucopyranoside (Compound 6)

$^1$H NMR (600 MHz, D$_2$O) 5.26 (s, 1H), 4.91 (s, 1H), 4.69-4.52 (m, 5H), 4.42 (d, J=6.4 Hz, 1H), 4.34 (d, J=7.5 Hz, 1H), 4.26 (m, 2H), 4.13 (s, 1H), 4.12-3.62 (m, 28H), 3.57 (m, 1H), 3.34 (t, J=8.3 Hz, 1H), 3.02 (t, J=6.1 Hz, 2H), 2.07 (s, 3H), 1.80-1.62 (m, 4H), 1.47 (dt, J=22.4, 7.5 Hz, 2H), 1.24 (d, J=6.4 Hz, 3H). HRMS (ESI-TOF, MH$^+$) calcd for C$_{43}$H$_{75}$N$_3$O$_{31}$H$^+$1130.4457, found 1130.4438.

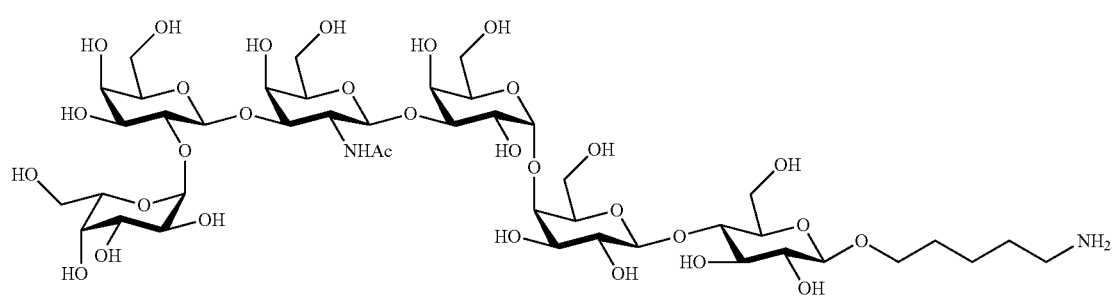

5-aminopentyl α-L-galactopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-β-D-glucopyranoside (Compound 7)

$^1$H NMR (600 MHz, D$_2$O) δ 5.40 (d, J=3.9 Hz, 1H), 4.92 (d, J=3.7 Hz, 1H), 4.65 (d, J=7.7 Hz, 1H), 4.61 (d, J=7.4 Hz, 1H), 4.53 (d, J=7.7 Hz, 1H), 4.50 (d, J=8.0 Hz, 1H), 4.41 (t, J=6.4 Hz, 1H), 4.34-4.24 (m, 2H), 4.15-3.56 (m, 34H), 3.33 (t, J=8.3 Hz, 1H), 2.97 (t, J=7.5 Hz, 2H), 2.09 (s, 3H), 1.74-1.66 (m, 41H), 1.49-1.42 (m, 2H). $^{13}$C NMR (150 MHz, D$_2$O) δ 174.45, 103.70, 103.30, 102.02, 101.95, 100.42, 98.45, 78.77, 78.40, 77.16, 76.09, 75.47, 75.15, 74.79, 74.58, 74.52, 74.50, 73.71, 72.93, 72.09, 70.85, 70.24, 70.14 (2C), 69.44, 69.20, 69.17, 69.06, 68.43, 68.28, 67.75, 61.76, 60.96, 60.89, 60.33, 60.03, 51.49, 39.47, 28.20, 27.12, 22.30, 22.12. HRMS (ESI-TOF, MH$^+$) calcd for C$_{43}$H$_{76}$N$_2$O$_{31}$H$^+$ 1117.4505, found 1117.4488.

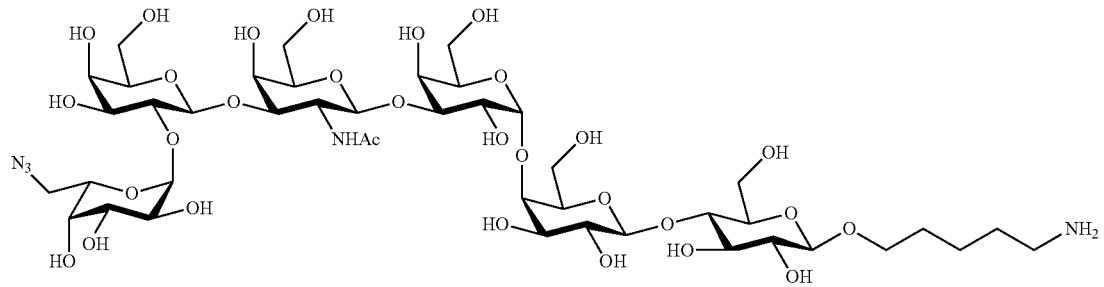

5-aminopentyl 6-azido-6-deoxy-α-L-galactopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-β-D-glucopyranoside (Compound 8)

$^1$H NMR (600 MHz, D$_2$O) δ 5.46 (d, J=3.8 Hz, 1H), 4.92 (d, J=3.5 Hz, 1H), 4.65 (d, J=7.5 Hz, 1H), 4.60 (d, J=8.3 Hz, 1H), 4.53 (d, J=7.7 Hz, 1H), 4.53 (d, J=8.0 Hz, 1H), 4.41 (t, J=6.4 Hz, 1H), 4.34-4.24 (m, 2H), 4.18 (s, 1H), 4.09-3.59 (m, 32H), 3.33 (t, J=8.1 Hz, 2H), 2.99 (t, J=7.4 Hz, 2H), 2.08 (s, 3H), 1.78-1.64 (m, 4H), 1.55-1.44 (m, 2H). $^{13}$C NMR (150 MHz, D$_2$O) δ 174.36, 103.87, 103.30, 102.29, 101.95, 100.42, 98.41, 78.79, 78.35, 77.17, 76.95, 75.48, 75.11, 74.79, 74.67, 74.53, 74.43, 73.85, 72.93, 72.09, 70.85, 70.15, 70.12, 69.67, 69.61, 69.14, 69.08, 69.05, 68.56, 68.02, 67.78, 60.95, 60.91, 60.33, 60.04, 51.40, 51.25, 39.44, 28.19, 26.96, 22.32, 22.10. HRMS (ESI-TOF, MH$^+$) calcd for C$_{43}$H$_{75}$N$_5$O$_{30}$H$^+$ 1142.4570, found 1142.4569.

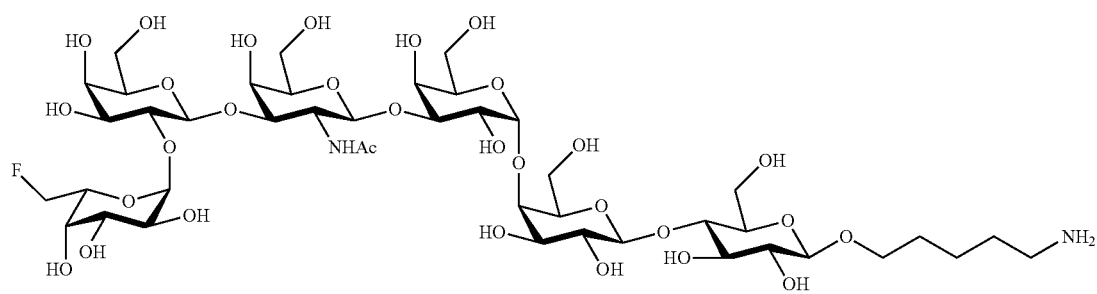

9

5-aminopentyl 6-deoxy-6-fluoro-α-L-galactopyranosyl-(1→2)-β-D-galactopyranosyl-(1→3)-2-acetamido-2-deoxy-β-D-galactopyranosyl-(3→3)-α-D-Galactopyranosyl-(1→4)-β-D-galactopyranosyl-(1→4)-β-D-glucopyranoside (Compound 9)

$^1$H NMR (600 MHz, D$_2$O) δ 5.40 (d, J=3.9 Hz, 1H), 4.91 (d, J=3.9 Hz, 1H), 4.69 (m, 1H), 4.64-4.60 (m, 2H), 4.57 (d, J=8.2 Hz, 1H), 4.52 (d, J=7.8 Hz, 1H), 4.49 (d, J=8.0 Hz, 1H), 4.39 (m, 2H), 4.26 (d, J=2.4 Hz, 1H), 4.12 (d, J=2.7 Hz, 1H), 4.09-3.56 (nm, 311H), 3.32 (t, J=8.5 Hz, 1H), 2.99 (t, J=7.4 Hz, 2H), 2.07 (s, 3H), 1.71-1.66 (m, 4H), 1.49-1.44 (m, 2H). $^{13}$C NMR (150 MHz, D$_2$O) δ 174.38, 103.84, 103.30, 102.05, 101.95, 100.43, 98.98, 83.96, 82.86, 78.79, 78.27, 77.16, 76.69, 75.65, 75.48, 75.09, 74.79, 74.52, 74.47, 73.65, 72.93, 72.09, 70.85, 70.14, 70.12, 69.11, 68.96, 68.36, 68.05, 67.80, 60.95, 60.90, 60.34, 60.03, 51.45, 39.43, 28.18, 26.89, 22.28, 22.10. HRMS (ESI-TOF, MH$^+$) calcd for C$_{43}$H$_{75}$FN$_2$O$_{30}$H$^+$ 1119.4461, found 1119.4459.

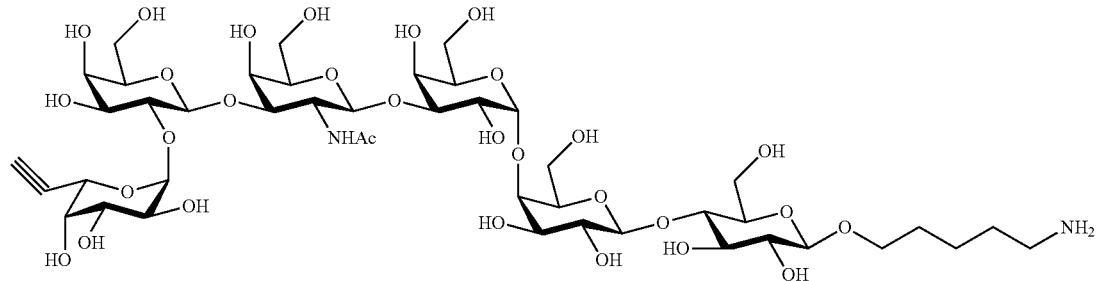

10

5-aminopentyl 6-acetylenyl-6-deoxy-α-L-galactopyranosyl-(1→2)-β-D-galactopyranosyl-(1→3)-2-acetamido-2-deoxy-β-D-galactopyranosyl-(1→3)-α-D-Galactopyranosyl-(1→4)-β-D-galactopyranosyl-(1→4)-β-D-glucopyranoside (Compound 10)

$^1$H NMR (600 MHz, D$_2$O) δ 5.32 (d, J=4.0 Hz, 1H), 4.91 (d, J=3.0 Hz, 2H), 4.64 (d, J=7.7 Hz, 1H), 4.59 (d, J=8.4 Hz, 1H), 4.53 (d, J=7.7 Hz, 1H), 4.50 (d, J=8.0 Hz, 1H), 4.40 (t, J=6.5 Hz, 1H), 4.26 (d, J=2.8 Hz, 1H), 4.17-4.13 (m, 2H), 4.05-3.58 (m, 32H), 3.32 (t, J=8.5 Hz, 1H), 3.02 (m, 2H), 2.07 (s, 3H), 1.77-1.64 (m, 41H), 1.53-1.43 (m, 2H), $^{13}$C NMR (150 MHz, D$_2$O) δ 177.06, 106.53, 106.04, 104.69, 104.60, 103.17, 102.13, 81.52, 80.89, 79.91, 79.26, 78.87, 78.79, 78.22, 77.88, 77.54, 77.27, 77.19, 76.13, 75.67, 74.83, 74.77, 73.69, 73.59, 72.89, 72.81, 71.86, 71.83, 71.28, 71.19, 70.59, 70.21, 65.69, 65.19, 63.68, 63.64, 63.08, 62.77, 54.26, 42.06, 30.89, 29.13, 25.00, 24.81. HRMS (ESI-TOF, MH$^+$) calcd for C$_{44}$H$_{74}$N$_2$O$_{30}$H$^+$ 1111.4399, found 1111.4397.

Example 5: Immunogenicity Study of the GH Derivatives DT-Conjugates

To investigate the immunogenicity of the GH derivatives DT-conjugates (1-DT to 10-DT), five female BALB/c mice were immunized intramuscularly with 2 μg of GH derivatives DT-conjugates and 2 μg of the glycolipid adjuvant C34 three times at biweekly intervals. In the previous study, the anti-GH antibodies titer was low with GH-protein conjugates alone without any adjuvants.[13b] The antisera from each immunogen were obtained ten days after the third immunization and were tested on the glycan microarray containing 94 chemically synthesized glycans, including GH 1, GH derivatives 2-10. GH derivatives fragments 11-30 and other tumor-associated carbohydrate antigens (Table S1 in SI). Because some chemical modifications were carried out on the glycan, some functional linkers were also included in the glycan array to check the cross reactivity.

Antibodies induced by the GH derivatives DT-conjugates (1-DT to 10-DT) were specifically recognized by GH, GH derivatives and GH fragments but not by other TACAs and functional linkers. GH, Gb5 and SSEA4 were selected as standard antigens for all DT-conjugates (FIG. 1A-C). The sera obtained from these glycoconjugates induced high IgG antibody titers, indicating a T-cell-dependent immune response. Interestingly, no significant IgM production was observed for all GH-Lac or Fuc derivatives. Regarding the IgG level against GH, the titers of antibodies induced by GH-N$_3$-DT (3-DT) and N$_3$-GH-DT (8-DT) were much higher than the nature form GH-DT conjugate (1-DT), and the titers of antibodies induced by GH-F-DT (2-DT) and Gl-phenyl-DT (4-DT) were comparable to the nature form GH-DT conjugate (1-DT). The azido group appears to be an immune modulator as GH-N$_3$-DT (3-DT) and N$_3$-GH-DT (8-DT) provide good titers. The reason for the enhancement of immunogenicity is unknown, but the N$_3$ property on the glycan of GH-N$_3$ or N$_3$-GH 8 compared to nature GH may play a critical role. The immunogenicity modulation by the fluoro (F) group on GH is regioselective.[19c,33] The F moiety at the C-6 position of Glc at the reducing end of GH could induce comparable titer to nature GH, but the titer induced by the F group at the C-6 position of Fuc at the non-reducing end of GH showed a lower reaction with GH. Interestingly, antibodies induced by GH-phenyl-DT (4-DT) can cross react with GH. This cross immunogenicity is inconsistent with the previous report that no cross-reaction with nature GM3 and STn was formed with the use of N-phenylacetyl GM3 or STn based vaccines.[19a,20] The immunogen GH-phenylNO$_2$-DT (5-DT), GH-NO$_2$-DT (6-DT), OH-GH-DT (7-DT), F-GH-DT (9-DT) and acetylenyl-GH-DT (10-DT) gave weak response to GH. Moreover, GH-phenylNO$_2$-DT (5-DT) and GH-NO$_2$-DT (6-DT) elicited strong immune response to the phenylNO$_2$ and the NO$_2$ sugar analogs but not to the nature form GH analogs. This result is also inconsistent with the previous report that a single p-phenylNO$_2$ mutation on TNF-α induces robust antibodies to recognize wild type TNF-α.[21a] Interestingly, antibodies induced by these glycoconjugates also showed the same pattern in recognizing Gb5 and SSEA4 (FIGS. 1B-C). Therefore, we concluded that modification at the C-6 position of reducing end glucose of Globo H with the fluoro, azido or phenyl group elicited robust IgG antibody response to specifically recognize Globo H, Gb5 and SSEA. However, only the modification of Globo H with the azido group at the C-6 position of the non-reducing end fucose could elicit strong IgG immune response. See Lee et al., J. Am. Chem. Soc. 2014, 136, 16844-16853, which is incorporated herein by reference in its entirety.

Further analysis of the antibody isotypes of the IgG subclasses of antisera from these vaccines using the glycan array showed that the antibodies have a significant amount of IgG1, IgG2b, IgG2c and IgG3 and low level of IgG2a. Moreover, the IgG1 subclass was the highest in the antisera with a high level of IgG3 antibody, which is a typical anti-carbohydrate response and is consistent with a T cell-mediated immunity.

The capabilities of the mouse antisera induced by GH-DT (1-DT), GH-F-DT (2-DT), GH-N$_3$-DT (3-DT), GH-phenyl-DT (4-DT) and N$_3$-GH-DT (8-DT) to recognize the GH-expressing MCF7 human breast cancer cell lines were examined by flow cytometry (FIG. 2). As expected, the antiserum elicited by GH-DT (1-DT) was significantly reactive with GH-positive MCF7 cells compared with the antisera from untreated mouse. MCF7 cells were also specifically recognized by the antisera elicited by GH derivatives-DT (2-DT, 3-DT, 4-DT and 8-DT).

Example 6: Complement-Dependent Cytoxicity of the GH Derivatives DT-Conjugates

Figure 3:
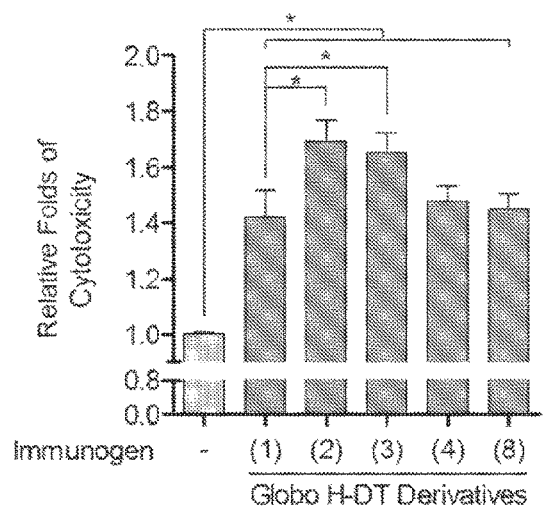
FIG. 3 shows that the antibodies elicited by GH derivatives mediate complement-dependent cytotoxicity (CDC) to eliminate GH-expressing tumor cells.

Complement-dependent cytoxicity (CDC) was studied by OH-expressing MCF7 cancer cells (FIG. 3). MCF-7 cells were seeded into 96-well cell culture plate with a density of 10$^4$ cells per well. After an overnight culture at 37° C., the culture medium was replaced by 100 μL of antiserum/complement mixture, and then incubated at 37° C. for 2 hours. To prepare the antiserum/complement mixture, the antiserum was diluted 20 times in culture medium supplemented with 20% of rabbit complement (Life Technologies). Following the incubation, the cytotoxicity induced by the antiserum was determined using the CytoTox 96® Non-Radioactive Cytotoxicity Assay kit (Promega, Fitchburg, Wis.) according to manufacturer's instruction. The relative fold of cytotoxicity induced by the antiserum was normalized to the cytotoxicity caused by the serum from so the untreated Blab/c mouse.

The antisera obtained from immunization with GH-DT (1-DT), GH-F-DT (2-DT), GH-N$_3$-DT (3-DT), GH-phenyl-DT (4-DT) and N$_3$-GH-DT (8-DT) were able to significantly induce cancer cell cytotoxicity compared with the sera from untreated mouse. The cell cytotoxicity of the antisera obtained from GH-phenyl-DT (4-DT) and N$_3$-GH-DT (8-DT) were comparable to the nature form GH-DT (1-DT).

Interestingly, the antisera derived from GH-F-DT (2-DT) or GH-N$_3$-DT (3-DT) vaccine could induce more than 15% higher cancer cell cytotoxicity comparing to GH-DT (1-DT), suggesting that these derivatives have a potential to be used as a better therapeutic vaccine.

This invention has established a strategy for the chemoenzymatic synthesis of GH derivatives and their immunogenic conjugates. The immunological properties of GH derivative conjugates were evaluated using a glycan array and compared to the nature form GH-DT (1-DT). The results showed that modification at the reducing end of Globo H with the fluoro, azido or phenyl group elicited strong IgG antibody response to specifically recognize Globo H, Gb5 and SSEA4, but only the azido-fucose derivative of Globo H could elicit strong IgG immune response. Moreover, antibodies induced by GH-DT (1-DT), GH-F-DT (2-DT), GH-N$_3$-DT (3-DT), GH-phenyl-DT (4-DT) and N$_3$-GH-DT (8-DT) recognized GH expressing tumor cells (MCF-7) and could mediate the complement-dependent cell cytotoxicity against tumor cells. GH-F-DT (2-DT) and GH-N$_3$-DT (3-DT) vaccines have higher cancer cell cytotoxicity compared with GH-DT (1-DT), providing for a new generation of vaccines based on modification of carbohydrate antigen structures.

General Methods, Materials and Instrumentation

All chemicals and reagents were purchased from Acros, Echo chemical, Merck Sigma-Aldrich, Fluka and used without further purification. All reactions involving air or moisture-sensitive reagents or intermediates were performed under an argon atmosphere. Molecule sieve 4 Å (Acros) was dried with heater under high vacuum. The progress of reactions was monitored by thin-layer chromatography on silica gel 60 F$_{254}$ plate (2 mm, Merck) and visualized under UV illumination and by staining with acid ceric ammonium molybdate or p-anisaldehyde. Flash column chromatography was performed on silica gel (40-63 μm, Merck) or LiChroprep RP-18 (40-63 μm, Merck). Dialysis membrane (Cellulose Ester, MCCO=10,000) was washed by ddH2O before use. NMR spectra were recorded at 600 MHz ($^1$H NMR) and 150 MHz ($^{13}$C HMR) spectrometers in a Brüker Advance 600. The chemical shift was reported in ppm (δ scale) and was calibrated against the residual proton and carbon signal of deuterated chloroform (δ=7.24 ppm), deuterated water (δ=4.80 ppm) or deuterated methanol (δ=3.31 ppm). Coupling constants in Hz were calculated from chemical shift of $^1$H NMR or spectra. Data are represented as follows: chemical shift, multiplicity (s=singlet, d=doublet, t=triplet, q=quartet, m=multiplet, br=broad), intergration and coupling constant (J) in Hz, High resolution ESI mass spectra were recorded on a APEX-ultra 9.4 T FTICR-MS (Bruker Daltonics). MALDI-TOF specta were recorded on Bruker Ultraflex II TOF/TOF200 sepctrameter using sinapinic acid as the matrix. Alexa Fluor 647-conjugated goat anti-mouse IgG antibody, DyLight 649-conjugated goat anti-mouse IgM antibody, Alexa Fluor 488-conjugated goat anti-mouse IgG1 antibody, Alexa Flour 594-conjugated goat anti-mouse IgG2a antibody, Cy3-conjugated goat anti-mouse IgG2b antibody, R-PE-conjugated anti-mouse IgG2c antibody and Alexa Fluor 647-conjugated goat anti-mouse IgG3 antibody were purchased from Jackson Immunoresearch. The microarray slides were scanned at 635 nm, 594 nm, 532 nm, or 488 nm wavelength with a microarray fluorescence chip reader (GenePix 4300A; Molecular Devices Corporation). The fluorescence data were analyzed by GenePix Pro-6.0 software (Axon Instruments, Union City, Calif., USA). Diphtheria toxoid (CRM 197) was purchased from PFenex Incorporation.

All nucleotides, sugars, sugar nucleotides, and chemicals were purchased from Sigma-Aldrich (St. Louis, Mo.). Cloning, overexpression, purification and activity assay of All enzymes was described according to the reported procedures.[3]

General Procedure for Synthesis of GH-Derivative Monoester

A GH derivative (2-3 mg, 1 equiv) was dissolved in anhydrous dimethylformamide (DMF) solution. p-Nitrophenyl ester linker (5-6 mg, 5 equiv) was then added and stirred for 1-5 h at room temperature. The reaction was monitored by thin layer chromatography using 3:2:2 butanol/acetate/water as the developing solvent. When an optimal yield was achieved, the reaction mixture was concentrated in vacuo without heating to remove DMF. Purified by reverse phase (C18) column chromatography and gradually eluted with H$_2$O containing 1% acetic acid to MeOH:H2O=7:3. The solution was lyophilized to a light yellow solid GH-derivatives monoester (1.5-2 mg, 60~80%).

General Procedure for GH-Derivatives Glycoconjugates

DT was dissolved in 100 mM PBS buffer, pH 7.9 (5 mg/mL), and 30-40 equivalents of GH-derivative monoester were added to the solution. The mixture was stirred gently for 24 h at room temperature. The mixture was then diluted with ddH$_2$O and centrifuged against 10 changes of deionized water by Amicon Ultra-0.5, 10 kDa. The solution was lyphophilized to white powder. The obtained GH-derivative DT conjugates can be characterized by MALDI-TOF (positive mode, matrix sinapinic acid, H$_2$O) analysis to determine the oligosaccharide incorporation number.

Microarray Fabrication and Detection

To fabricate the microarray, compounds 1-30, 9 kinds of functional linkers and 55 kinds of other oligosaccharides with aminopentyl linker (Table S1) were prepared by dissolving in the printing buffer (300 mM phosphate buffer, 0.005% Tween 20, pH 8.5) in 10 mM concentration. Glycans were printed (BioDot; Cartesian Technologies) by robotic pin (SMP3; TeleChem International) deposition of ~0.6 nL of various solutions from 96-well plate onto NHS-coated glass slide (Nexterion H slide; SCHOTT North America). The microarray was designed 16 grids in one slide, and 20 columns×10 rows in one grid. Printed slides were allowed to react in an atmosphere of 80% humidity for one hour followed by desiccation overnight. These slides were stored at room temperature in a desiccator prior to use.

Cell Lines and Flow Cytometry Analysis

Human breast cancer cell line MCF-7 was maintained in Dulbecco's Modified Eagle Medium (Life Technologies, Carlsbad, Calif.) supplemented with 10% FBS, 1× Antibiotic-Antimycotic (Life Technologies) and insulin (50 mg/mL). For flow cytometry analysis, cells were harvested, spun at 500 g for 3 min, and resuspended in FACS staining/washing buffer (1% FBS, 0.1% NaN$_3$ in PBS). Cells (2.5× 10$^5$) were then incubated with antiserum (1/10 dilution in 50 μL of FACS staining/washing buffer) from Balb/c mice immunized with GH derivatives for 2 hours at 4° C. The serum from untreated Balb/c mouse was used as control here. After washing twice with 1 mL of FACS staining/washing buffer, cells were incubated with FITC-labeled anti-mouse IgG/IgM antibody (1/20 dilution, BD Biosciences, San Jose, Calif.) for 30 min at 4° C. After another washing cycle, cells were subjected to flow cytometric analysis. All the samples were analyzed with FACSCanto (Becton Dickinson, Franklin Lakes, N.J.) using FACSDiva software (Becton Dickinson) and FlowJo (Tree Star, Ashland, Oreg.).

Mice Dosage and Immunization Schedule

For comparing the immunogenicity of GH deverivative vaccines (1-DT to 10-DT), ten groups of five mice (8-week-old female Balb/c mice, BioLASCO, Taiwan) were immunized intramuscularly with glycolipid C34. Three immunizations were given at 2-week intervals. Each vaccination contained 2 µg GH derivatives and 2 µg C34. Control mice were injected with phosphate buffer saline (PBS). Mice were bled before the first immunization (preimmune) and 10 d after the third immunization. All of the sera were obtained by centrifugation at 4,000×g for 10 min. The serologic responses were analyzed by glycan microarray.

Serologic Assay with Glycan Array

Mouse sera were diluted with 1% BSA/PBST buffer (PBST buffer: PBS and 0.05% Tween-20, pH 7.4). The glycan microarray was blocked with Superblock blocking buffer (Pierce) for 1 h at 4° C. and washed three times with PBST buffer before use. The serum dilutions were then introduced to the glycan microarray and incubated at 4° C. for 1 h. Excess serum antibodies were washed out and the microarrays were incubated individually with Alexa Fluor 647-conjugated goat anti-mouse IgG antibody or DyLight 649-conjugated goat anti-mouse IgM antibody as the $2^{nd}$ antibody at 4° C. in dark for 1 h. The slides were then washed three times with PBST and scanned at 635 nm wavelength with a microarray fluorescence chip reader (GenePix 4300A; Molecular Devices Corporation) and scanned images were analyzed with GenePix Pro-6.0 analysis software (Axon Instruments, Union City, Calif., USA).

Antibody Subclasses Analysis.

The procedures for antibody subclasses analysis were the same as mentioned above. Alexa Flour 594-conjugated goat anti-mouse IgG2a antibody, Cy3-conjugated goat anti-mouse IgG2b antibody, R-PE-conjugated anti-mouse IgG2c antibody and Alexa Fluor 647-conjugated goat anti-mouse IgG3 antibody were separately adding into the microarray with 400 fold dilution, followed by incubation and washing.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

REFERENCES (1) Hakomori, S. *Adv Cancer Res* 1989, 52, 257.
(2) Hakomori. S. *Curr. Opin. Immunol.* 1991, 3, 646.
(3) (a) Astronomo, R. D.; Burton. D. R. *Nat. Rev. Drug Discovery* 2010, 9, 308. (b) Buskas. T.; Thompson, P.; Boons. G. *J. Chem. Commun.* 2009, 5335. (c) Wilson, R. M.; Danishefsky. S. J. *J. Am. Chem. Soc.* 2013, 135, 14462.
(4) Berti, F.; Adamo, R. *ACS Chem. Biol.* 2013, 81653.
(5) (a) Bundle, D. R.; Rich, J. R.; Jacques, S.; Yu, H. N.; Nitz, M.; Ling, C. C. *Angew. Chem. Int. Ed.* 2005, 44, 7725. (b) Wu, X.; Lipinski, T.; Paszkiewicz, E.; Bundle, D. R. *Chemistry* 2008, 14, 6474.
(6) (a) Lo-Man. R.; Vichier-Guerre. S.; Perraut, R.; Deriaud, E.; Huteau, V.; BenMohamed, L.; Diop, O. M.; Livingston, P. O.; Bay, S.; Leclerc, C. *Cancer Res.* 2004, 64, 4987. (b) Kagan, E., Ragupathi, G.; Yi, S. S.: Reis, C. A.; Gildersleeve, J.; Kahne. D.; Clausen, H.; Danishefsky, S. J.: Livingston, P. O. *Cancer Immunol. Immunother* 2005, 54, 424.
(7) Ragupathi. G.; Koide, F.; Livingston, P. O.; Cho, Y. S.; Endo. A.; Wan, Q.; Spassova, M. K.; Keding, S. J.; Allen, J.; Ouerfelli, O.; Wilson. R. M.; Danishefsky, S. *J. J. Am. Chem. Soc.* 2006, 128, 2715.
(8) (a) Ingale, S.; Wolfert, M. A.; Gackwad, J.; Buskas, T.; Boons, G. *J. Nat. Chem. Biol.* 2007, 3, 663. (b) Buskas, T.; Ingale, S.; Boons, G. *J. Angew Chem. Int. Ed.* 2005, 44, 5985.
(9) (a) Liu, C. C.; Ye. X. S. *Glycoconj J* 2012, 29, 259. (b) Yin, Z.; Huang, X. *J. Carbohydr. Chem.* 2012, 31, 143.
(10) (a) Miles, D.; Roche, H.; Martin, M.; Perren. T. J.; Cameron, D. A.; Glaspy. J.; Dodwell, D.; Parker, J.; Mayordomo, J.; Tres. A.; Murray, J. L.; Ibrahim, N. K.; Theratope Study, G. *Oncologist* 2011, 16, 1092. (b) Holmberg, L. A.; Sandmaier. B. M. *Expert Rev. Vaccines.* 2004, 3, 655. (c) Kirkwood, J. M.: Ibrahim. J.; Lawson, D. H.; Atkins, M. B.; Agarwala, S. S.; Collins, K.; Mascari, R.; Morrissey, D. M.; Chapman, P. B. *J Clin Oncol* 2001, 19, 1430. (d) Eggermont, A. M. *Nat Rev Clin Oncol* 2009, 6, 256.
(11) Bundle, D. R. *Nat. Chem. Biol.* 2007, 3, 605.
(12) (a) Kannagi, R.; Levery, S. B.; Ishigami, F.; Hakomori, S.; Shevinsky, L. H.; Knowles, B. B.; Solter, D. *J. Biol. Chem.* 1983, 258, 8934. (b) Menard, S.; Tagliabue, E.; Canevari, S.; Fossati, G.; Colnaghi, M. I. *Cancer Res.* 1983, 43, 1295. (c) Bremer, E. G.; Levery, S. B.: Sonnino, S.; Ghidoni, R.; Canevari, S.; Kannagi, R.; Hakomori, S. *J. Biol. Chem.* 1984, 259, 14773.
(13) (a) Canevari, S.; Fossai, G.; Balsari, A.; Sonnino, S.; Colnaghi, M. I. *Cancer Res.* 1983, 43, 1301. (b) Huang. Y. L.; Hung, J. T.: Cheung, S. K.; Lee, H. Y.; Chu, K. C.; Li, S. T.; Lin, Y. C.; Ren, C. T.; Cheng. T. J.; Hsu, T. L.; Yu, A. L.; Wu, C. Y.: Wong, C. H. *Proc. Natl. Acad. Sci. U.S.A.* 2013, 110, 2517. (c) Lou, Y. W.; Wang. P. Y.; Yeh, S. C.; Chuang, P. K.; Li, S. T.; Wu, C. Y.; Khoo, K. H.; Hsiao, M.; Hsu, T. L.; Wong, C. H. *Proc. Natl. Acad. Sci. U.S.A* 2014, 111, 2482.
(14) Gilewski. T.; Ragupathi, G.; Bhuta, S.; Williams, L. J.; Musselli, C.; Zhang, X. F.; Bornmann, W. G.; Spassova, M.; Benesath, K. P.; Panageas, K. S.; Chin, J.; Hudis, C. A.; Norton, L.; Houghton. A. N.; Livingston, P. O.; Danishefsky, S. J. *Proc. Natl. Acad. Sci. U.S.A.* 2001, 98, 3270.
(15) (a) Tsai. T. I.; Lee, H. Y. Chang, S. H.; Wang. C. H.; Tu, Y. C.; Lin, Y. C.; Hwang, D. R.; Wu, C. Y.; Wong, C. H. *J. Am. Chem. Soc.* 2013, 135, 14831. (b) Burkhart, F.; Zhang, Z.; Wacowich-Sgarbi, S.; Wong. C. H. *Angew Chem. Int. Ed.* 2001, 40, 1274.
(16) (a) Slovin, S. F.; Ragupathi, G.; Adluri, S.; Ungers, G.; Terry, K.; Kim, S.; Spassova, M.; Bornmann, W. G.; Fazzari, M.; Dantis. L.; Olkiewiez, K.; Lloyd. K. O.: Livingston. P. O.; Danishefsky, S. J.; Scher, H. I. *Proc. Natl. Acad. Sci. U.S.A.* 1999, 96, 5710. (b) Wang, Z. G.; Williams, L. J.; Zhang, X. F.; Zatorski, A.; Kudryashov. V.; Ragupathi, G.; Spassova. M.; Bornmann, W; Slovin, S. F.; Scher, H. I.: Livingston, P. O.; Lloyd, K. O.; Danishefsky, S. J. *Proc. Natl. Acad. Sci. U.S.A.* 2000, 97, 2719.

(17) (a) Yin, Z. J.; Huang, X. F. *J. Carbohydr. Chem.* 2012, 31, 143. (b) Liu. C. C.; Ye, X. S. *Glycoconjugate J.* 2012, 29, 259.
(18) (a) Jennings, H. J.; Roy, R.; Gamian, A. *J. Immunol.* 1986, 137, 1708. (b) Krug, L. M.; Ragupathi, G.; Ng, K. K.; Hood, C.; Jennings, H. J.; Guo, Z.; Kris, M. G.; Miller, V.; Pizzo, B.; Tyson, L.; Baez. V.; Livingston, P. O. *Clin Cancer Res* 2004, 10, 916. (c) Krug. L. M.; Ragupathi, G.; Hood, C.; George, C.; Hong, F.; Shen, R.; Abrey, L.; Jennings, H. J.; Kris, M. G.; Livingston, P. O. *Cancer Immunol. Immunother.* 2012, 61, 9.
(19) (a) Wu, J.; Guo, Z. *Bioconjugate Chem.* 2006, 17, 1537. (b) Wang, Q.; Ekanayaka, S. A.; Wu, J.; Zhang, J.; Guo, Z. *Bioconjugate Chem.* 2008, 19, 2060. (c) Yang, F.; Zheng, X. J.; Huo, C. X.; Wang. Y.; Zhang, Y.; Ye, X. S. *ACS Chem. Biol.* 2011, 6, 252. (d) Sahabuddin, S.; Chang, T. C.; Lin, C. C.; Jan, F. D.; Hsiao, H. Y.; Huang, K. T.; Chen, J. H.; Horng, J. C.; Ho. J. A. A.; Lin, C. C. *Tetrahedron* 2010, 66, 7510.
(20) Pan, Y.; Chefalo, P.; Nagy, N.; Harding, C.; Guo, Z. *J. Med. Chem.* 2005, 48, 875.
(21) (a) Grunewald, J.; Tsao, M. L., Perera, R.; Dong, L.; Niessen, F.; Wen, B. G.; Kubitz, D. M.; Smider, V. V.; Ruf, W.; Nasoff, M.; Lerner, R. A.; Schultz, P. G. *Proc. Natl. Acad. Sci. U.S.A* 2008, 105, 11276. (b) Grunewald, J.; Hunt, G. S.; Dong, L.; Niessen, F.; Wen. B. G.; Tsao, M. L.; Perera, R.; Kang, M.; Laffitte, B. A.; Azarian, S.; Ruf, W.; Nasoff, M.; Lerner, R. A.; Schultz, P. G.; Smider. V. V. *Proc. Natl. Acad. Sci. U.S.A.* 2009, 106, 4337.
(22) (a) Hoffmann-Roder A.; Johannes, M. *Chem. Commun.* 2011, 47, 9903. (b) Hoffmann-Roder, A.; Kaiser. A.; Wagner, S.; Gaidzik. N.; Kowalezyk. D.; Westerlind, U.; Gerlitzki. B.; Schmitt, E.; Kunz, H. *Angew. Chem. Int. Ed.* 2010, 49, 8498. (c) Oberbillig, T.; Mersch, C.; Wagner, S.; Hoffmann-Roder, A. *Chem. Commun.* 2012, 48, 1487.
(23) (a) Park, T. K.; Kim, I. J.; Hu, S. H.; Bilodeau, M. T.; Randolph, J. T.; Kwon. O.; Danishefsky, S. J. *J. Am. Chem. Soc.* 1996, 118, 11488. (b) Bilodeau, M. T.; Park, T. K.; Hu, S. H.; Randolph, J. T.; Danishefsky, S. J.; Livingston, P. O.; Zhang, S. L. *J. Am. Chem. Soc.* 1995, 117, 7840.
(24) Lassaletta, J. M.; Schmidt. R. R. *Liebigs Ann.* 1996, 1417.
(25) Zhu, T.; Boons, G. *J. Angew Chem. Int. Ed.* 1999, 38, 3495.
(26) Bosse, F.; Marcaurelle, L. A.; Seeberger, P. H. *J. Org. Chem.* 2002, 67, 6659.
(27) Werz, D. B.; Castagner. B.; Seeberger, P. H. *J. Am. Chem. Soc.* 2007, 129, 2770.
(28) Wang, Z.; Zhou, L.; El-Boubbou, K.; Ye. X. S.; Huang, X. *J. Org Chem.* 2007, 72, 6409.
(29) Huang, C. Y.; Thayer, D. A.; Chang, A. Y.; Best, M. D.; Hoffmann, J.; Head, S.; Wong, C. H. *Proc. Natl. Acad. Sci. U.S.A.* 2006, 103, 15.
(30) Su, D. M.; Eguchi, H.; Yi, W.; Li, L.; Wang, P. G.; Xia, C. *Org. Lett.* 2008, 10, 1009.
(31) Zhang, J.; Kowal, P.; Fang, J.; Andreana, P.; Wang, P. G. *Carbohydr. Res.* 2002, 337, 969.
(32) Shao, J.; Zhang. J.; Kowal. P.; Lu, Y.; Wang, P. G. *Biochem. Biophys. Res. Commun.* 2002, 295, 1.
(33) Cai, X. Q.; Tsuchikama, K.; Janda. K. D. *J. Am. Chem. Soc.* 2013, 135, 2971.

What is claimed is:

1. An immunogenic composition comprising:
(a) a glycan conjugate comprising at least one glycan with a linker and a carrier, the at least one glycan being conjugated to the carrier through the linker; and (b) optionally an adjuvant, wherein the at least one glycan with the linker has a chemical structure of formula (II):

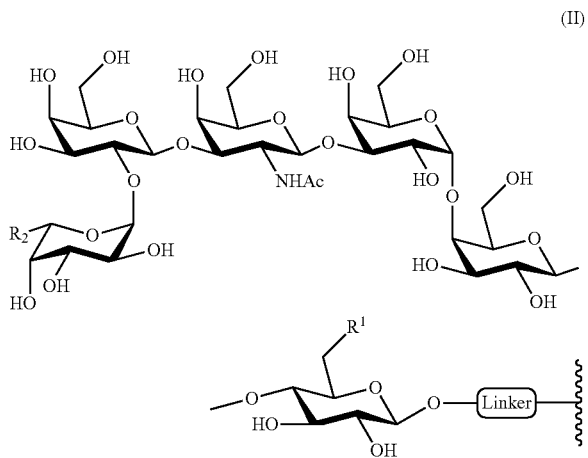

(II)

wherein:
$R^1$ and $R^2$ is independently selected from the group consisting of hydrogen, halogen, optionally substituted alkyl, optionally substituted alkenyl, optionally substituted alkynyl, optionally substituted heterocyclyl, optionally substituted aryl, $-N_3$, $-NO_2$, $-N(R^B)_2$, $-N(R^A)C(O)R^A$, $-OR^A$, $-OC(O)R^A$, $-SR^A$, $-C(O)N(R^B)_2$, $-CN$, $-C(O)R^A$, $-C(O)OR^A$, $-S(O)R^A$, $-SO_2R^A$, $-SO_2N(R^B)_2$, and $NHSO_2R^B$;
$R^A$ is independently selected from the group consisting of hydrogen, optionally substituted alkyl, optionally substituted alkenyl, optionally substituted alkynyl, optionally substituted heterocyclyl, and optionally substituted aryl;
$R^B$ is independently selected from hydrogen, optionally substituted alkyl, optionally substituted alkenyl, optionally substituted alkynyl, optionally substituted heterocyclyl, and optionally substituted aryl; and
provided that when $R^1$ is OH, $R^2$ is not $-CH_3$, and when $R^2$ is $-CH_3$, $R^1$ is not $-OH$.

2. The immunogenic composition of claim 1, wherein $R^1$ is $-OH$, $-F$, $-N_3$, $-NO_2$, or aryloxy.

3. The immunogenic composition of claim 1, wherein $R^2$ is $-CH_3$, $-CH_2F$, $-CH_2N_3$, $-CH_2NO_2$, $-CH_2OH$, or alkynyl.

4. The immunogenic composition of claim 1, wherein $R^1$ is $-F$, $-N_3$ or

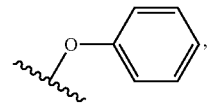 [SMILES: *Oc1ccccc1]

and $R^2$ is $-CH_3$.

5. The immunogenic composition of claim 1, wherein $R^1$ is $-OH$, and $R^2$ is $-CH_2N_3$.

6. The immunogenic composition of claim 1, wherein the carrier is a protein, a lipid, a lipolized protein, a virus, a peptide, or a dendrimer of glycopeptides.

7. The immunogenic composition of claim 6, wherein the carrier protein is selected from the group consisting of tetanus toxoid (TT), diphtheria toxoid (DT), diphtheria toxin cross-reacting material 197 (CRM197), fragment C of TT, Keyhole limpet hemocyanin (KLH), bovine serum albumin (BSA), protein D, outer-membrane protein (OMP) and pneumolysin.

8. The immunogenic composition of claim 7, wherein the carrier protein is CRM197, and the glycan conjugate has a chemical structure of formula (III):

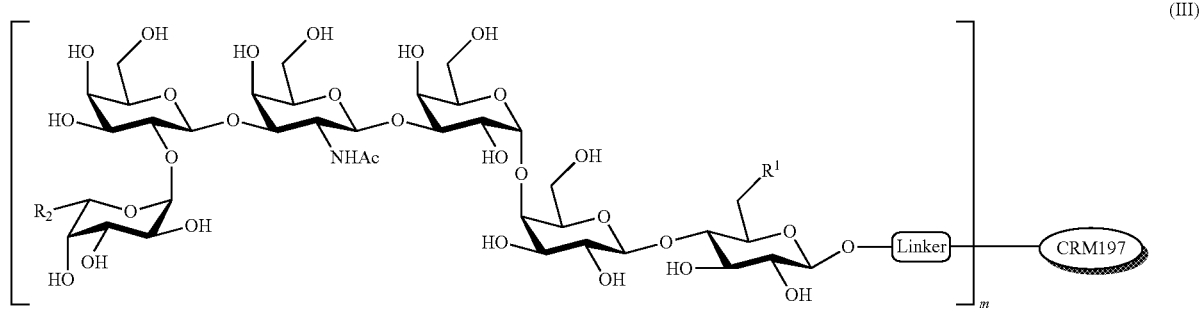

wherein
   m is an integer from 1 to 38; and
   provided that when $R^1$ is —OH, $R^2$ is not —CH$_3$; and when $R^2$ is —CH$_3$, $R^1$ is not —OH.

9. The immunogenic composition of claim 1, wherein the linker is a hetero- or homo-bifunctional linker.

10. The immunogenic composition of claim 9, wherein the linker is an amino-active homo-bifunctional linker with 2-20 carbons that can form an amide bond with the at least one glycan and the carrier protein, respectively.

11. The immunogenic composition of claim 1, wherein the adjuvant is a glycolipid capable of binding a CD1d molecule on a dendritic cell.

12. The immunogenic composition of claim 1, wherein the adjuvant is C34, 7DW8-5, C17, C23, Aluminum salt, Squalene, MF59, or QS-21.

13. A cancer vaccine, comprising the immunogenic composition of claim 1 and a pharmaceutically acceptable excipient.

14. A method of treating a cancer in a subject, comprising administering to the subject an effective amount of an immunogenic composition as claimed in claim 1, wherein the cancer expresses Globo H, SSEA3 and/or SSEA4 antigen.

15. The method of claim 14, wherein the cancer is selected from the group consisting of brain cancer, lung cancer, breast cancer, oral cancer, esophagus cancer, stomach cancer, liver cancer, bile duct cancer, pancreas cancer, colon cancer, kidney cancer, bone cancer, skin cancer, cervix cancer, ovary cancer, and prostate cancer.

16. A process for making the immunogenic composition of claim 1, comprising: providing the carrier; and conjugating the at least one glycan to the carrier through the linker by a conjugation reaction.

17. The process of claim 16, wherein the linker comprises at least one sulfur atom, carboxylate group, amide group, carbamate group, carbonate group, thiocarbamate group, thiocarbonate group, thioether group, succinamide group, n-hydroxy succinamide group, or any combination thereof.

18. A compound of formula (I):

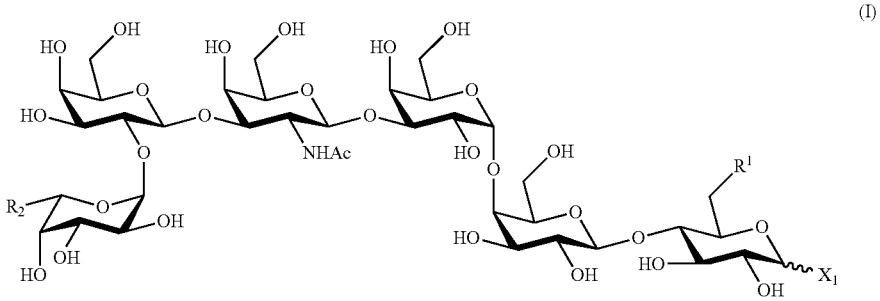

wherein:
   $X_1$ is —OR or —SR, wherein R is hydrogen, an oxygen or sulfur protecting group, optionally substituted $C_{1-10}$ alkyl, optionally substituted aryl, optionally substituted acyl, or optionally substituted imidoyl;
   $R^1$ and $R^2$ is independently selected from the group consisting of hydrogen, halogen, optionally substituted alkyl, optionally substituted alkenyl, optionally substituted alkynyl, optionally substituted heterocyclyl, optionally substituted aryl, —N$_3$, —NO$_2$, —N(R$^B$)$_2$, —N(R$^A$)C(O)R$^A$, —OR$^A$, —OC(O)R$^A$, —SR$^A$, —C(O)N(R$^B$)$_2$, —CN, —C(O)R$^A$, —C(O)OR$^A$, —S(O)R$^A$, —SO$_2$R$^A$, —SO$_2$N(R$^B$)$_2$, and —NHSO$_2$R$^B$;
   $R^A$ is selected from the group consisting of hydrogen, optionally substituted alkyl, optionally substituted alkenyl, optionally substituted alkynyl, optionally substituted heterocyclyl, and optionally substituted aryl;
   $R^B$ is selected from the group consisting of hydrogen, optionally substituted alkyl, optionally substituted alkenyl, optionally substituted alkynyl, optionally substituted heterocyclyl, and optionally substituted aryl; and provided that when $R^1$ is —OH, $R^2$ is not —CH$_3$, and when $R^2$ is —CH$_3$, $R^1$ is not —OH.

19. The compound of claim 18, wherein $R^1$ is selected from the group consisting of —F, —N$_3$, —NO$_2$,

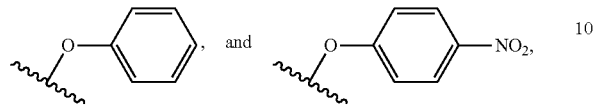

and $R^2$ is —CH$_3$.

20. The compound of claim 18, wherein $R^1$ is —OH and $R^2$ is selected from the group consisting of —CH$_2$F, —CH$_2$N$_3$, —CH$_2$NO$_2$, —CH$_2$OH, and —C≡CH.

21. A process of preparing the immunogenic composition of claim 1, comprising:
(i) providing a compound of Formula (X):

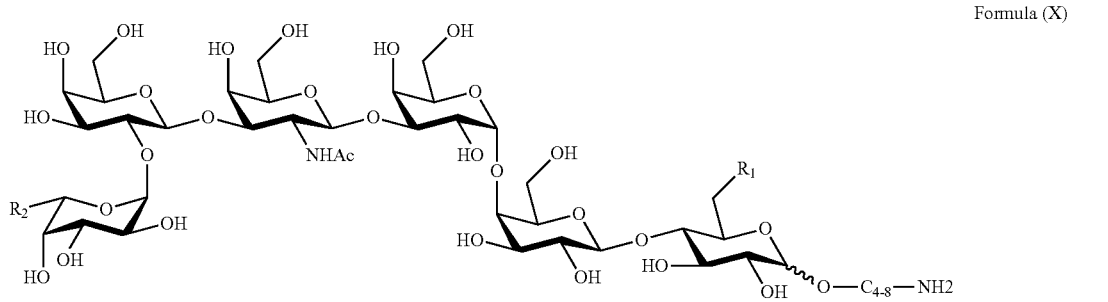

Formula (X)

wherein:
$R^1$ and $R^2$ $R^A$ $R^B$ are as defined above in Formula (II); and
provided that when $R^1$ is —OH, $R^2$ is not —CH$_3$, and when $R^2$ is —CH$_3$, $R^1$ is not —OH,
(ii) reacting the compound of Formula (X) with an amino-active bifunctional linker to afford a first reaction product; and
(iii) reacting the first reaction product with a carrier protein to afford a glycan conjugate; and
(iv) optionally admixing an adjuvant to afford the composition of claim 1.

22. The process of claim 21, wherein the amino-active bifunctional linker is a dicarboxylic acid having 4 to 6 carbons.

23. The process of claim 21, wherein the carrier is a protein, a lipid, a lipolized protein, a virus, a peptide, or a dendrimer of glycopeptides.

24. The process of claim 21, wherein $R^1$ is selected from the group consisting of —F, —N$_3$, —NO$_2$,

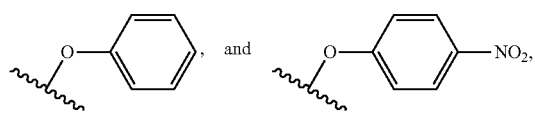 [SMILES: *Oc1ccccc1 ; *Oc1ccc([N+](=O)[O-])cc1]

and $R^2$ is —CH$_3$, or wherein $R^1$ is —OH and $R^2$ is selected from the group consisting of —CH$_2$F, —CH$_2$N$_3$, —CH$_2$NO$_2$, —CH$_2$OH, and —C≡CH.

* * * * *